US010857246B2

(12) United States Patent
Yang et al.

(10) Patent No.: US 10,857,246 B2
(45) Date of Patent: Dec. 8, 2020

(54) NUCLEAR IMAGING AND RADIOTHERAPEUTICS AGENTS TARGETING CARBONIC ANHYDRASE IX AND USES THEREOF

(71) Applicant: THE JOHNS HOPKINS UNIVERSITY, Baltimore, MD (US)

(72) Inventors: Xing Yang, Baltimore, MD (US); Il Minn, Ellicott City, MD (US); Steven Rowe, Parkville, MD (US); Sangeeta Ray, Ellicott City, MD (US); Ronnie C. Mease, Fairfax, VA (US); Michael Gorin, Towson, MD (US); Mohamad Allaf, Baltimore, MD (US); Martin G. Pomper, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/578,473

(22) PCT Filed: Jun. 1, 2016

(86) PCT No.: PCT/US2016/035259
§ 371 (c)(1),
(2) Date: Nov. 30, 2017

(87) PCT Pub. No.: WO2016/196628
PCT Pub. Date: Dec. 8, 2016

(65) Prior Publication Data
US 2018/0133348 A1 May 17, 2018

Related U.S. Application Data

(60) Provisional application No. 62/169,338, filed on Jun. 1, 2015, provisional application No. 62/336,043, filed on May 13, 2016.

(51) Int. Cl.
*A61K 51/04* (2006.01)
*C07D 417/14* (2006.01)
*C07D 417/12* (2006.01)
*A61P 35/00* (2006.01)

(52) U.S. Cl.
CPC .......... *A61K 51/0497* (2013.01); *A61P 35/00* (2018.01); *C07D 417/12* (2013.01); *C07D 417/14* (2013.01)

(58) Field of Classification Search
CPC ................. A61K 51/00; A61K 51/04
See application file for complete search history.

(56) References Cited

U.S. PATENT DOCUMENTS

2009/0175794 A1* 7/2009 Zimmerman ........ A61K 31/18
424/9.1

OTHER PUBLICATIONS

Moreno Wichert et al. Dual-display of small molecules enables the discovery of ligand pairs and facilitates affinity maturation, Nature Chemsitry, vol. 7, 241-249. (Year: 2015).*
Moreno Wichert et al. Dual-display of small molecules enables the discovery of ligand pairs and facilitates affinity maturation, Nature Chemistry, col. 7, 241-249. (Year: 2015).*
Alauddin, Positron emission tomography (PET) imaging with (18)F-based radiotracers. Am J Nucl Med Mol Imaging. 2012;2:55-76.
Alquicer et al., Development of a high-throughput fluorescence polarization assay to identify novel ligands of glutamate carboxypeptidase II. Journal of biomolecular screening. 2012; 17(8):1030-1040.
Alterio et al., Multiple binding modes of inhibitors to carbonic anhydrases: how to design specific drugs targeting 15 different isoforms? Chemical reviews. 2012; 112(8):4421-4468.
Askoxylakis et al., A new peptide ligand for targeting human carbonic anhydrase IX, identified through the phage display technology. PLoS One. 2010;5:e15962.
Atkins et al., Carbonic anhydrase IX expression predicts outcome of interleukin 2 therapy for renal cancer. Clinical cancer research : an official journal of the American Association for Cancer Research. 2005; 11(10):3714-3721.
Bao et al., In vivo imaging and quantification of carbonic anhydrase IX expression as an endogenous biomarker of tumor hypoxia. PLoS One. 2012;7:e50860.
Brenner et al., Encoded combinatorial chemistry. Proceedings of the National Academy of Sciences of the United States of America. 1992; 89(12):5381-5383.
Bui et al., Carbonic anhydrase IX is an independent predictor of survival in advanced renal clear cell carcinoma: implications for prognosis and therapy. Clinical cancer research : an official journal of the American Association for Cancer Research. 2003; 9(2):802-811.
Chen et al., Advance of molecular imaging technology and targeted imaging agent in imaging and therapy. Biomed Res Int. 2014; 2014: 819324.
Cho et al., Biodistribution, tumor detection, and radiation dosimetry of 18F-DCFBC, a low-molecular-weight inhibitor of prostate-specific membrane antigen, in patients with metastatic prostate cancer. Journal of nuclear medicine : official publication, Society of Nuclear Medicine. 2012; 53(12):1883-1891.
Coenen et al., Fluorine-18 radiopharmaceuticals beyond [18F]FDG for use in oncology and neurosciences. Nuclear medicine and biology. 2010; 37(7):727-740.

(Continued)

*Primary Examiner* — Jake M Vu
*Assistant Examiner* — Jagadishwar R Samala
(74) *Attorney, Agent, or Firm* — Casimir Jones, S.C.; Jeffrey W. Childers

(57) ABSTRACT

Highly potent and selective radionuclide-based imaging and therapy agents targeting carbonic anhydrase IX with minimum non-specific organ uptake are disclosed. Methods of imaging and/or treating carbonic anhydrase IX-expressing cells or tumors also are disclosed.

27 Claims, 23 Drawing Sheets

(56) References Cited

OTHER PUBLICATIONS

Franzini et al., DNA-encoded chemical libraries: advancing beyond conventional small-molecule libraries. Accounts of chemical research. 2014; 47(4):1247-1255.

Grabmaier et al., Strict regulation of CAIX(G250/MN) by HIF-1alpha in clear cell renal cell carcinoma. Oncogene. 2004; 23(33):5624-5631.

Ivanov et al., Expression of hypoxia-inducible cell-surface transmembrane carbonic anhydrases in human cancer. The American journal of pathology. 2001; 158(3):905-919.

Krall et al., A small-molecule drug conjugate for the treatment of carbonic anhydrase IX expressing tumors. Angew Chem Int Ed Engl. 2014 ; 53(16) : 4231-5.

Krishnamurthy et al., Carbonic anhydrase as a model for biophysical and physical-organic studies of proteins and protein-ligand binding. Chem Rev. 2008;108:946-1051. PMCID:PMC2740730.

Leibovich et al., Carbonic anhydrase IX is not an independent predictor of outcome For patients with clear cell renal cell carcinoma. Journal of clinical oncology : official journal of the American Society of Clinical Oncology. 2007; 25(30):4757-4764.

Lipworth et al., Renal cell cancer histologic subtype distribution differs by race and sex. BJU international. 2014.

Pan et al., Synthesis and evaluation of 18F-labeled carbonic anhydrase IX inhibitors for imaging with positron emission tomography. Journal of enzyme inhibition and medicinal chemistry. 2014; 29(2):249-255.

Peeters et al., [F]VM4-037 MicroPET Imaging and Biodistribution of Two In Vivo CAIX-Expressing Tumor Models. Molecular imaging and biology : MIB : the official publication of the Academy of Molecular Imaging. 2015.

Potter et al., Hypoxia inducible carbonic anhydrase IX, marker of tumour hypoxia, survival pathway and therapy target. Cell cycle. 2004; 3(2):164-167.

Siegel et al., Cancer statistics, 2015. CA: a cancer journal for clinicians. 2015; 65(1):5-29.

Smaldone et al., Potential role of (124)I-girentuximab in the pre-surgical diagnosis of clear-cell renal cell cancer. Biologics : targets & therapy. 2012; 6:395-407.

Srigley et al., The International Society of Urological Pathology (ISUP) Vancouver Classification of Renal Neoplasia. The American journal of surgical pathology. 2013; 37(10):1469-1489.

Supuran, Carbonic anhydrases: novel therapeutic applications for inhibitors and activators. Nature reviews Drug discovery. 2008; 7(2):168-181.

Umbreit et al., Metastatic potential of a renal mass according to original tumour size at presentation. BJU international. 2012; 109(2):190-194; discussion 194.

Wadas et al., Coordinating radiometals of copper, gallium, indium, yttrium, and zirconium for PET and SPECT imaging of disease. Chemical reviews. 2010; 110(5):2858-2902.

Youn et al., In vivo noninvasive small animal molecular imaging. Osong Public Health Res Perspect. 2012; 3 :48-59. PMCID: PMC3738683.

Cancer Genome Atlas Research Network. Comprehensive molecular characterization of clear cell renal cell carcinoma. Nature. Jul. 4, 2013;499(7456):43-9.

International Search Report and Written Opinion for PCT/US2016/035269, dated Oct. 18, 2016, 15 pages.

\* cited by examiner

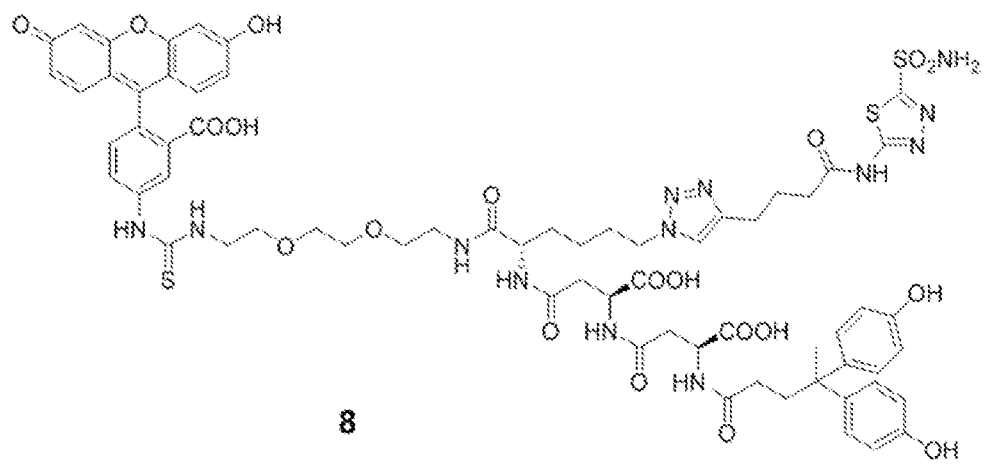
*Fig. 2A*
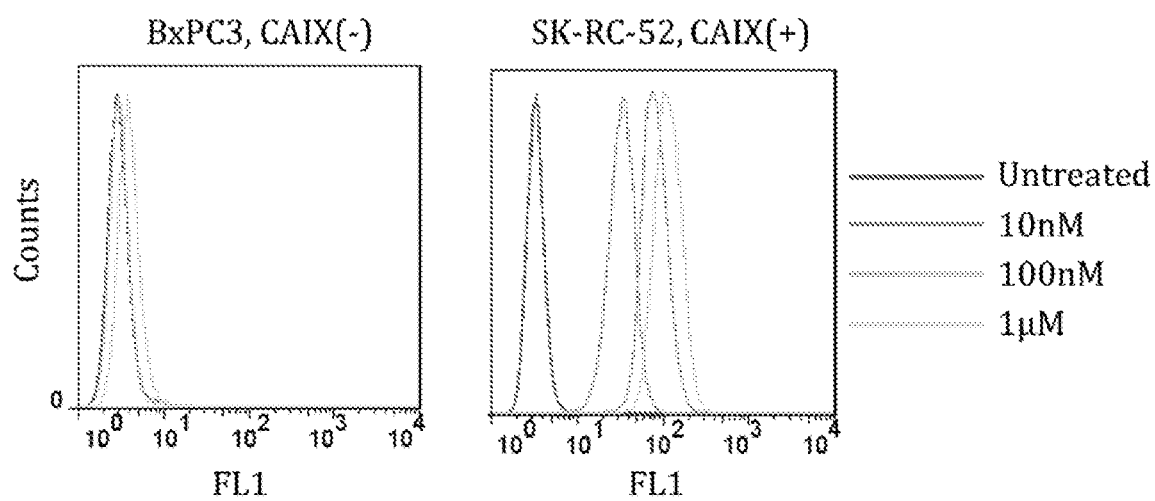
*Fig. 2B*  *Fig. 2C*

NUCLEAR IMAGING AND RADIOTHERAPEUTICS AGENTS TARGETING CARBONIC ANHYDRASE IX AND USES THEREOF

CROSS-REFERENCE TO RELATED APPLICATIONS

This application is a 35 U.S.C. § 371 National Stage Entry of International Application No. PCT/US16/035259 having an international filing date of Jun. 1, 2016, which claims the benefit of U.S. Provisional Application Nos. 62/169,338, filed Jun. 1, 2015, and 62/336,043 filed May 13, 2016, the contents of which are incorporated herein by reference in their entirety.

FEDERALLY SPONSORED RESEARCH OR DEVELOPMENT

This invention was made with government support under CA183031, CA197470, CA184228, and CA134675 awarded by the National Institutes of Health (NIH). The government has certain rights in the invention.

BACKGROUND

Renal cell carcinoma (RCC) is the most common neoplasm of the kidney (Srigley et al., 2013), with an estimated 60,000 patients diagnosed annually in the United States (Siegel et al., 2015). Among cases of RCC, the clear cell subtype (ccRCC) is the most prevalent, accounting for up to 70% of RCCs (Pichler et al., 2010; Lipworth et al., 2014; Umbreit et al., 2012). Common to ccRCC is loss of the Von Hippel-Lindau (VHL) tumor suppressor gene (Shuch et al., 2015). Loss of VHL in turn leads to over-expression of carbonic anhydrase IX (CAIX) (Bragmaier et al., 2004), a membrane-associated enzyme responsible for catalyzing the reversible hydration of carbon dioxide to a bicarbonate anion and a proton (Supuran, 2008; Alterio et al., 2012). Over-expression of CAIX has been demonstrated in approximately 95% of ccRCC tumor specimens (Bui et al., 2003; Atkins et al., 2005; Leibovitch et al., 2007), making it a useful biomarker for this disease.

CAIX has limited expression in normal tissues and organs with the exception of the gastrointestinal tract, gallbladder and pancreatic ducts (Alterio et al., 2012; Clare and Supuran, 2006; Ivanov et al., 2001; Potter and Harris, 2004). No report has demonstrated CAIX expression in normal renal parenchyma or benign renal masses (Supuran, 2008; Alterio et al., 2012; Clare and Supuran, 2006; Ivanov et al., 2001; Potter and Harris, 2004). Feasibility for the non-invasive diagnosis of ccRCC based on CAIX expression has been proved with the radiolabeled antibody G250 (Oosterwijk et al., 1986) and its clinical potential has been reviewed (Smaldone et al., 2012). However, antibodies as molecular imaging agents suffer from pharmacokinetic limitations, including slow blood and non-target tissue clearance (normally 2-5 days or longer) and non-specific organ uptake. Low-molecular-weight (LMW) agents demonstrate faster pharmacokinetics and higher specific signal within clinically convenient times after administration. They also offer site specific radiolabeling often by a wider range of chemical methods and radionuclides, and may offer a shorter path to regulatory approval (Coenen et al., 2010; Cho et al., 2012; Reilly et al., 2015).

Targeting CAIX with LMW inhibitors has proved challenging in part because fifteen human isoforms of carbonic anhydrase, with high sequence homology, have been identified. Those isoforms share common structural features, including a zinc-containing catalytic site, a central twisted β-sheet surrounded by helical connections, and additional β-strands. The isoforms, however, do vary widely in terms of intracellular location, expression levels, and tissue and organ distribution (Supuran, 2008; Alterio et al., 2012). Significant effort has been expended on development of sulfonamides and other LMW CAIX ligands for nuclear imaging of CAIX, but most reported agents have been fraught with low tumor uptake and significant off-target accumulation (Pan et al., 2014; Akurathi et al., 2010; Lu et al., 2013; Doss et al., 2014; Rana et al., 2012; Peeters et al., 2015).

A new LMW CAIX targeting agent has recently been reported that is composed of two binding motifs, one accessing the CAIX active site and the other binding to an as yet unidentified site (Wichert et al., 2015). Conjugated with the infrared dye IRDye®750, the dual-motif inhibitor showed 10% injected dose per gram of tumor (ID/g) tumor uptake. In comparison, agents targeting only the active site show 2% ID/g tumor uptake (Wichert et al., 2015). However, this optical agent also demonstrated high kidney as well as other non-specific organ uptake at 24 h post-administration. Additionally, utility of this agent for in vivo studies is somewhat limited due to the substantial attenuation of light emission through tissue inherent to optical agents. Such limitations call for an agent that retains affinity for CAIX, but clears rapidly from non-target tissues and can be detected with existing clinical instrumentation.

SUMMARY

In some aspects, the presently disclosed subject matter provides compounds of Formula (I):

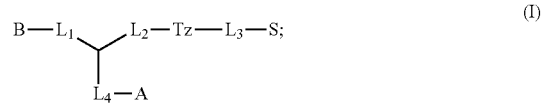

wherein: B is a metal chelating moiety optionally comprising a metal or a radiometal, or a halogenated or radiohalogenated prosthetic group; $L_1$, $L_2$, $L_3$, and $L_4$ are —$C_1$-$C_{24}$ alkyl-, wherein each alkyl group is optionally substituted with one to four groups selected from the group consisting of =O, =S, and —COOR and one to six of the methylene groups in each alkyl group is optionally replaced by —O—, —S—, or —(NR')—, provided that no two adjacent methylene groups are both replaced by —O—, —S—, or —(NR')—; each R and R' is independently selected from the group consisting of hydrogen, $C_1$-$C_6$ alkyl, $C_2$-$C_{12}$ aryl, and $C_4$-$C_{16}$ alkyl aryl; Tz is a triazole group selected from the group consisting of

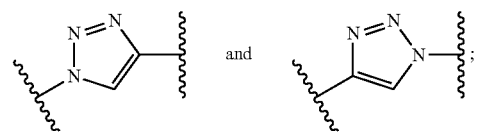 [SMILES: *c1cn(*)nn1 ; *c1cn(*)nn1]

S is a sulfonamide selected from the group consisting of:

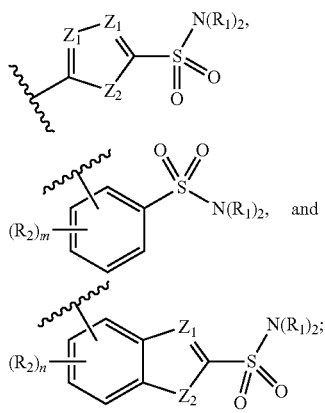

each $R_1$ is independently selected from the group consisting of hydrogen, substituted or unsubstituted alkyl, substituted and unsubstituted aryl, and substituted and unsubstituted heteroaryl; each $R_2$ is selected from the group consisting of hydrogen, halogen, hydroxyl, alkoxyl, —CN, —$CF_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; m is an integer selected from the group consisting of 1, 2, 3, and 4; n is an integer selected from the group consisting of 1, 2, and 3; each $Z_1$ is independently selected from the group consisting of $CR_3$, and N; each $Z_2$ is independently selected from the group consisting of $CR_3$, and S; each $R_3$ is independently selected from the group consisting of hydrogen, halogen, hydroxyl, alkoxyl, —CN, —$CF_3$, amino, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; A is

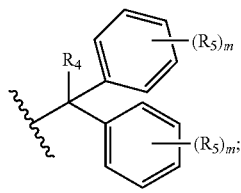

$R_4$ is independently selected from the group consisting of hydrogen, hydroxyl, alkoxyl, substituted or unsubstituted alkyl, substituted or unsubstituted alkenyl, and substituted or unsubstituted alkynyl; $R_5$ is independently selected from the group consisting of hydrogen, halogen, hydroxyl, alkoxyl, —CN, —$CF_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; or a pharmaceutically acceptable salt thereof.

In other aspects, the presently disclosed subject matter provides a method for imaging or treating one or more Carbonic Anhydrase IX-expressing tumors or cells, the method comprising contacting the one or more tumors or cells with an effective amount of a compound of formula (I), and making an image.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1A:
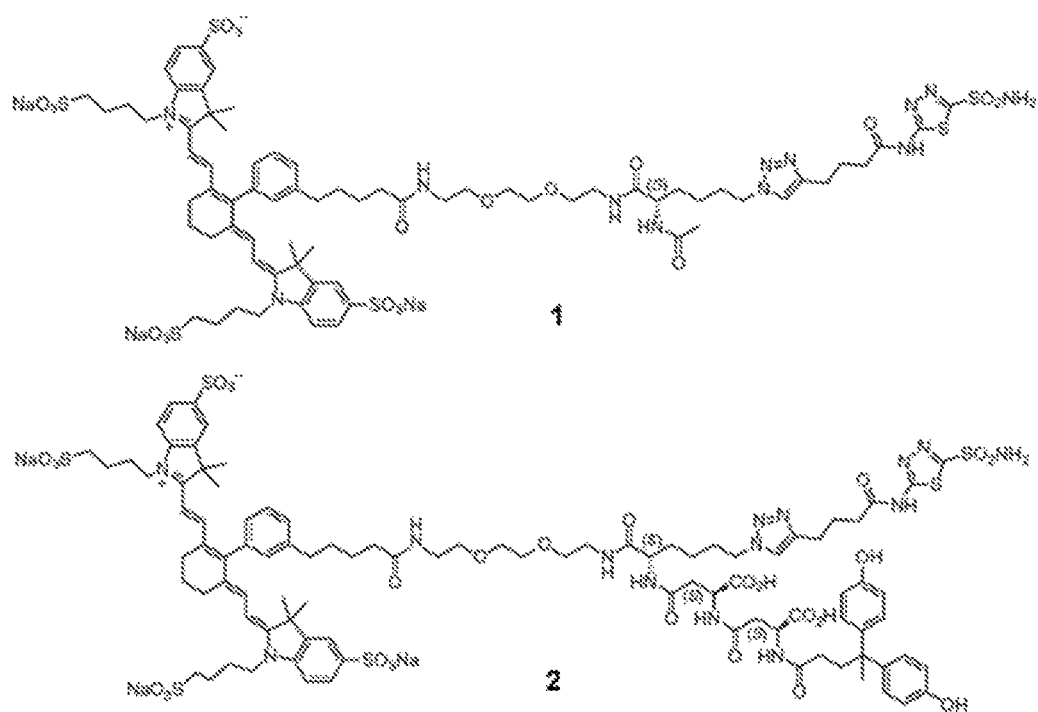
Figure 1B:
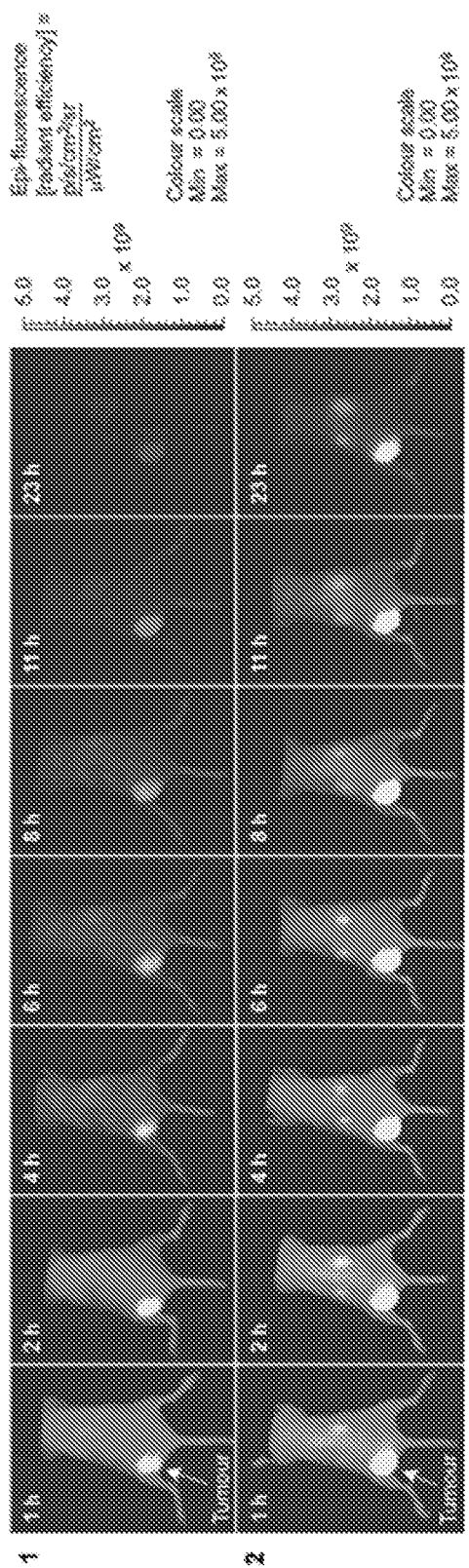
Figure 1C:
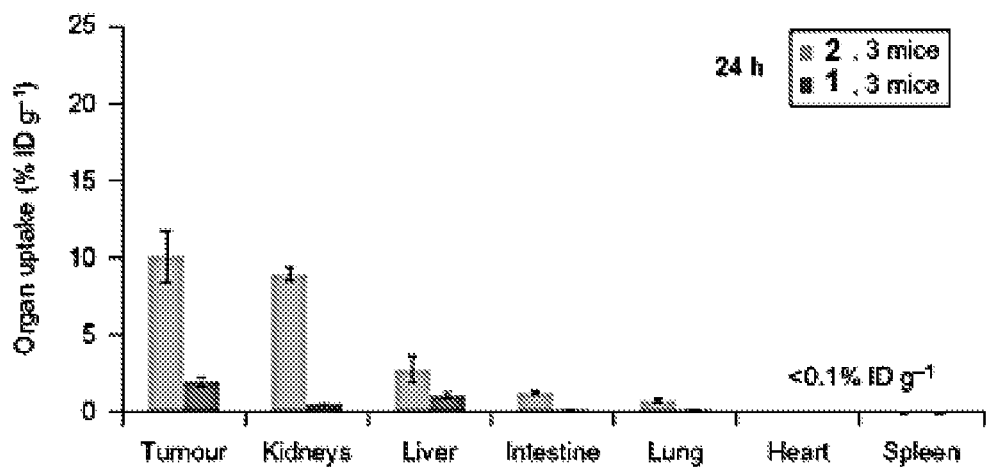
Figure 1D:
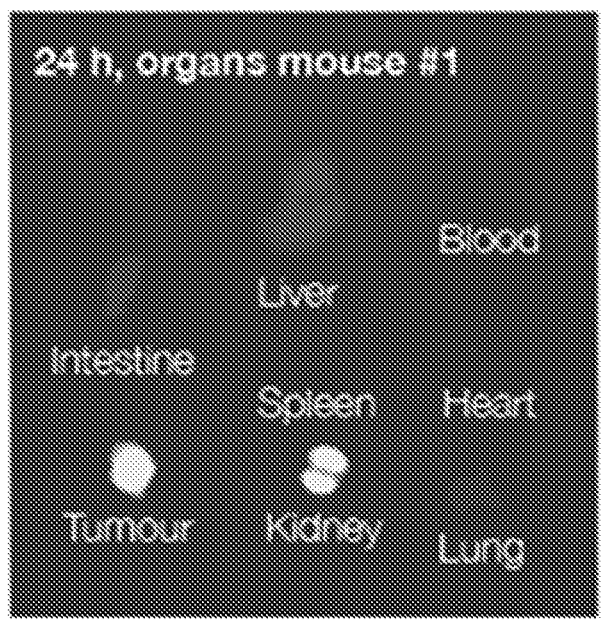
Figure 3A:
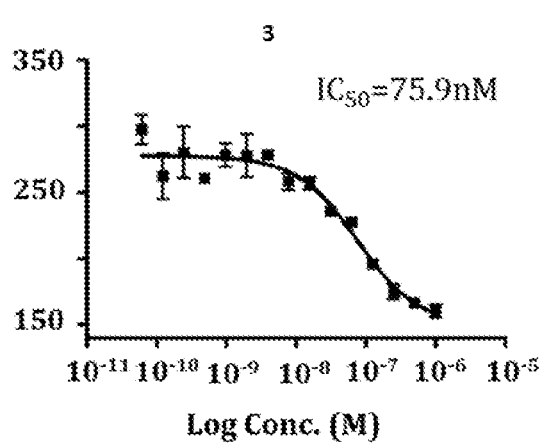
Figure 3B:
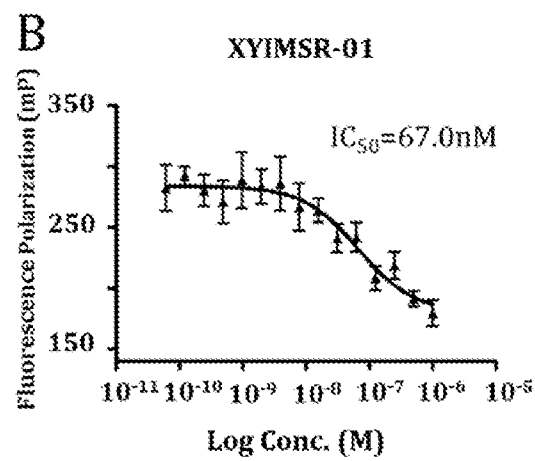
Figure 3C:
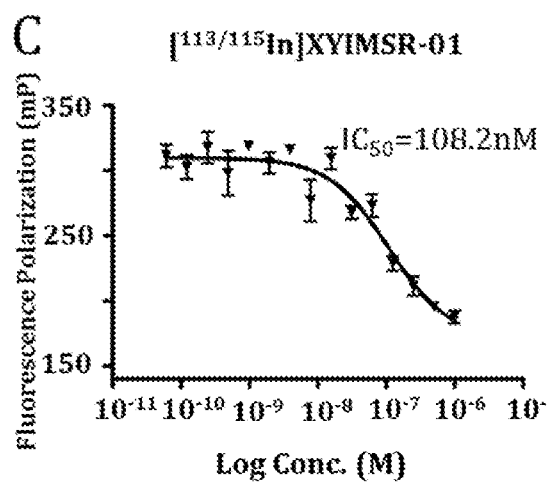
Figure 4A:
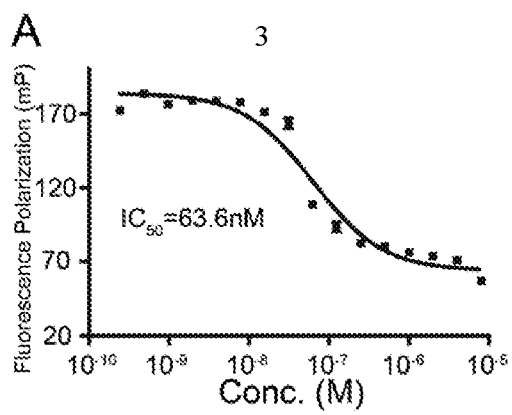
Figure 4B:
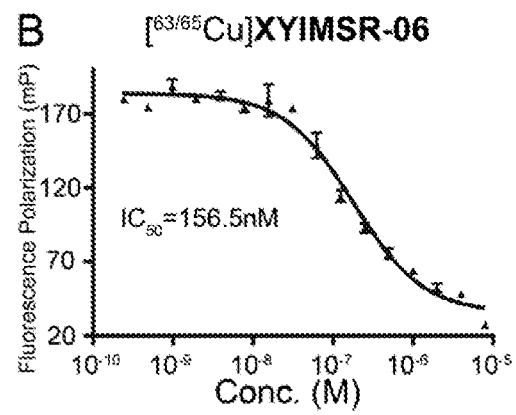
Figure 4C:
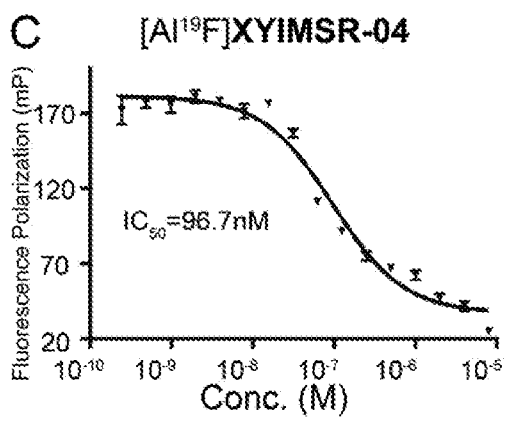
Figure 4D:
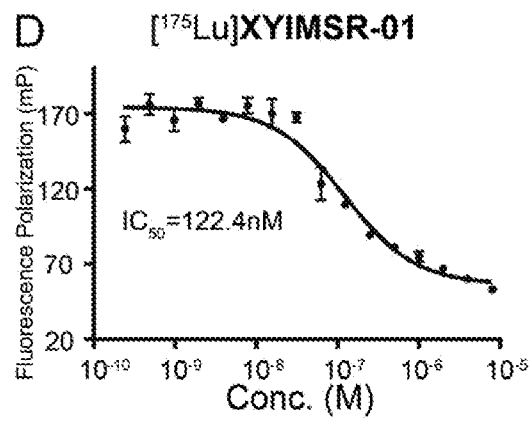
Figure 5:
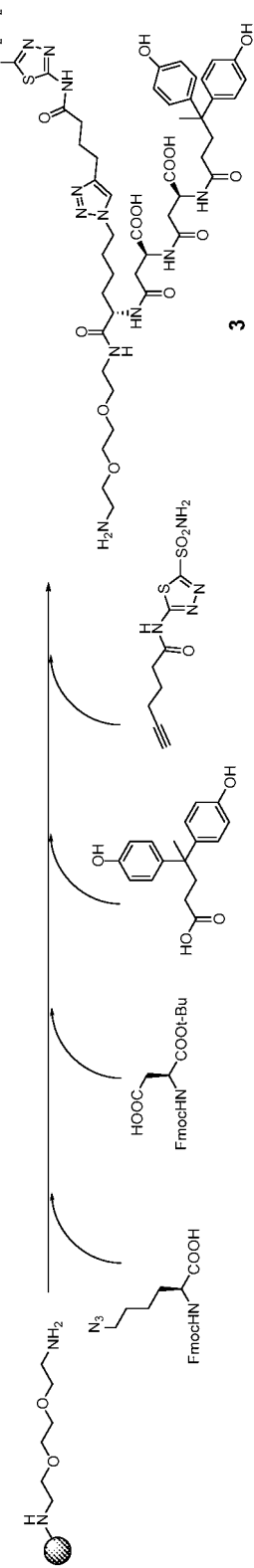
Figure 6:
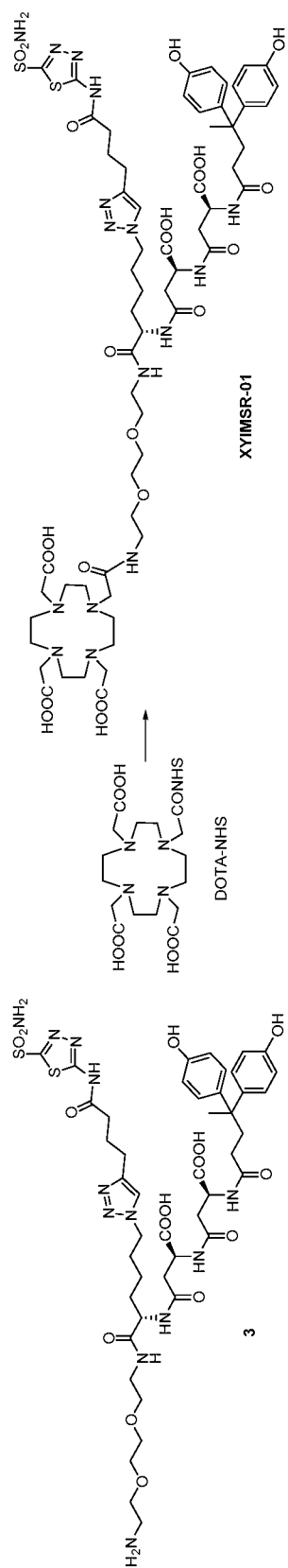
Figure 7:
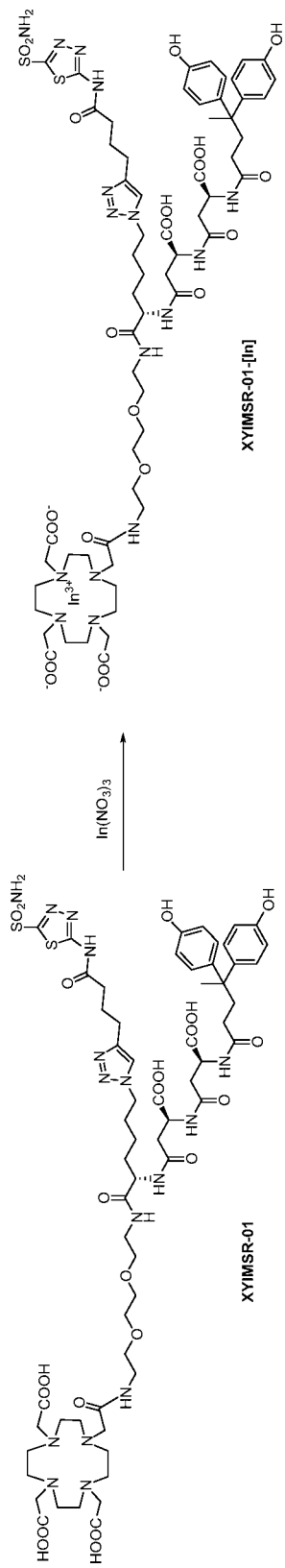
Figure 8:
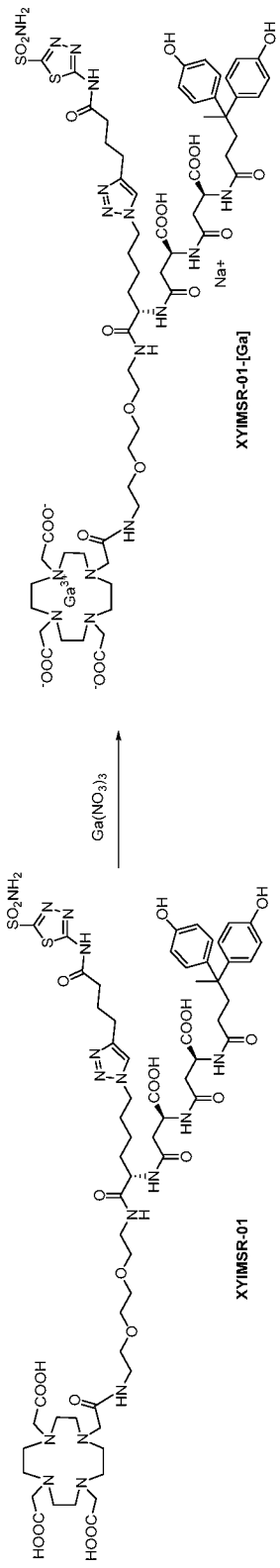
Figure 9:
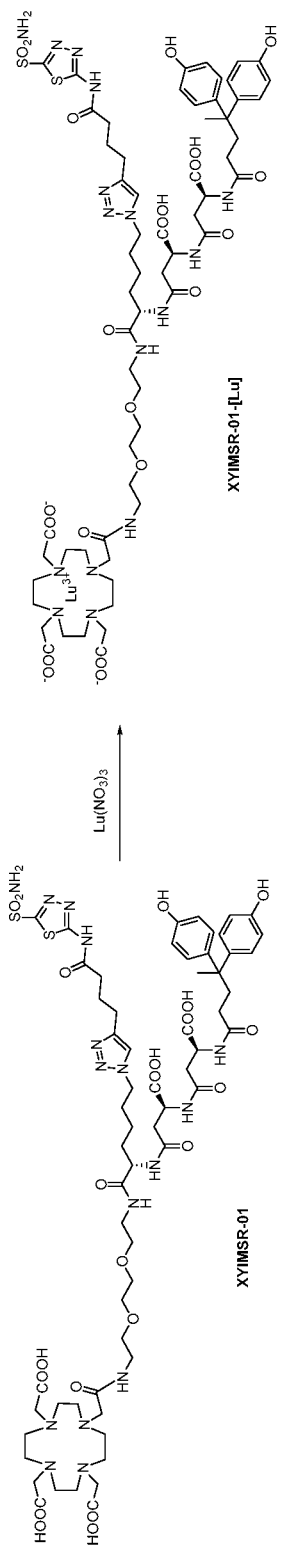
Figure 10:
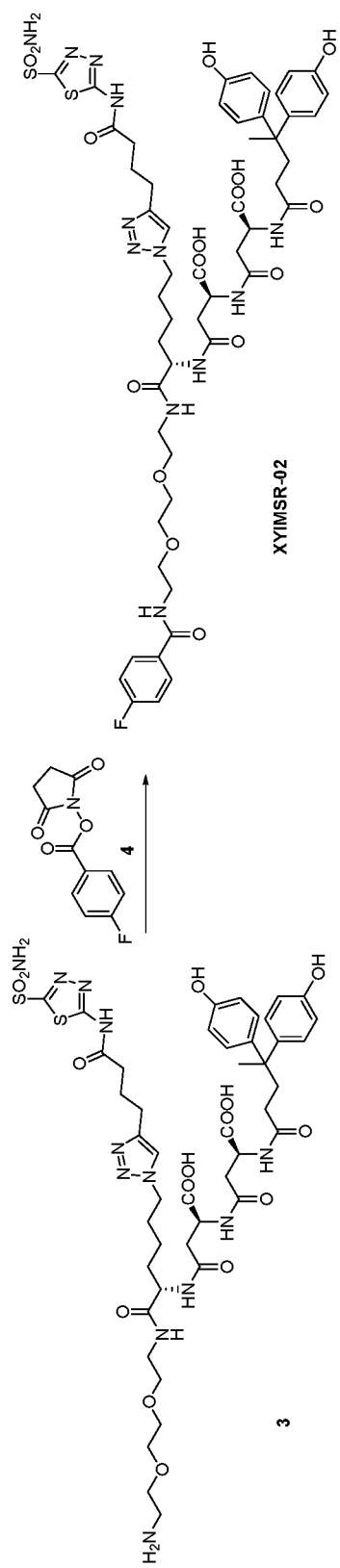
Figure 11:
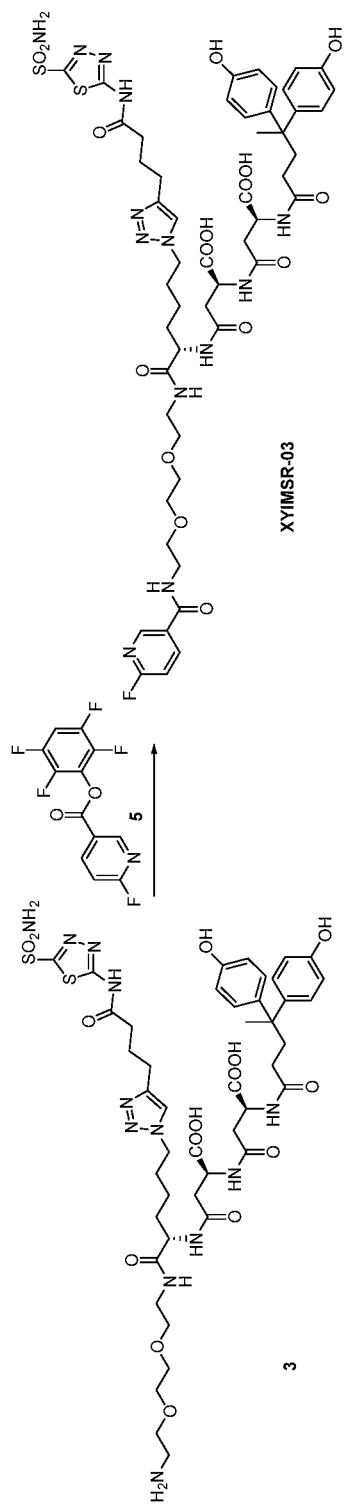
Figure 12:
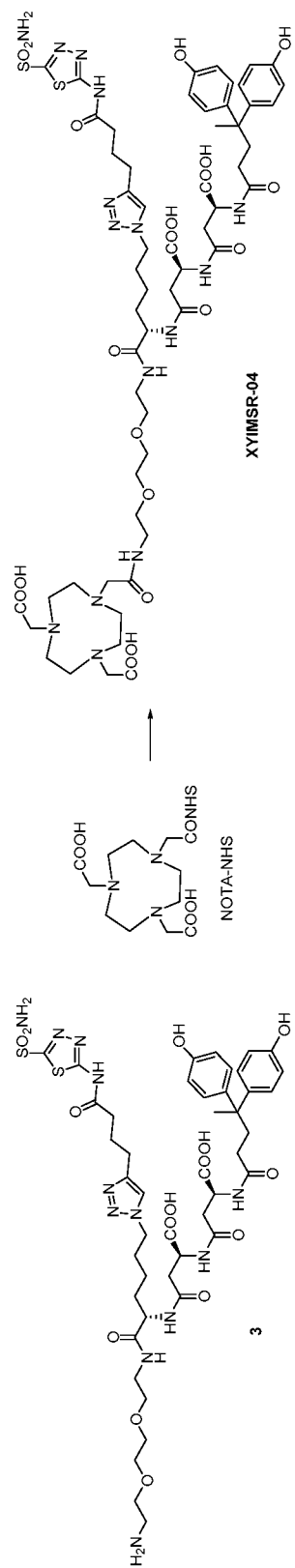
Figure 13:
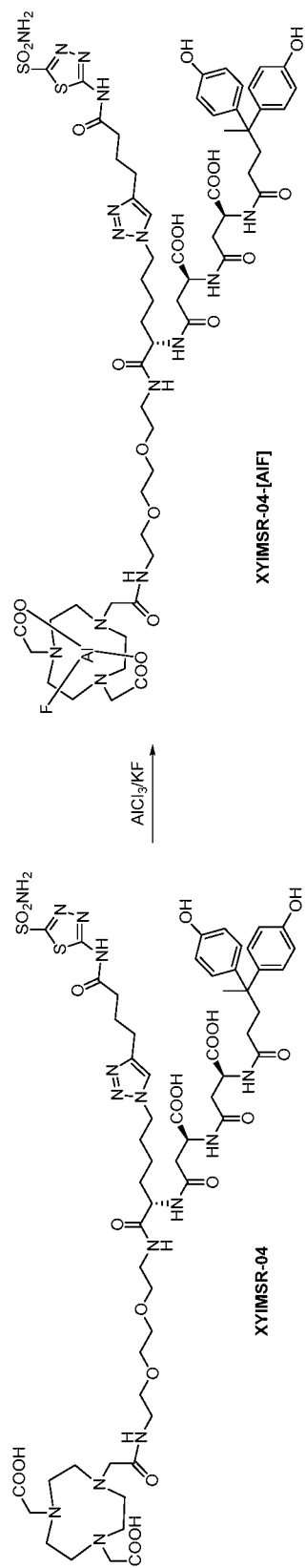
Figure 14:
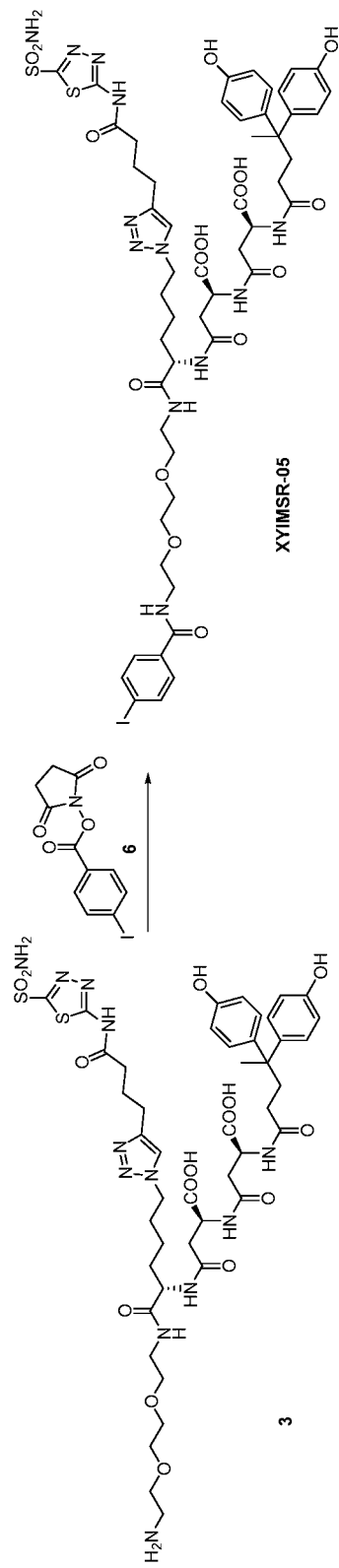
Figure 15:
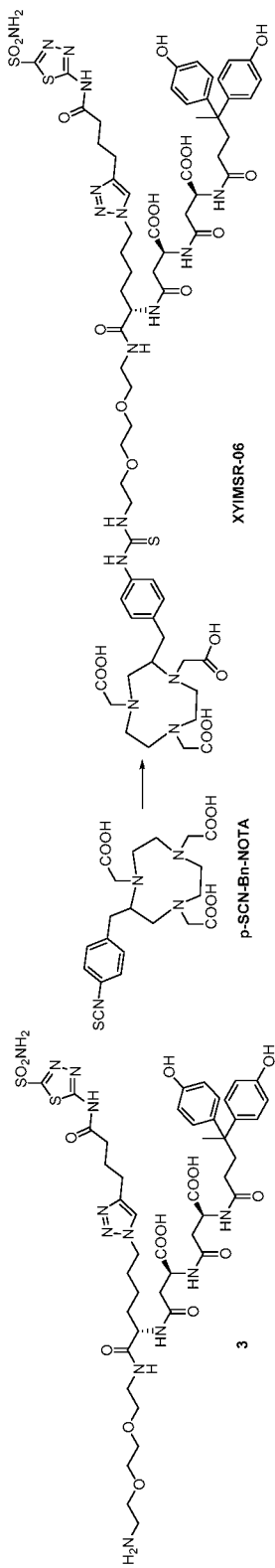
Figure 16:
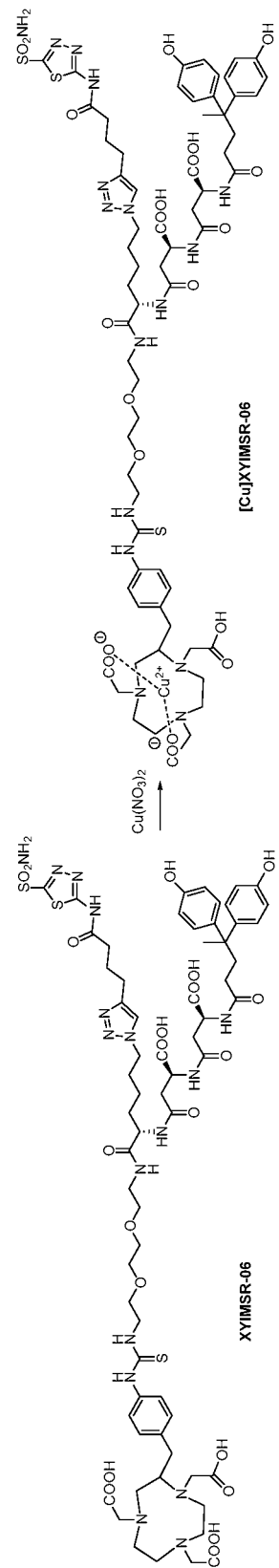
Figure 17:
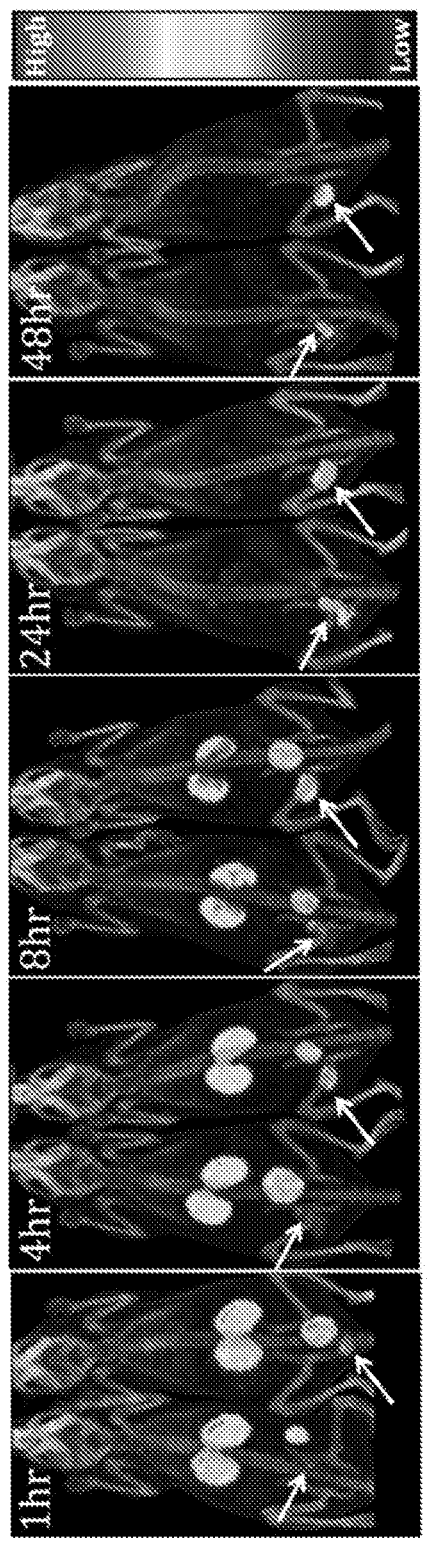
Figure 18:
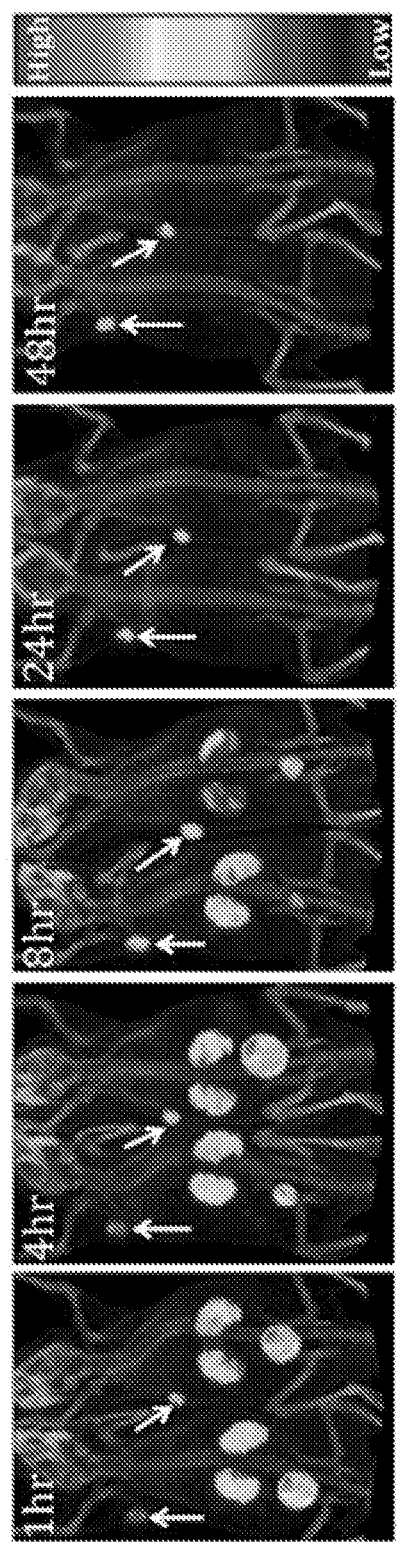
Figure 19:
Figure 20:
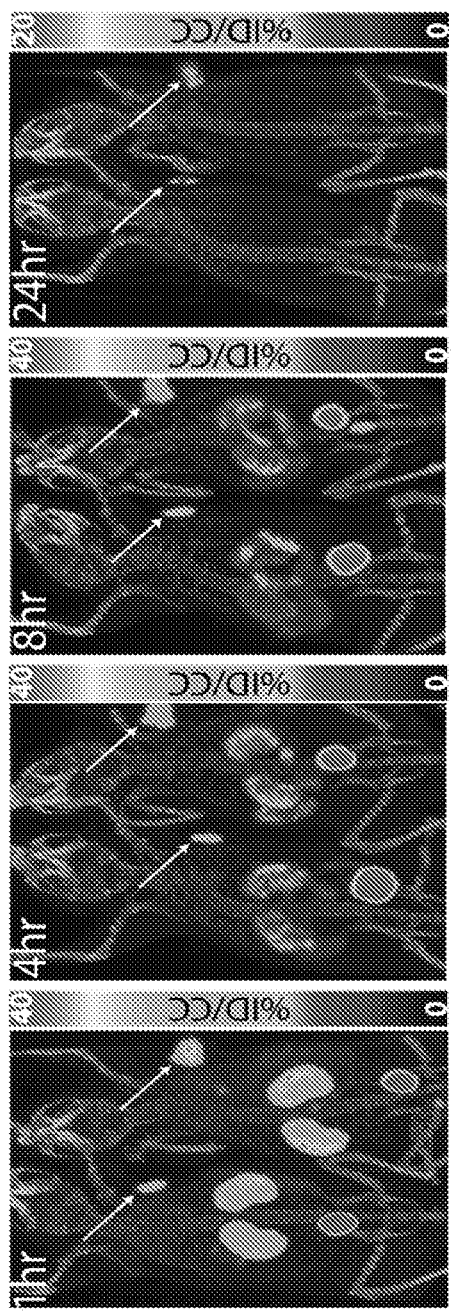
Figure 21:
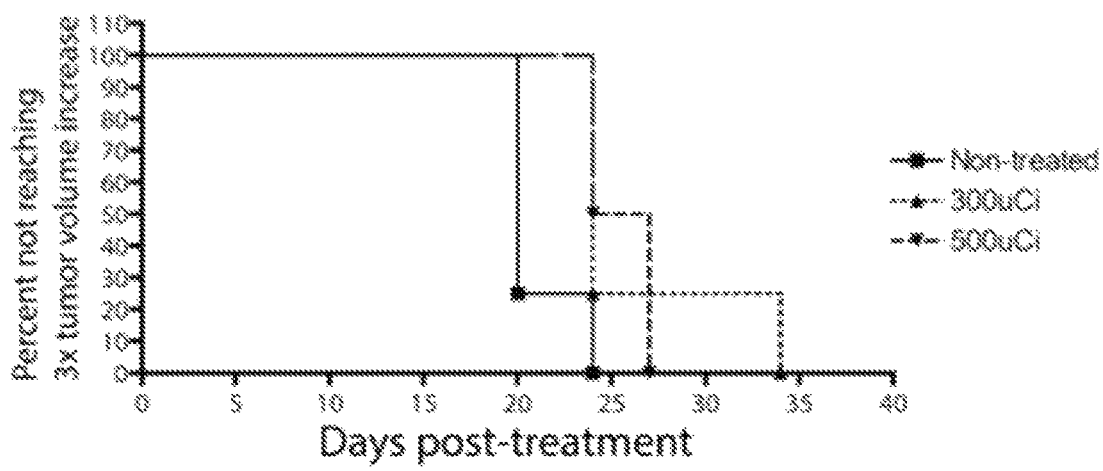

Having thus described the presently disclosed subject matter in general terms, reference will now be made to the accompanying Figures, which are not necessarily drawn to scale, and wherein:

FIG. 1A, FIG. 1B, FIG. 1C, and FIG. 1D show (A) optical imaging agents 1 and 2 reported with dual-targeting moiety to CAIX (Wichert et al., 2015); (B) the epi-fluorescence imaging of two mice harboring CAIX expressing SK-RC-52 tumors within the lower left flank; images were obtained at 1, 2, 4, 6, 8, 11 and 23 h after injection of 3 nmol of compounds 1 and 2 via the tail vein; (C) quantitative biodistribution analysis of compounds 1 and 2; compound accumulations in organs are reported as the percentage of injected dose per gram of tissue (% ID g-1) 24 h after intravenous administration of 3 nmol of 1 and of 2; data points are averages of three mice; error bars indicate standard deviations; and (D) the epi-fluorescence imaging of various organs in a mouse; images were obtained at 24 h after injection of 3 nmol of compound 1 via the tail vein;

FIG. 2A, FIG. 2B, and FIG. 2C show (A) the structure of FITC conjugated fluorescent ligand 8; (B) FACS analysis of 8 for binding to CAIX-negative BxPC3 cells; and (C) FACS analysis of 8 for binding to CAIX-expressing SK-RC-52 cells; flow cytometry was done with 8 at 10 nM, 100 nM and 1 µM with 30 min incubation;

FIG. 3A, FIG. 3B, and FIG. 3C show $IC_{50}$ values of (A) positive control CAIX targeting agent 3; (B) XYIMSR-01; and (C) [$^{113/115}$In]XYIMSR-01; the $IC_{50}$ values were determined relative to the inhibition of fluorescence polarization of FITC labeled 8 with a known $K_d$ of 0.2 nM for CAIX; Compounds 3, XYIMSR-01 and [$^{113/115}$In]XYIMSR-01 demonstrate high binding affinity to CAIX;

FIG. 4A, FIG. 4B, FIG. 4C, and FIG. 4D show binding affinity of (A) 3, (B) [$^{63/65}$Cu]XYIMSR-06, (C) [Al$^{19}$F] XYIMSR-04, and (D) [$^{175}$Lu]XYIMSR-01;

FIG. 5 shows the synthesis scheme for compound 3;

FIG. 6 shows the synthesis scheme for compound XYIMSR-01;

FIG. 7 shows the synthesis scheme for compound XYIMSR-01-[In];

FIG. 8 shows the synthesis scheme for compound XYIMSR-01-[Ga];

FIG. 9 shows the synthesis scheme for compound XYIMSR-01-[Lu];

FIG. 10 shows the synthesis scheme for compound XYIMSR-02;

FIG. 11 shows the synthesis scheme for compound XYIMSR-03;

FIG. 12 shows the synthesis scheme for compound XYIMSR-04;

FIG. 13 shows the synthesis scheme for compound XYIMSR-04-[AlF];

FIG. 14 shows the synthesis scheme for compound XYIMSR-05;

FIG. 15 shows the synthesis scheme for compound XYIMSR-06;

FIG. 16 shows the synthesis scheme for compound XYIMSR-06-Cu;

FIG. 17 shows the SPECT/CT imaging of two mice harboring CAIX-expressing SK-RC-52 tumors within the lower left flank; images were obtained at 1, 4, 8, 24 and 48 h after injection of 14.8 MBq (400 µCi) of [$^{111}$In]XYIMSR-01 via the tail vein; arrows indicate tumors; [$^{111}$In]XYIMSR-01 enabled specific imaging of CAIX-expressing SK-RC-52 tumors;

FIG. 18 shows the SPECT/CT imaging of two mice harboring CAIX-expressing SK-RC-52 tumors within the lower left flank; images were obtained at 1, 4, 8, 24 and 48 h after injection of 740 kBq (20 µCi) of [$^{177}$Lu]XYIMSR-01 via the tail vein; arrows indicate tumors;

FIG. 19 shows the PET/CT imaging of [Al$^{18}$F]XYIMSR-04 in mice harboring CAIX-expressing SK-RC-52 tumors within the lower left flank; images were obtained at 1 h after injection of 7.4 MBq (200 µCi) of [Al$^{18}$F]XYIMSR-04 via the tail vein;

FIG. 20 shows PET/CT imaging of [$^{64}$Cu]XYIMSR-06 in mice harboring CAIX-expressing SK-RC-52 tumors within the upper right flank; images were obtained at 1 h after injection of 22.2 MBq (600 µCi) of [$^{64}$Cu]XYIMSR-06 via the tail vein; arrows indicate tumors; and FIG. 21 shows the treatment response of [$^{177}$Lu]XYIMSR-01 in SK-RC-52 tumor mice.

The patent or application file contains at least one drawing executed in color. Copies of this patent or patent application publication with color drawings will be provided by the Office upon request and payment of the necessary fee.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. Nuclear Imaging and Radiotherapeutics Agents Targeting Carbonic Anhydrase IX and Uses Thereof A. Compounds of Formula (I)

Accordingly, in some embodiments, the presently disclosed subject matter provides a compound of formula (I):

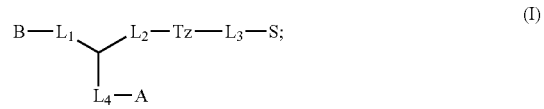

wherein: B is a metal chelating moiety optionally comprising a metal or a radiometal, or a halogenated or radiohalogenated prosthetic group; $L_1$, $L_2$, $L_3$, and $L_4$ are —$C_1$-$C_{24}$ alkyl-, wherein each alkyl group is optionally substituted with one to four groups selected from the group consisting of =O, =S, and —COOR and one to six of the methylene groups in each alkyl group is optionally replaced by —O—, —S—, or —(NR')—, provided that no two adjacent methylene groups are both replaced by —O—, —S—, or —(NR')—; each R and R' is independently selected from the group consisting of hydrogen, $C_1$-$C_6$ alkyl, $C_2$-$C_{12}$ aryl, and $C_4$-$C_{16}$ alkyl aryl; Tz is a triazole group selected from the group consisting of

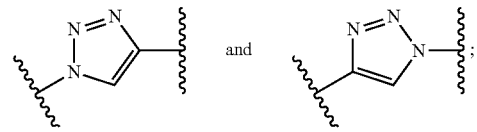 [SMILES: *c1cn(*)nn1 ; *c1cn(*)nn1]

S is a sulfonamide selected from the group consisting of:

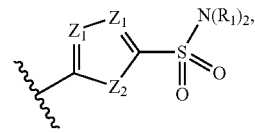

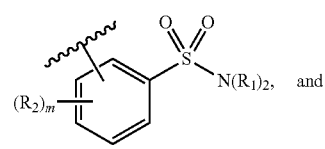

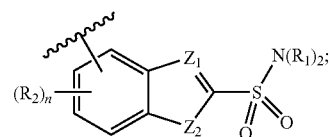

each $R_1$ is independently selected from the group consisting of hydrogen, substituted or unsubstituted alkyl, substituted and unsubstituted aryl, and substituted and unsubstituted heteroaryl; each $R_2$ is selected from the group consisting of hydrogen, halogen, hydroxyl, alkoxyl, —CN, —$CF_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; m is an integer selected from the group consisting of 1, 2, 3, and 4; n is an integer selected from the group consisting of 1, 2, and 3; each $Z_1$ is independently selected from the group consisting of $CR_3$, and N; each $Z_2$ is independently selected from the group consisting of $CR_3$, and S; each $R_3$ is independently selected from the group consisting of hydrogen, halogen, hydroxyl, alkoxyl, —CN, —$CF_3$, amino, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; A is

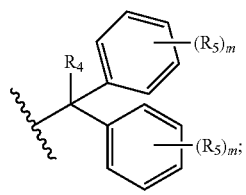

$R_4$ is independently selected from the group consisting of hydrogen, hydroxyl, alkoxyl, substituted or unsubstituted alkyl, substituted or unsubstituted alkenyl, and substituted or unsubstituted alkynyl; $R_5$ is independently selected from the group consisting of hydrogen, halogen, hydroxyl, alkoxyl, —CN, —$CF_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; or a pharmaceutically acceptable salt thereof.

In particular embodiments, the compound of formula (I) is a compound of formula (II):

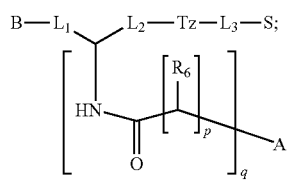

wherein: p is an integer selected from the group consisting of 0, 1, 2, 3, and 4; q is an integer selected from the group consisting of 1, 2, 3, and 4; each $R_6$ is independently selected from the group consisting of H and —COOR; or a pharmaceutically acceptable salt thereof.

In further embodiments, the compound of formula (II) is a compound of formula (III):

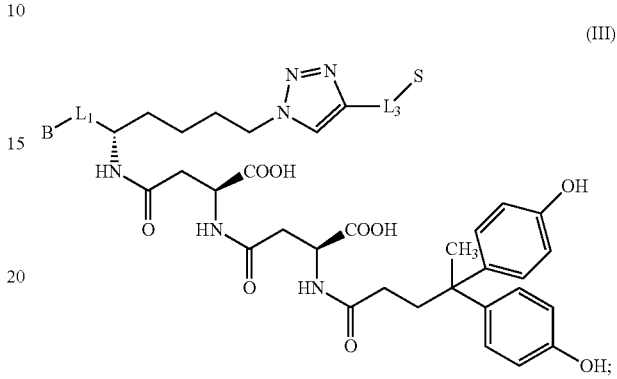

or a pharmaceutically acceptable salt thereof.

In yet further embodiments, S is selected from the group consisting of:

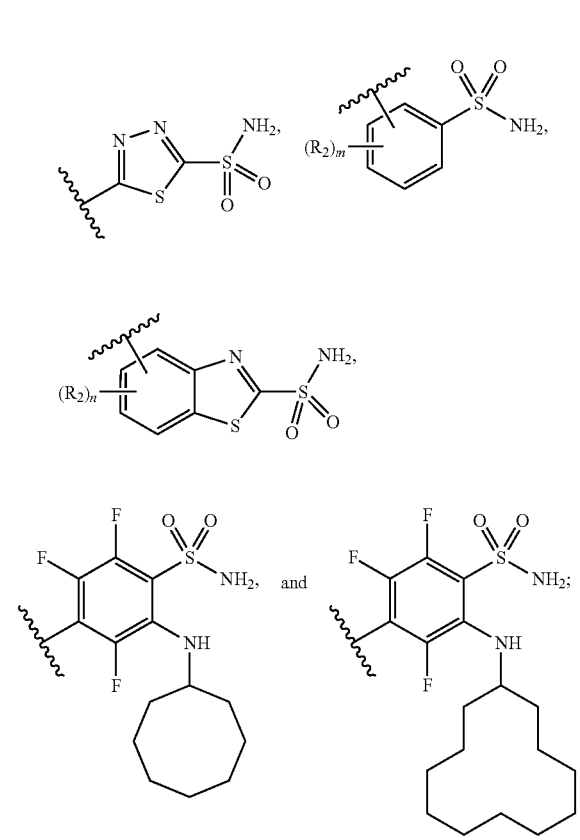

or a pharmaceutically acceptable salt thereof.

In particular embodiments, B is a metal chelating moiety optionally comprising a metal or a radiometal selected from the group of:

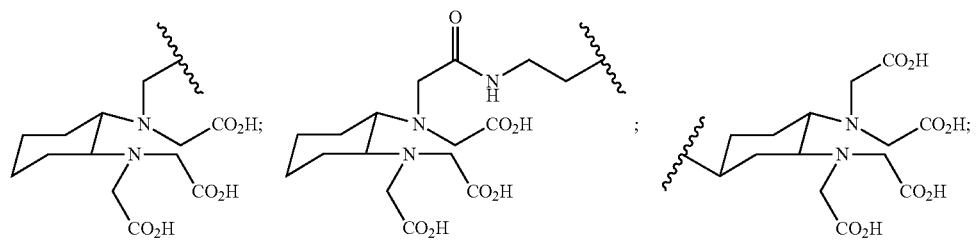
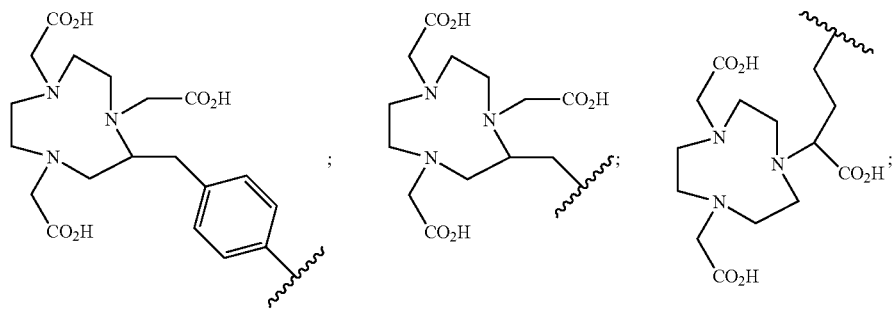
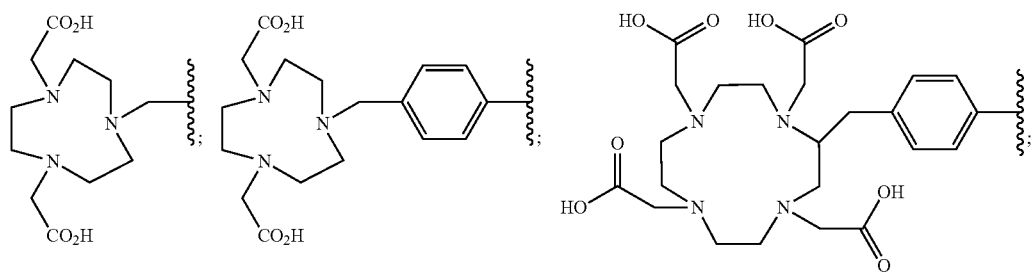
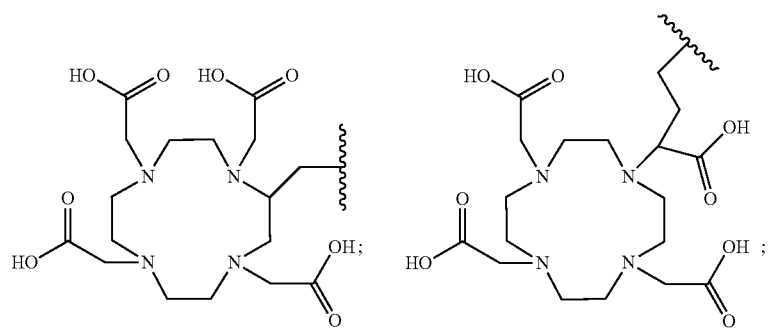
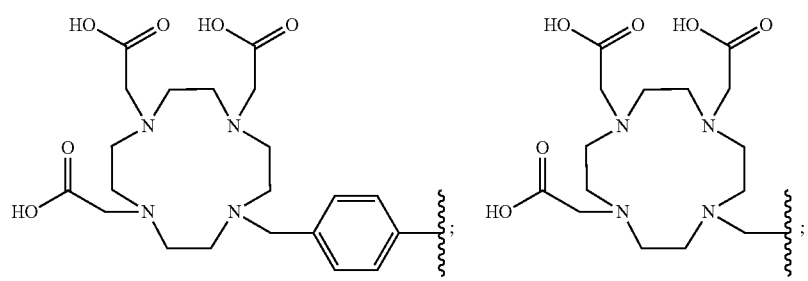

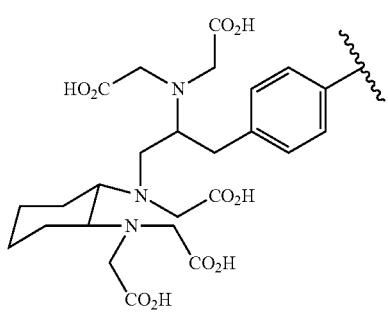
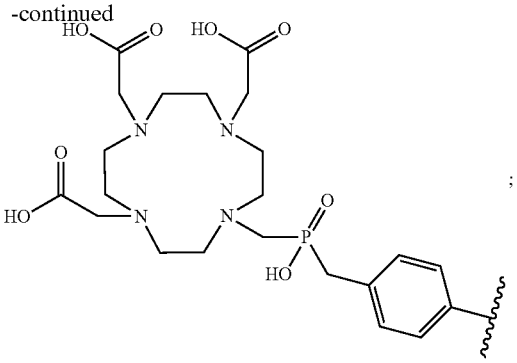
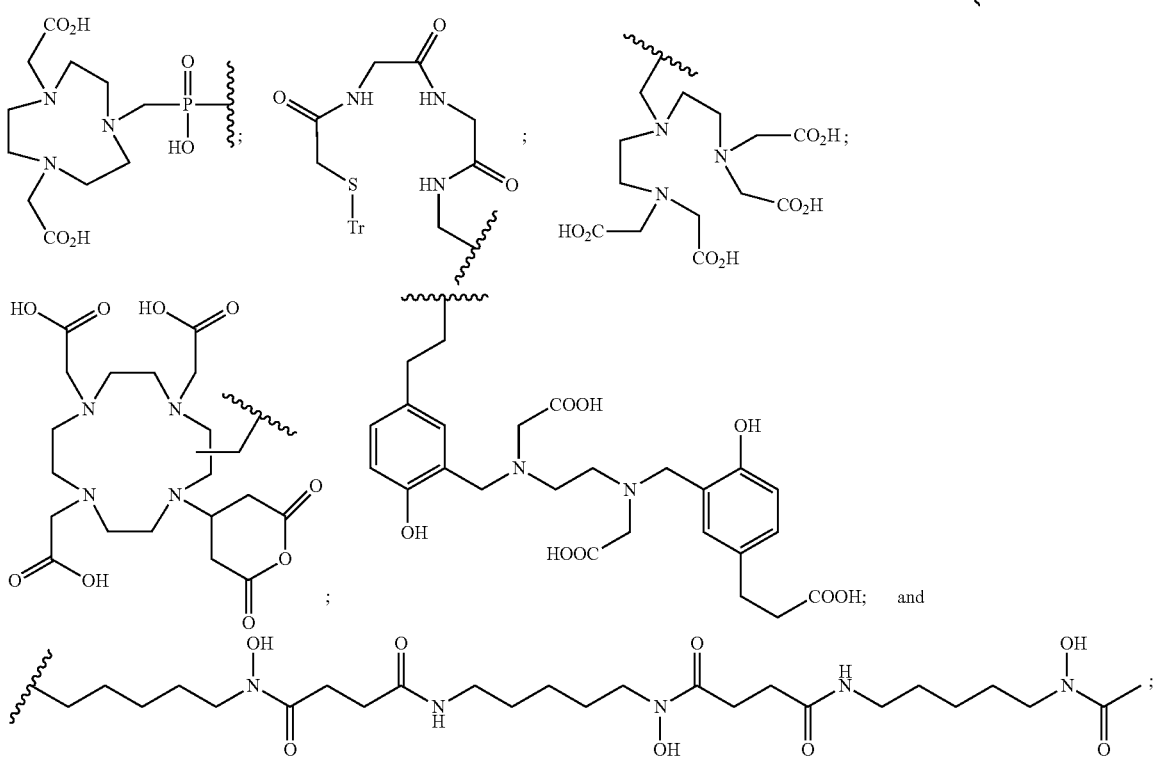
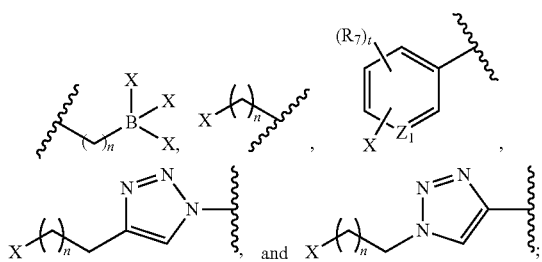

or B is a halogenated or radio-halogenated prosthetic group selected from the group consisting of:

wherein: X is a halogen or a radio-halogen; n is an integer selected from the group consisting of 1, 2, 3, 4, 5 and 6; t is an integer selected from the group consisting of 1, 2, and 3; each $R_7$ is selected from the group consisting of hydrogen, halogen, hydroxyl, alkoxyl, —CN, —CF$_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; or a pharmaceutically acceptable salt thereof.

In certain embodiments, the metal chelating agent comprises a metal selected from the group consisting of: Y, Lu, Tc, Zr, In, Sm, Re, Cu, Pb, Ac, Bi, Al, Ga, Re, Ho and Sc. In other embodiments, the metal is a radiometal and is selected from the group consisting of $^{67}$Ga, $^{68}$Ga, $^{64}$Cu, $^{67}$Cu, Al-$^{18}$F, $^{86}$Y, $^{90}$Y, $^{89}$Zr, $^{111}$In, $^{99m}$Tc, $^{177}$Lu, $^{153}$Sm, $^{186}$Re, $^{188}$Re, $^{203}$Pb, $^{212}$Pb, $^{225}$Ac, $^{212}$Bi, $^{213}$Bi, $^{47}$Sc, and $^{166}$Ho.

In further embodiments, halogen is selected from the group consisting of: F, Br, I, and At. In yet further embodiments, the radio-halogen is selected from the group consisting of: $^{18}$F, $^{76}$Br, $^{77}$Br, $^{80m}$Br, $^{125}$I, $^{124}$I, $^{131}$I, $^{211}$At.

In certain embodiments, the compound of Formula (I) is selected from the group consisting of:

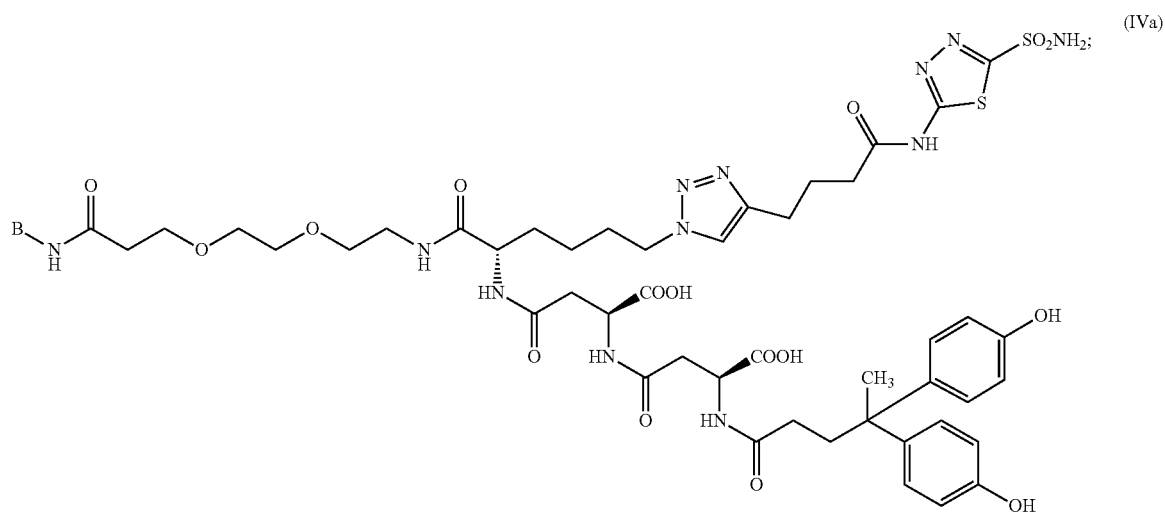
(IVa)
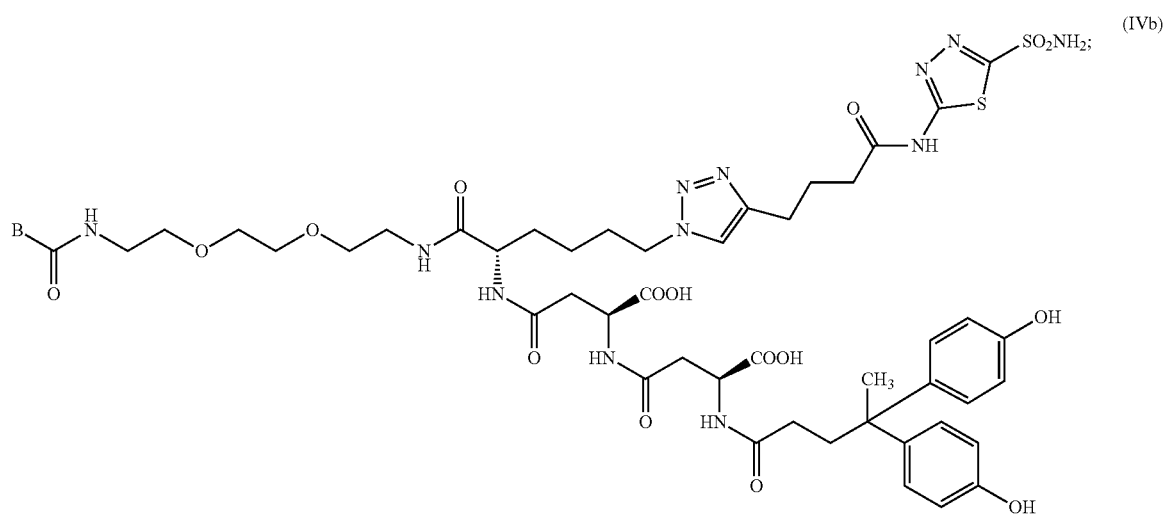
(IVb)
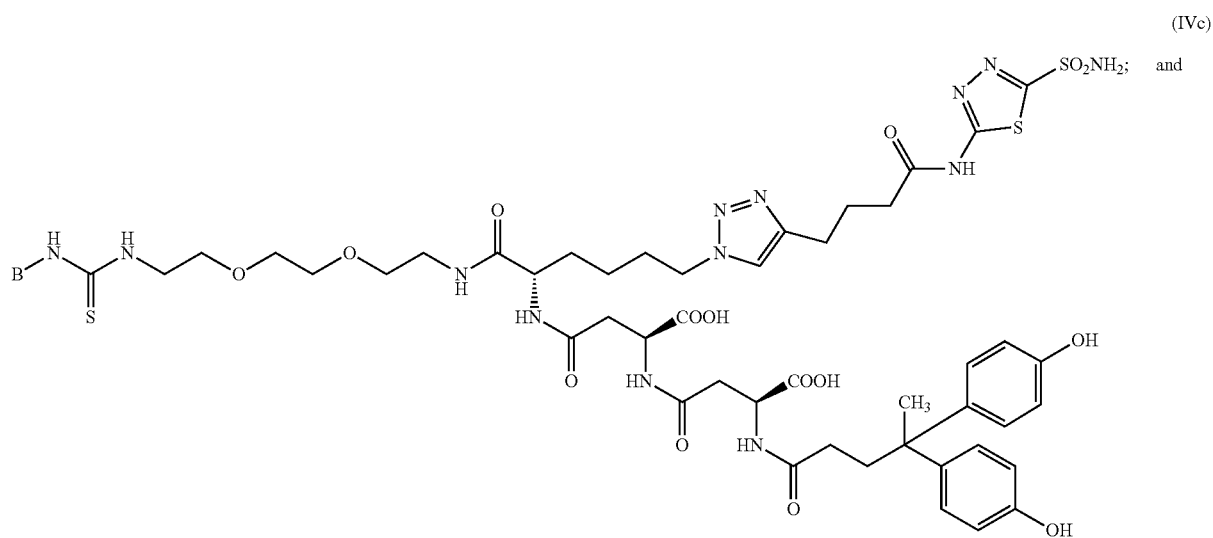
(IVc) and

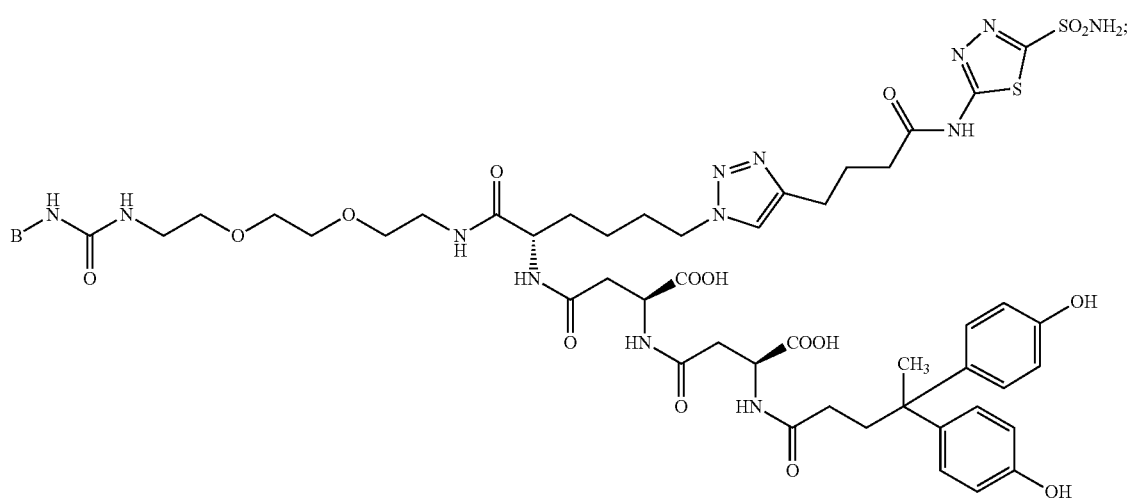
or a pharmaceutically acceptable salt thereof.
In particular embodiments, the compound of Formula (I) is selected from the group consisting of:
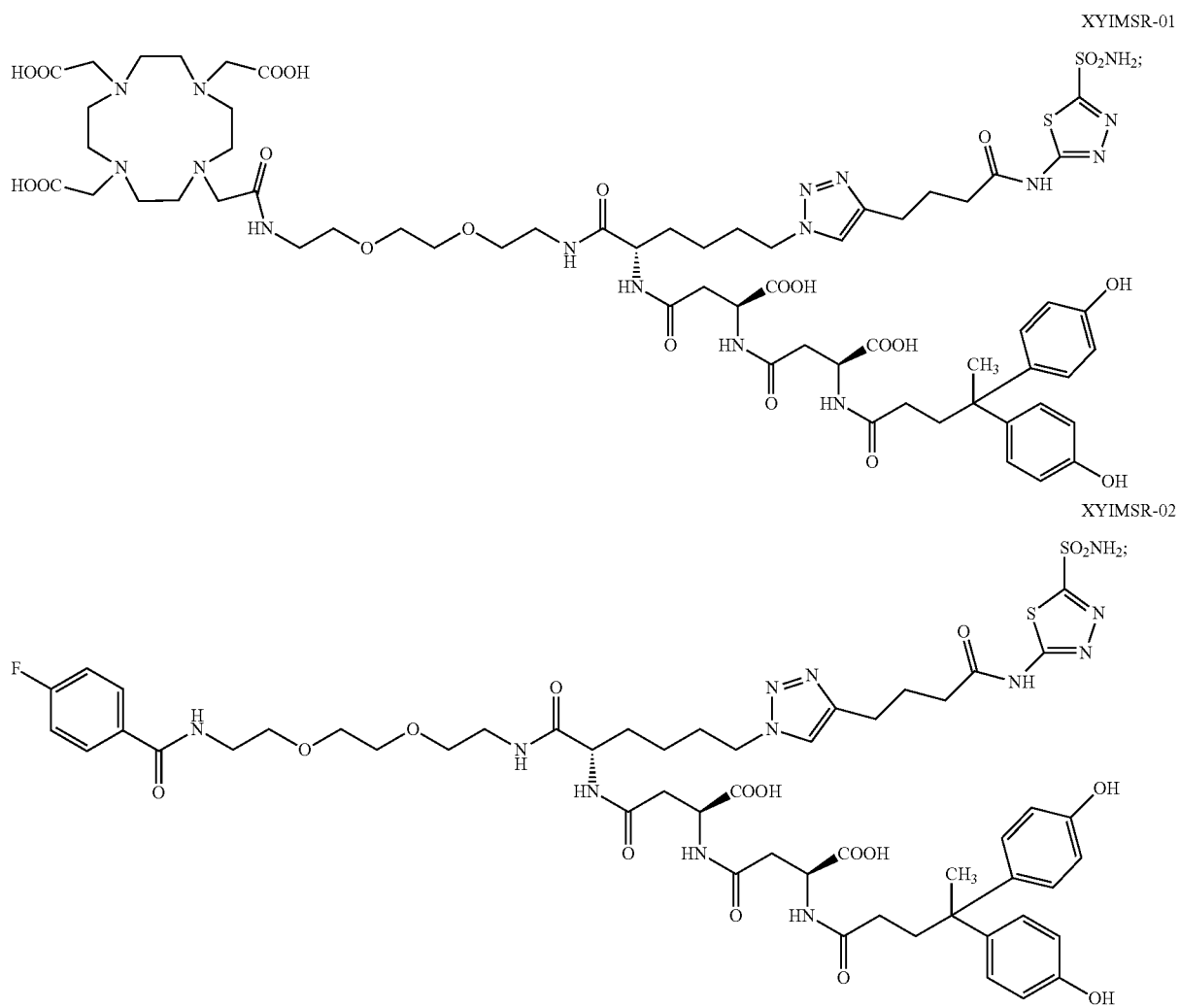

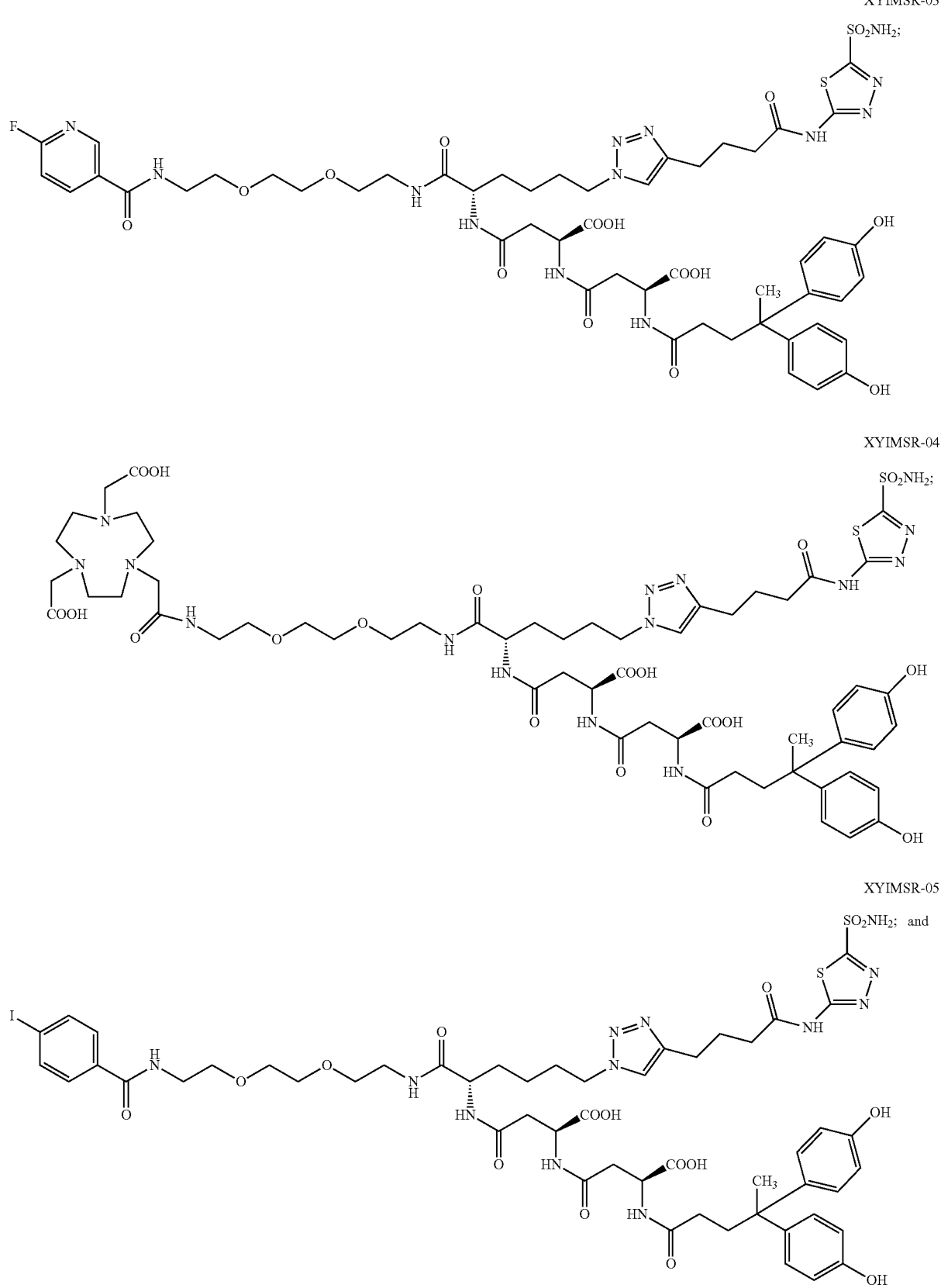

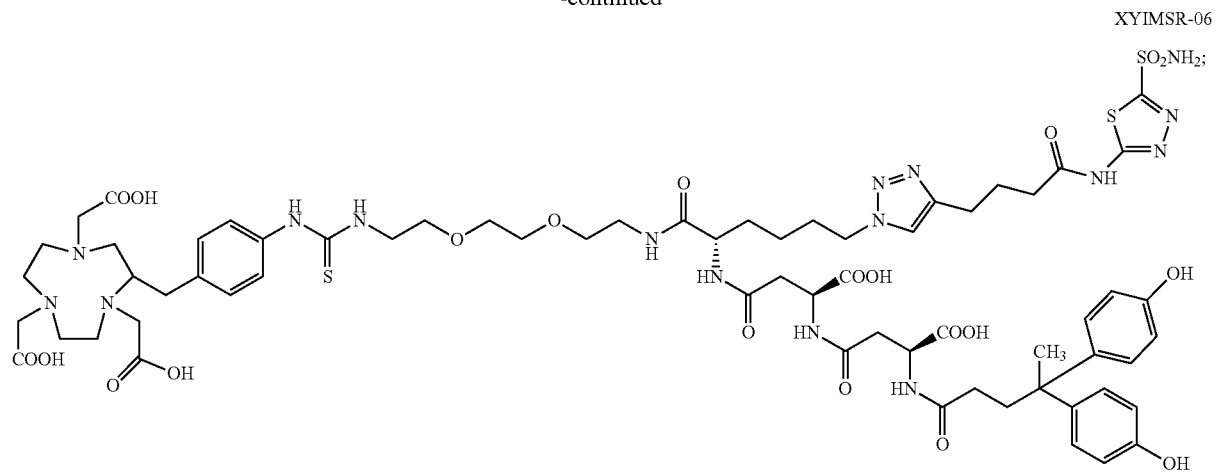
XYIMSR-06
or a pharmaceutically acceptable salt thereof.
In other particular embodiments, the compound of formula (I) is selected from the group consisting of:
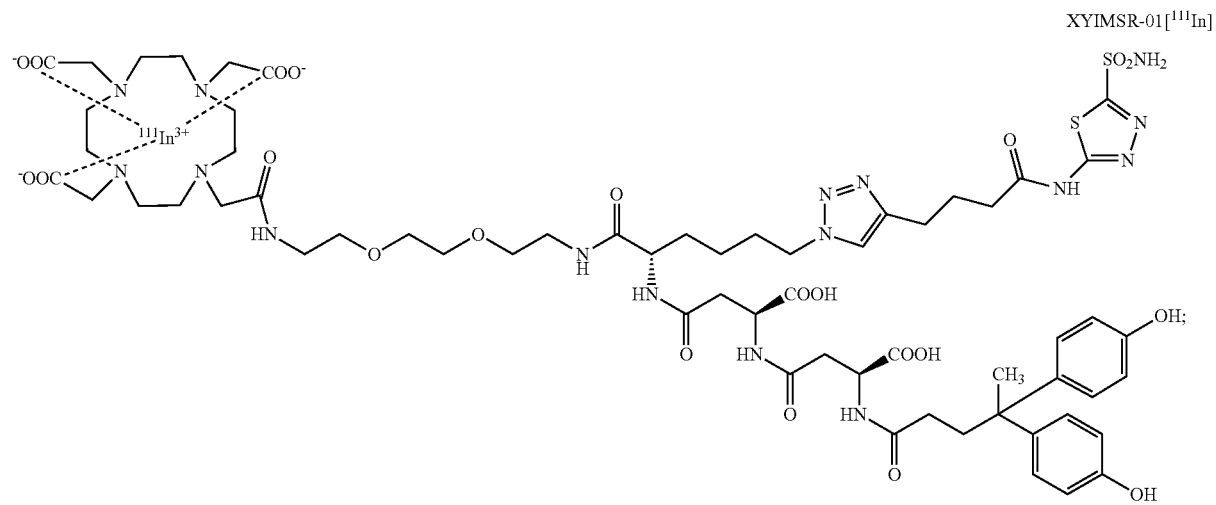
XYIMSR-01[$^{111}$In]
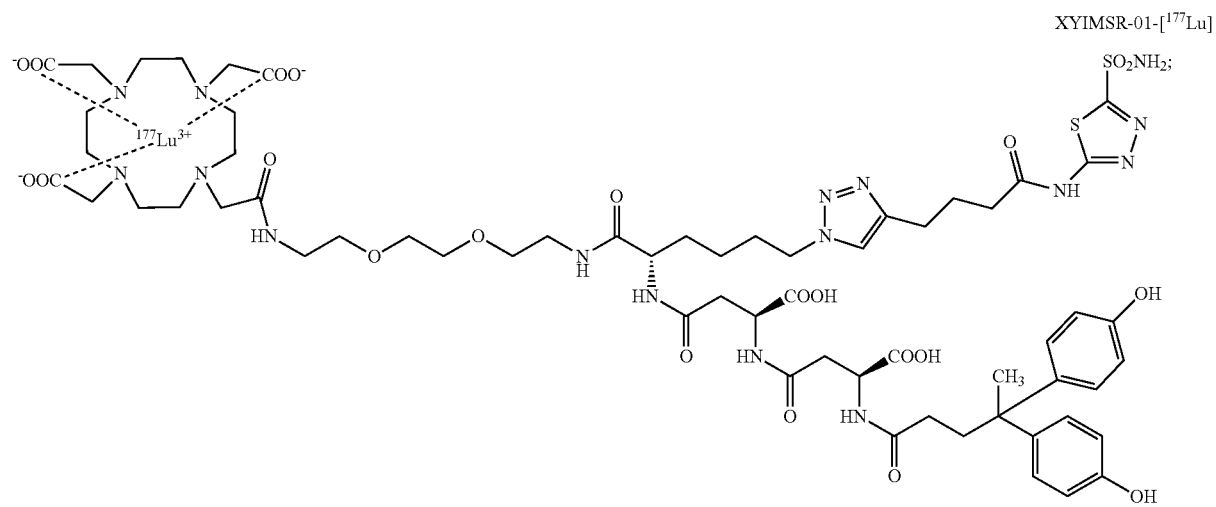
XYIMSR-01-[$^{177}$Lu]

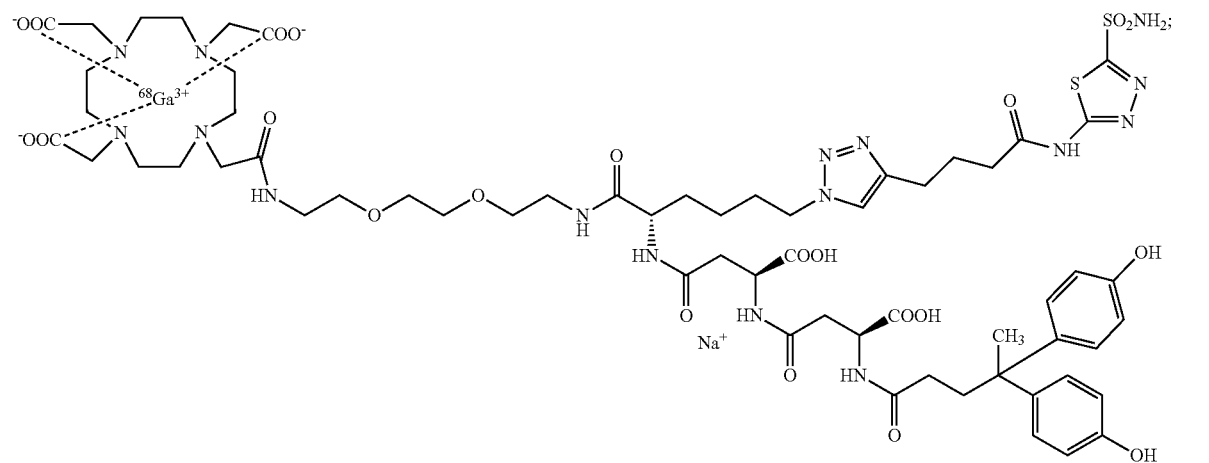
XYIMSR-01-[68Ga]
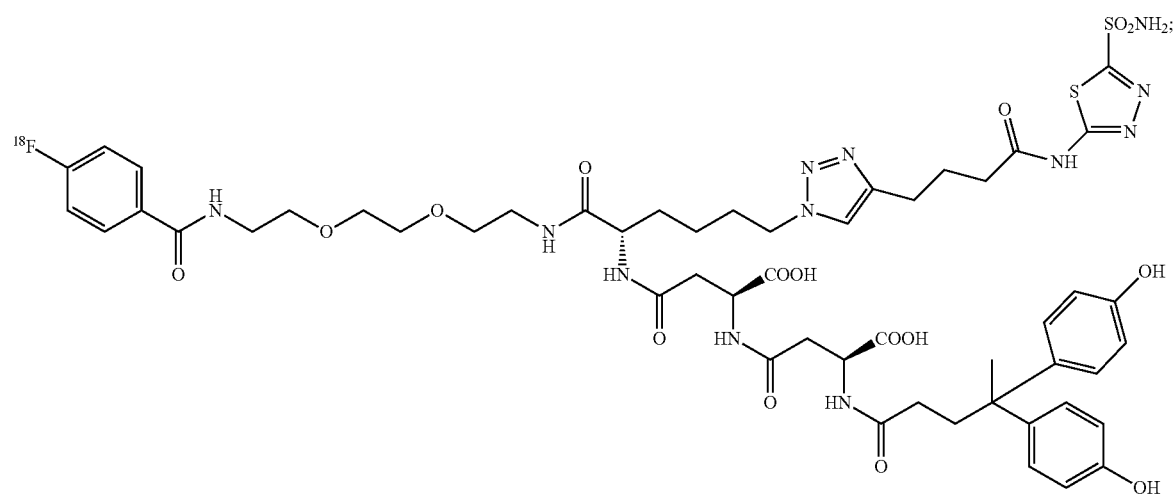
XYIMSR-02-[18F]
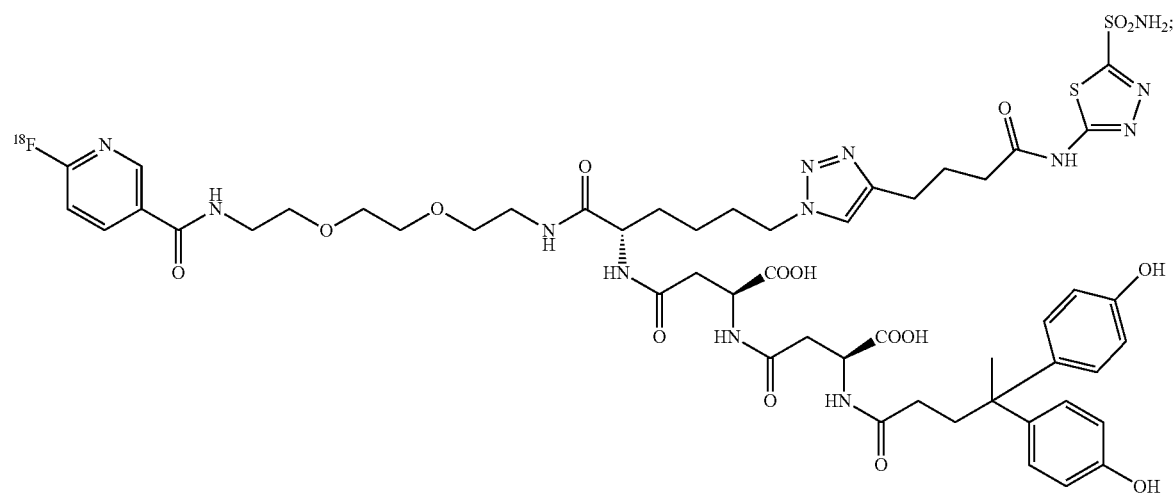
XYIMSR-03-[18F]

-continued
XYIMSR-04-[Al$^{18}$F]
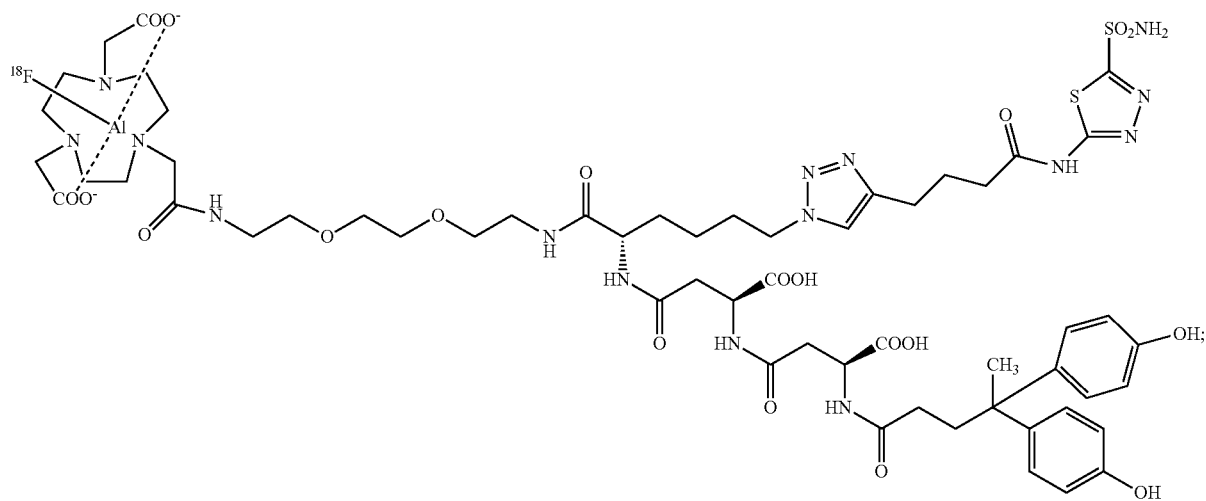
XYIMSR-05-[$^{124}$I]
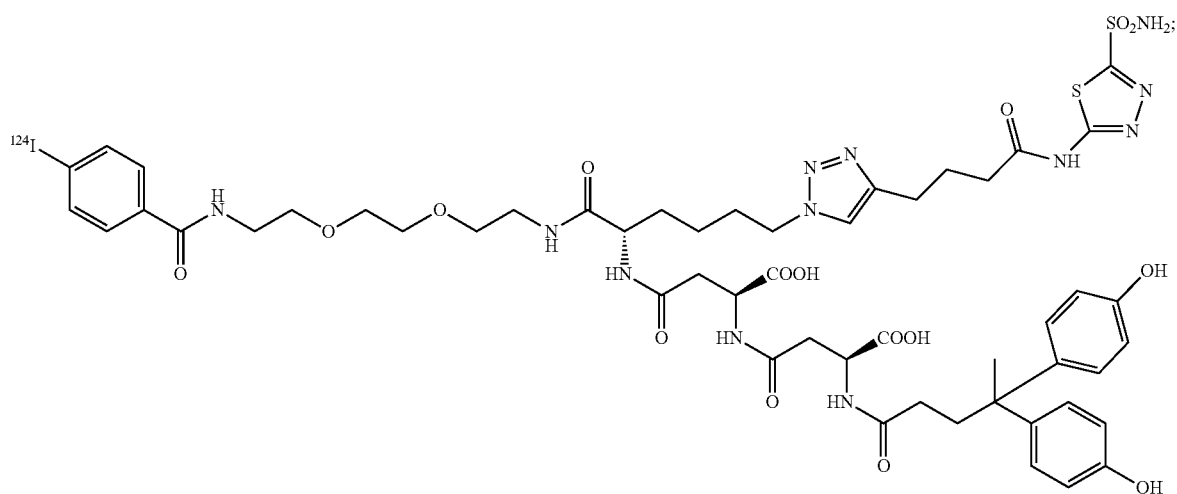
XYIMSR-05-[$^{125}$I]
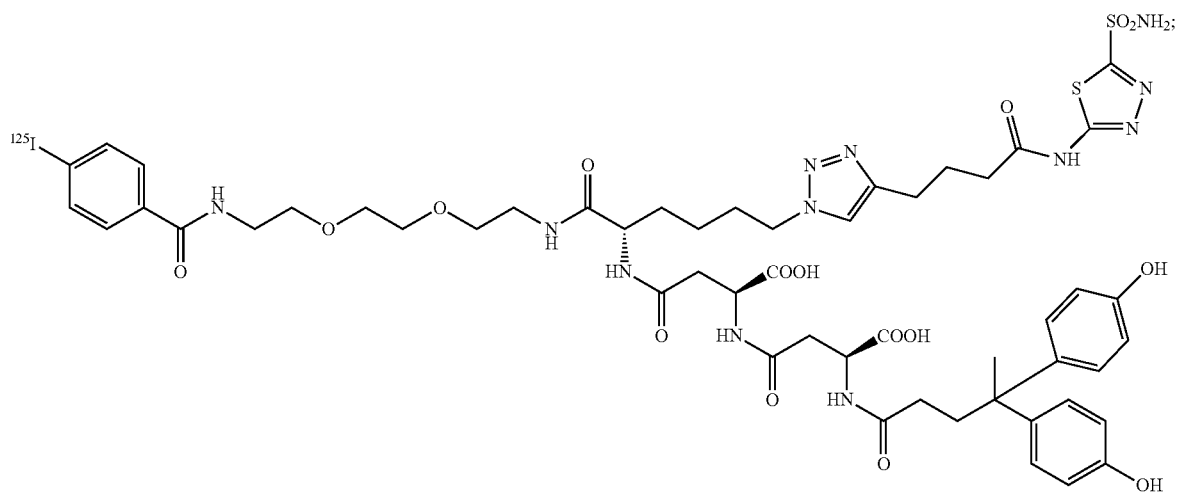

-continued

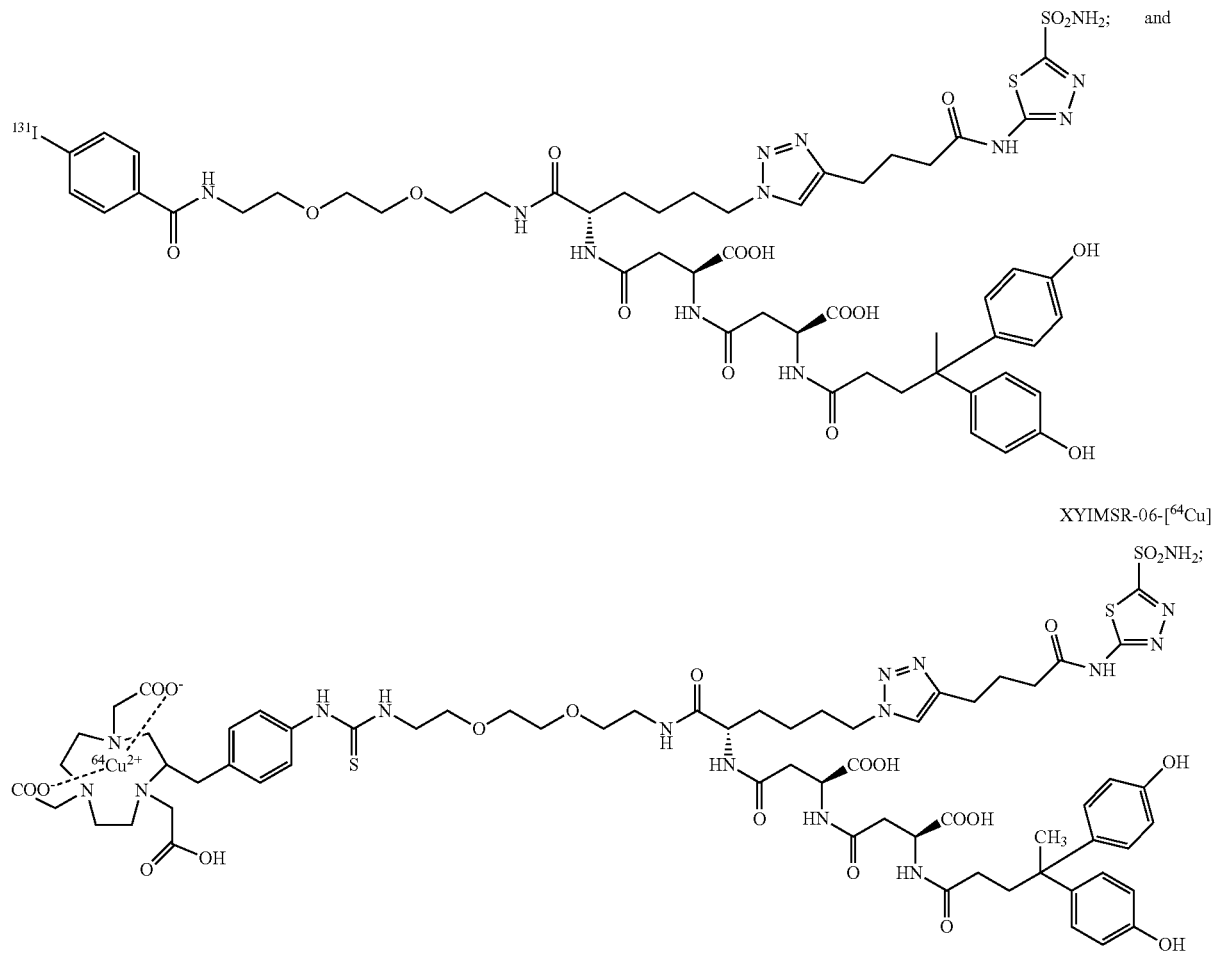

or a pharmaceutically acceptable salt thereof.

B. Methods of Using Compounds of Formula (I) for Imaging or Treating a Carbonic Anhydrase IX-Expressing Tumor or Cell Accordingly, in some embodiments, the presently disclosed subject matter provides a method for imaging or treating one or more Carbonic Anhydrase IX expressing tumors or cells, the method comprising contacting the one or more tumors or cells with an effective amount of a compound of formula (I) and making an image, the compound of formula (I) comprising:

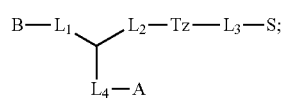
(I)

wherein: B is a metal chelating moiety comprising a radiometal, or a radio-halogenated prosthetic group; $L_1$, $L_2$, $L_3$, and $L_4$ are —$C_1$-$C_{24}$ alkyl-, wherein each alkyl group is optionally substituted with one to four groups selected from the group consisting of =O, =S, and —COOR and one to six of the methylene groups in each alkyl group is optionally replaced by —O—, —S—, or —(NR')—, provided that no two adjacent methylene groups are both replaced by —O—, —S—, or —(NR')—; each R and R' is independently selected from the group consisting of hydrogen, $C_1$-$C_6$ alkyl, $C_2$-$C_{12}$ aryl, and $C_4$-$C_{16}$ alkyl aryl; Tz is a triazole group selected from the group consisting of

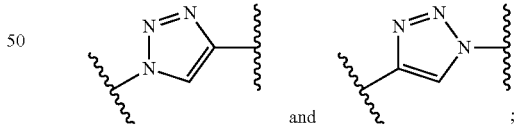

S is a sulfonamide targeting a catalytic pocket of CAIX selected from the group consisting of:

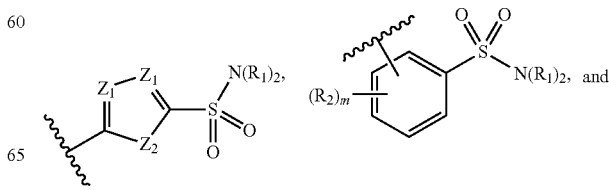

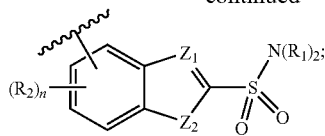

each $R_1$ is independently selected from the group consisting of hydrogen, substituted or unsubstituted alkyl, substituted and unsubstituted aryl, and substituted and unsubstituted heteroaryl; each $R_2$ is selected from the group consisting of hydrogen, halogen, hydroxyl, alkoxyl, —CN, —$CF_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; m is an integer selected from the group consisting of 1, 2, 3, and 4; n is an integer selected from the group consisting of 1, 2, and 3; each $Z_1$ is independently selected from the group consisting of $CR_3$, and N; each $Z_2$ is independently selected from the group consisting of $CR_3$, and S; each $R_3$ is independently selected from the group consisting of hydrogen, halogen, hydroxyl, alkoxyl, —CN, —$CF_3$, amino, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; A is

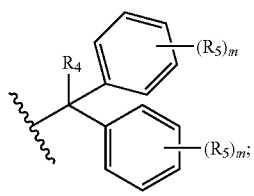

$R_4$ is independently selected from the group consisting of hydrogen, hydroxyl, alkoxyl, substituted or unsubstituted alkyl, substituted or unsubstituted alkenyl, and substituted or unsubstituted alkynyl; $R_5$ is independently selected from the group consisting hydrogen, halogen, hydroxyl, alkoxyl, —CN, —$CF_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; or a pharmaceutically acceptable salt thereof.

In particular embodiments, the compound of formula (I) is a compound of formula (II):

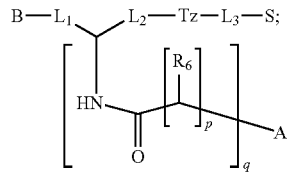

wherein: p is an integer selected from the group consisting of 0, 1, 2, 3, and 4; q is an integer selected from the group consisting of 1, 2, 3, and 4; each $R_6$ is independently selected from the group consisting of H and —COOR; or a pharmaceutically acceptable salt thereof.

In further embodiments, the compound of formula (II) is a compound of formula (III):

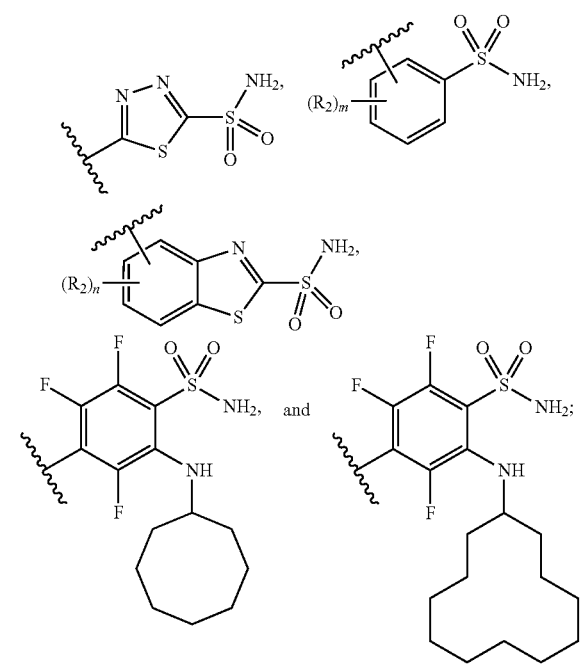

or a pharmaceutically acceptable salt thereof.

In yet further embodiments, S is selected from the group consisting of:

or a pharmaceutically acceptable salt thereof.

In particular embodiments, B is a metal chelating moiety comprising a radiometal selected from the group of:

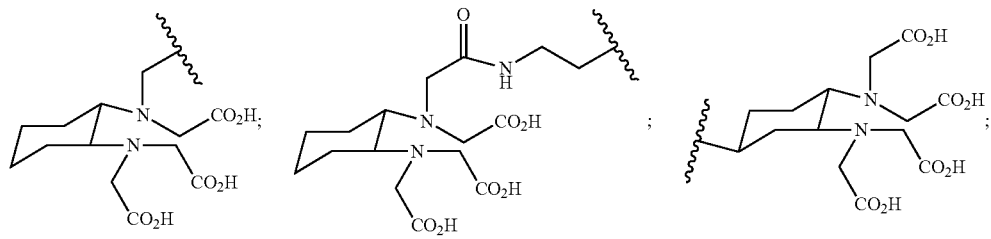
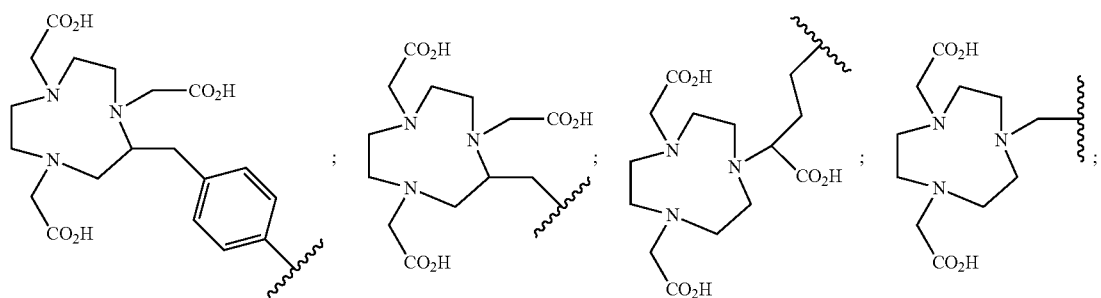
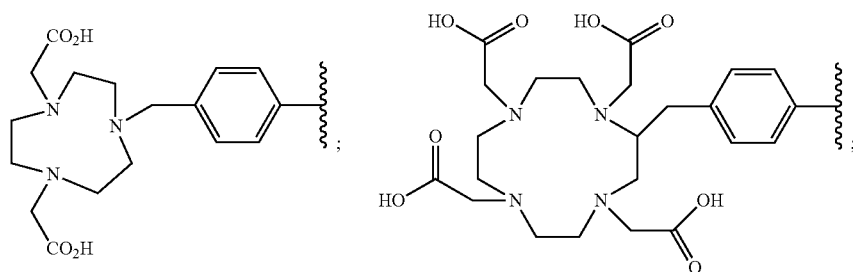
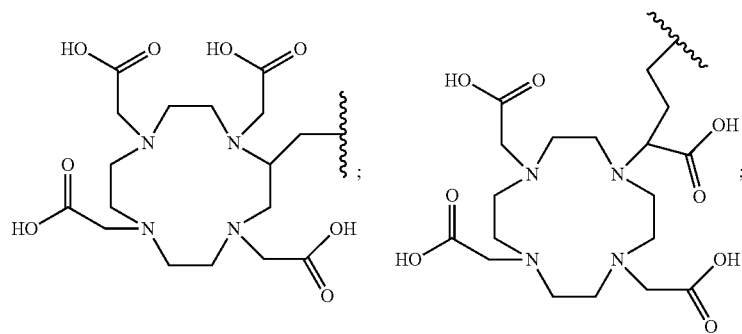
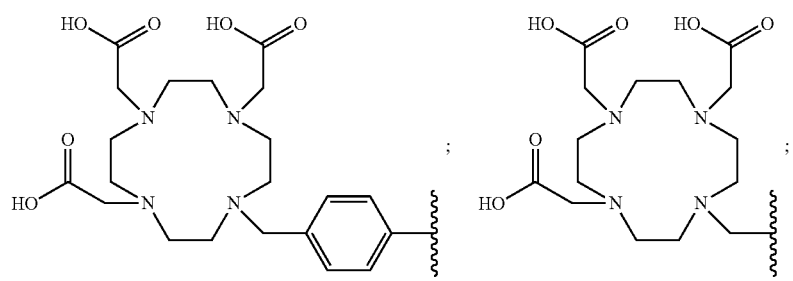

-continued

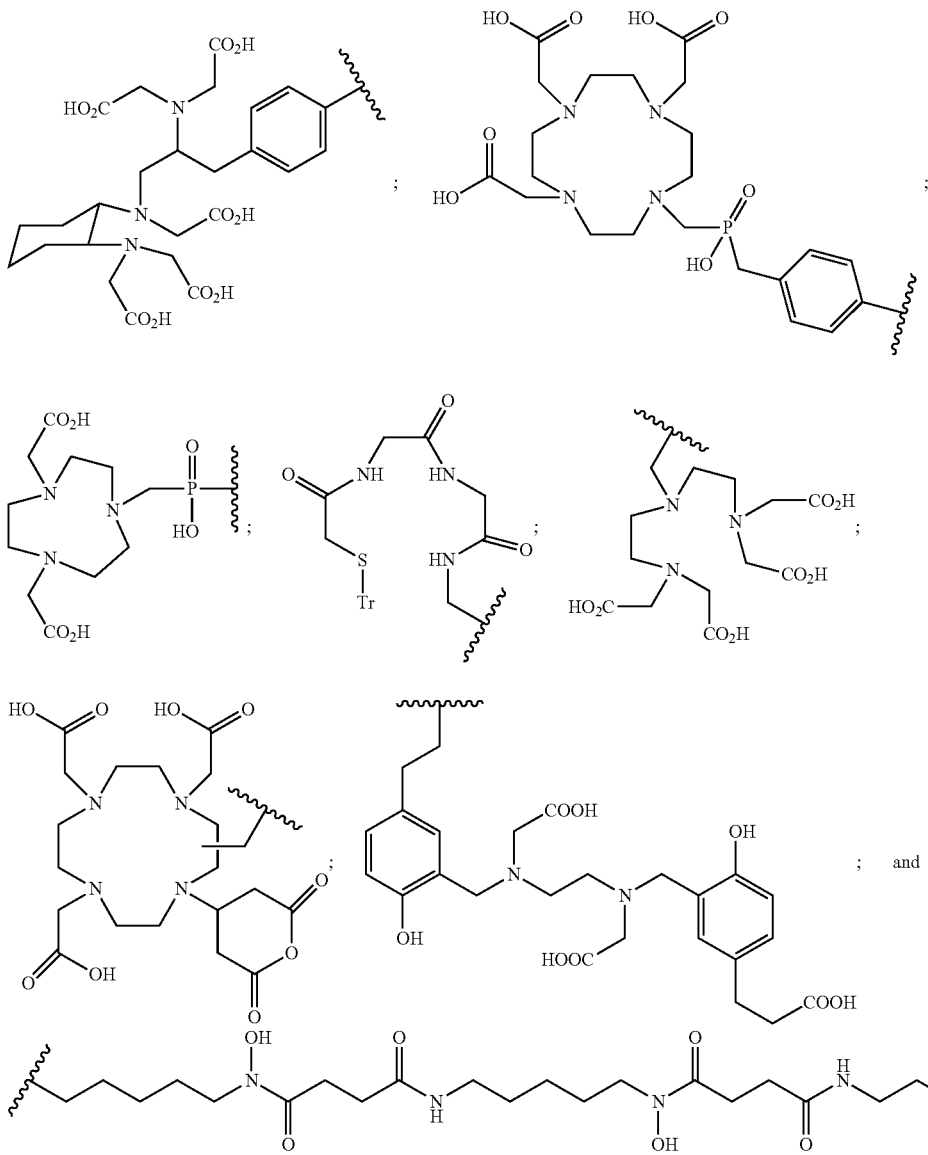

or B is a radio-halogenated prosthetic group selected from the group consisting of:

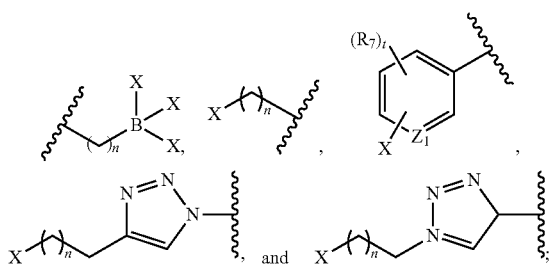

wherein: X is a radio-halogen; n is an integer selected from the group consisting of 1, 2, 3, 4, 5 and 6; t is an integer selected from the group consisting of 1, 2, and 3; each $R_7$ is selected from the group consisting of hydrogen, halogen, hydroxyl, alkoxyl, —CN, —$CF_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl; or a pharmaceutically acceptable salt thereof.

In certain embodiments, the radiometal is selected from the group consisting of $^{67}Ga$, $^{68}Ga$, $^{64}Cu$, $^{67}Cu$, Al-$^{18}F$, $^{86}Y$, $^{90}Y$, $^{89}Zr$, $^{111}In$, $^{99m}Tc$, $^{177}Lu$, $^{153}Sm$, $^{186}Re$, $^{188}Re$, $^{203}Pb$, $^{212}Pb$, $^{225}Ac$, $^{212}Bi$, $^{213}Bi$, $^{47}Sc$, and $^{166}Ho$.

In other embodiments, the radio-halogen is selected from the group consisting of $^{18}F$, $^{76}Br$, $^{77}Br$, $^{80m}Br$, $^{125}I$, $^{124}I$, $^{131}I$, $^{211}At$.

In certain embodiments, the compound of Formula (I) is selected from the group consisting of:

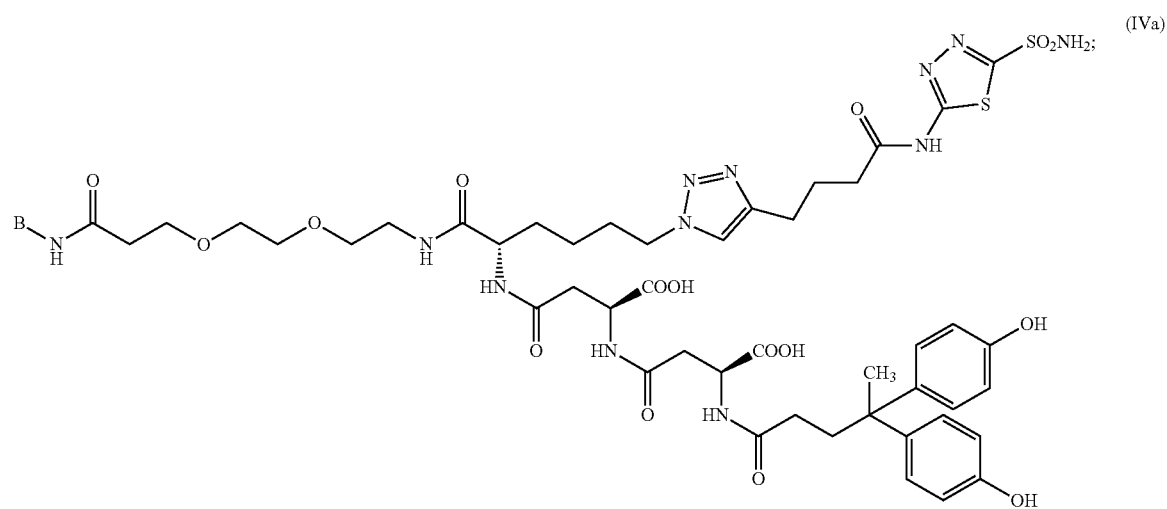
(IVa)
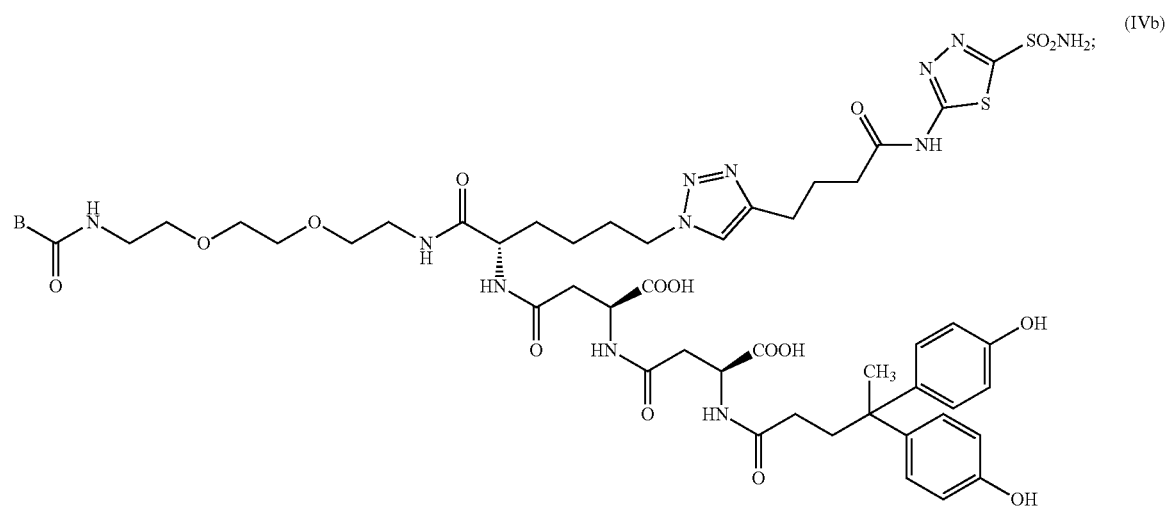
(IVb)
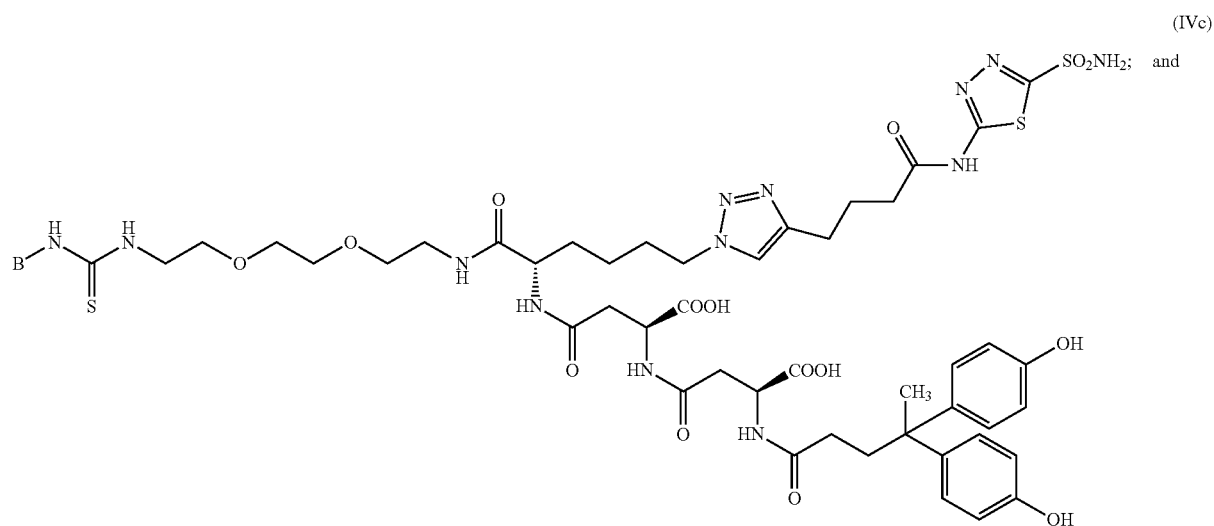
(IVc) and

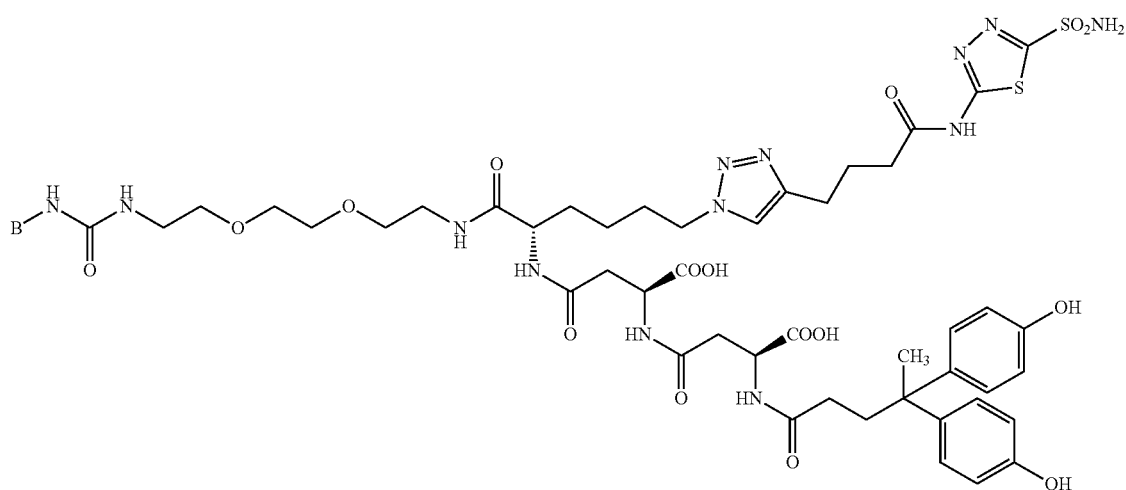
or a pharmaceutically acceptable salt thereof.
In particular embodiments, the compound of Formula (I) is selected from the group consisting of:
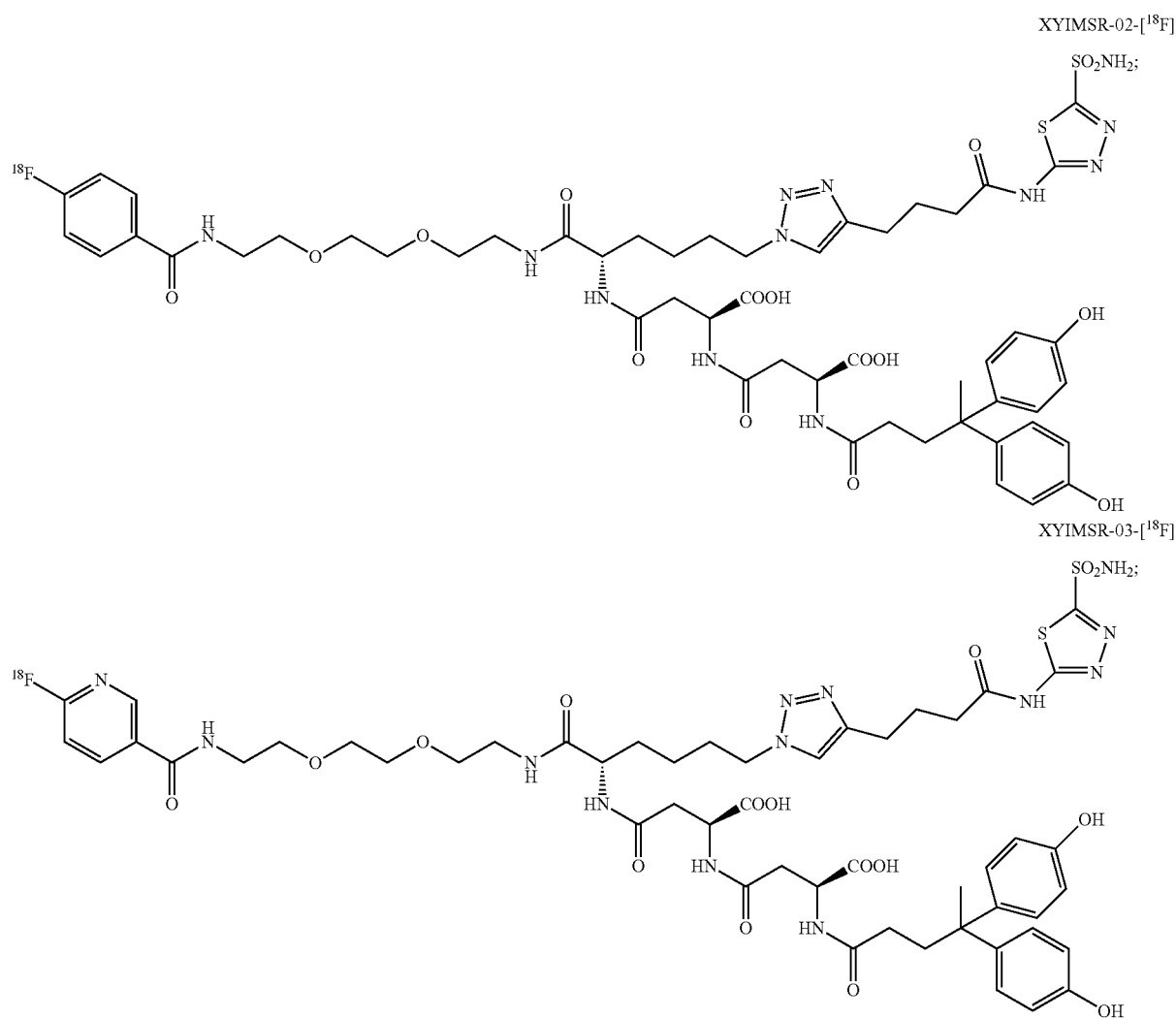

XYIMSR-05-[$^{124}$I]
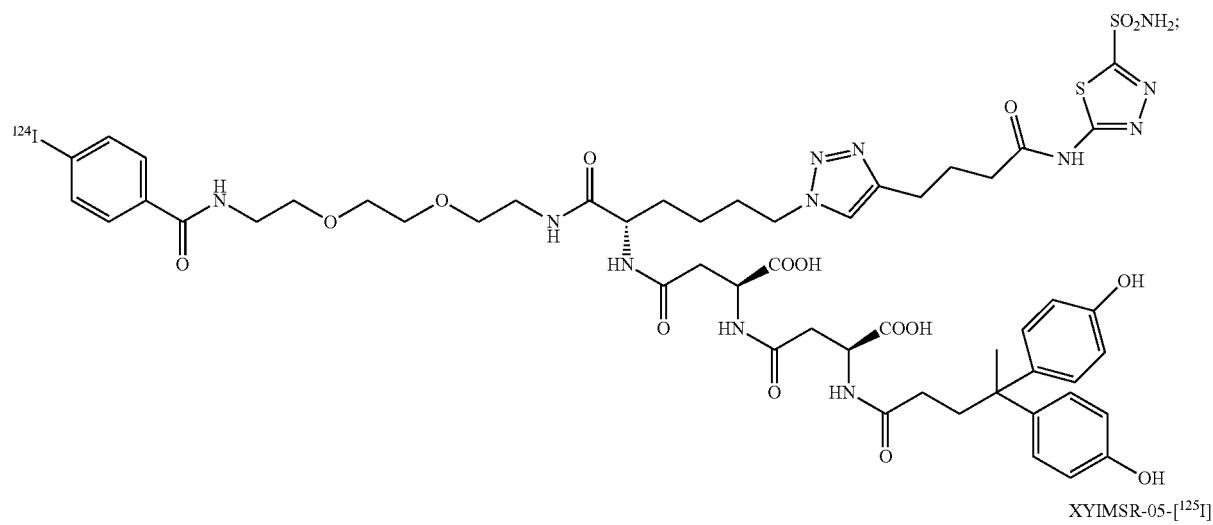
XYIMSR-05-[$^{125}$I]
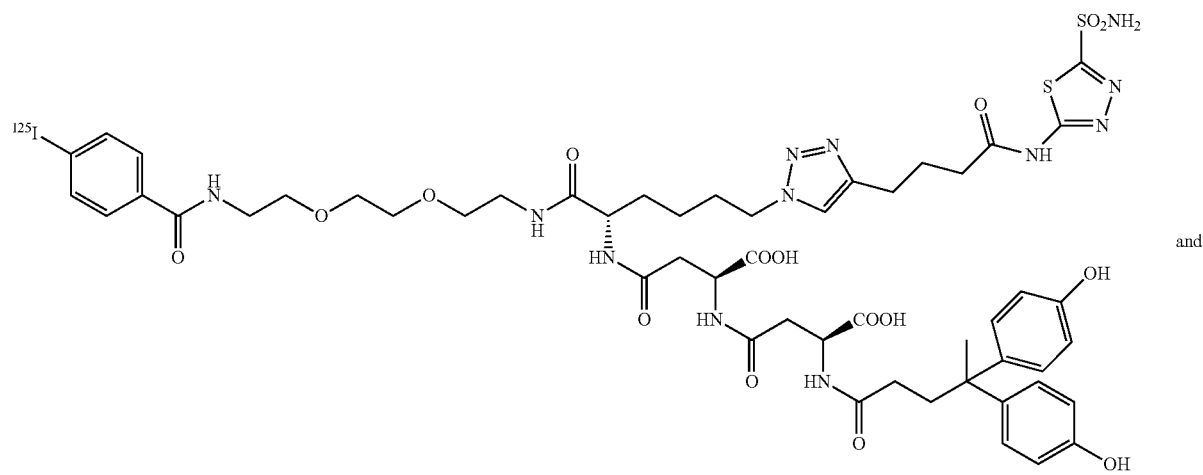
and
XYIMSR-05-[$^{131}$I]
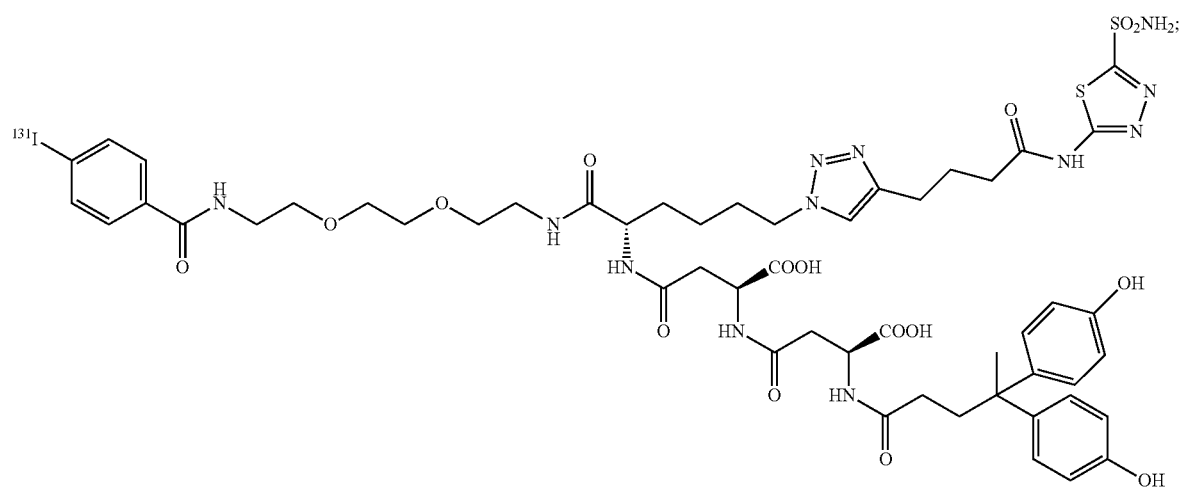
or a pharmaceutically acceptable salt thereof.
In other particular embodiments, the compound of formula (I) is selected from the group consisting of:

XYIMSR-01-[111In]
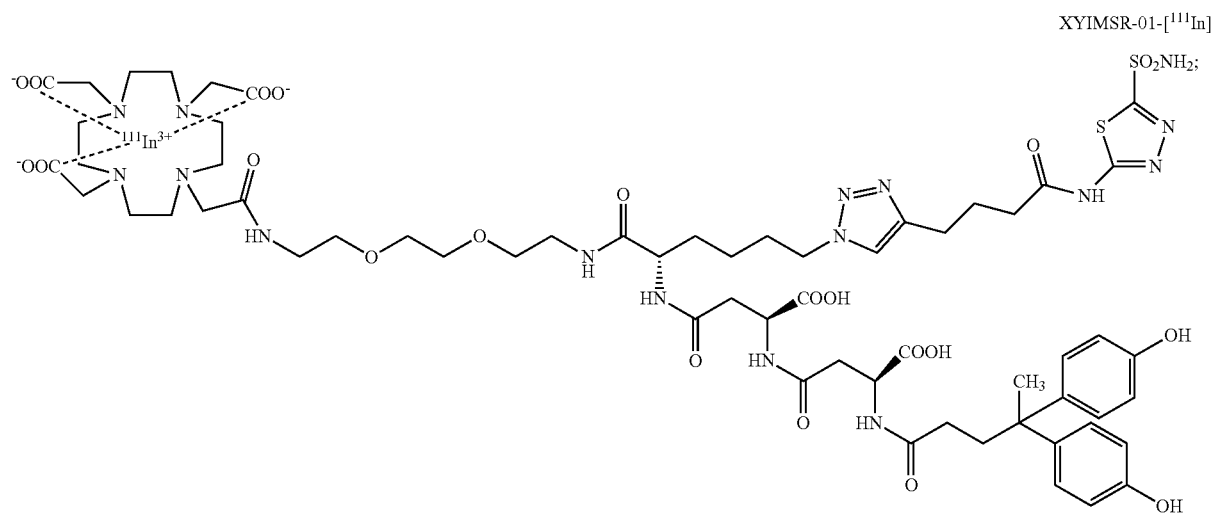
XYIMSR-01-[68Ga]
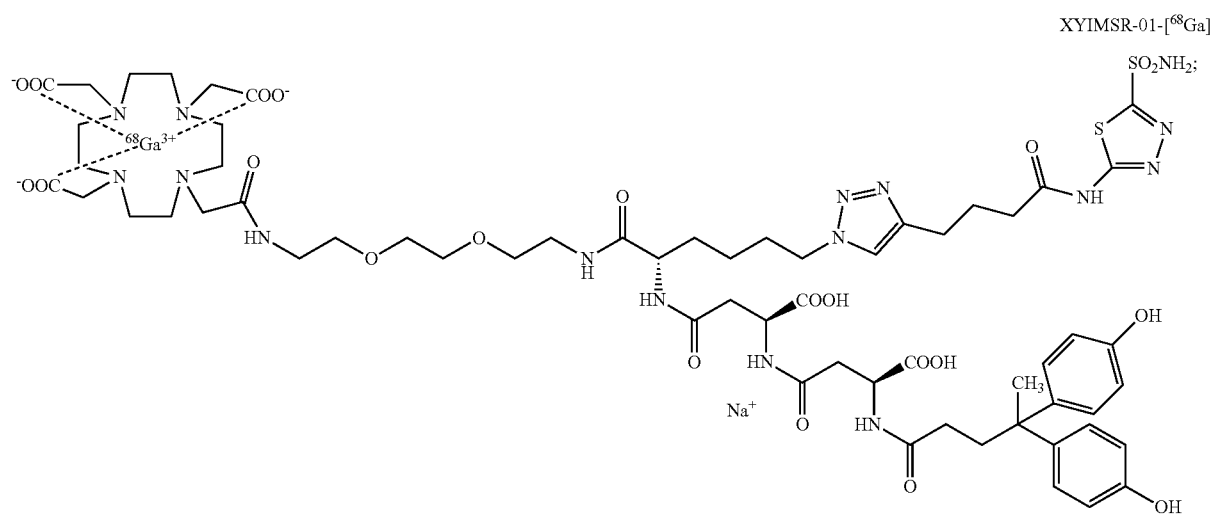
XYIMSR-01-[177Lu]
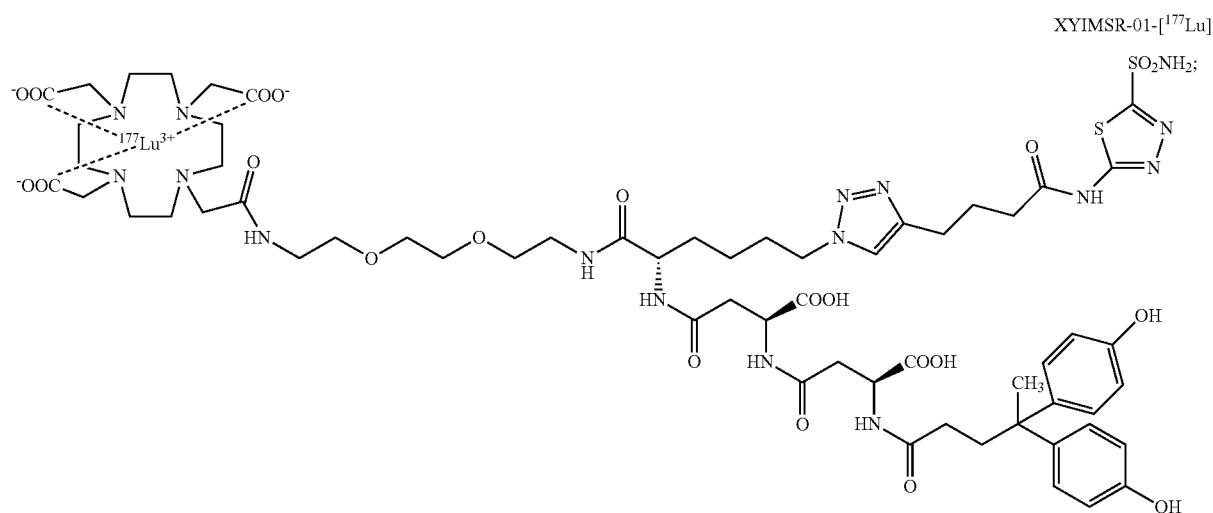

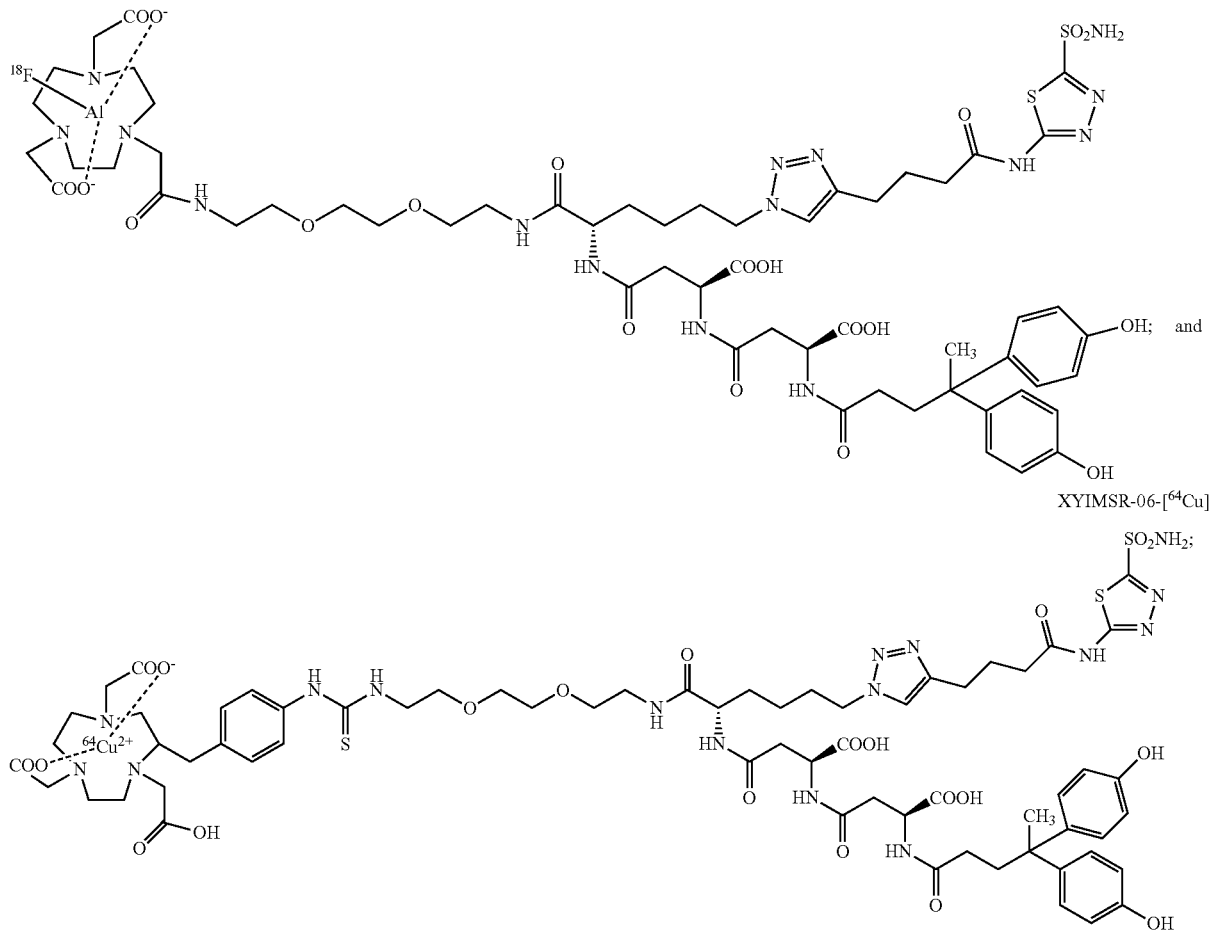

XYIMSR-04-[Al¹⁸F]

XYIMSR-06-[⁶⁴Cu]

or a pharmaceutically acceptable salt thereof.

"Contacting" means any action which results in at least one compound comprising the imaging agent of the presently disclosed subject matter physically contacting at least one CAIX-expressing tumor or cell. Contacting can include exposing the cell(s) or tumor(s) to the compound in an amount sufficient to result in contact of at least one compound with at least one cell or tumor. The method can be practiced in vitro or ex vivo by introducing, and preferably mixing, the compound and cell(s) or tumor(s) in a controlled environment, such as a culture dish or tube. The method can be practiced in vivo, in which case contacting means exposing at least one cell or tumor in a subject to at least one compound of the presently disclosed subject matter, such as administering the compound to a subject via any suitable route. According to the presently disclosed subject matter, contacting may comprise introducing, exposing, and the like, the compound at a site distant to the cells to be contacted, and allowing the bodily functions of the subject, or natural (e.g., diffusion) or man-induced (e.g., swirling) movements of fluids to result in contact of the compound and cell(s) or tumor(s).

By "making an image," it is meant using PET or SPECT to form an image of a cell, tissue, tumor, part of body, and the like.

As used herein, the term "treating" can include reversing, alleviating, inhibiting the progression of, preventing or reducing the likelihood of the cancer to which such term applies, or one or more symptoms or manifestations of such disease, disorder or condition, including killing or eliminating an infectious agent. Preventing refers to causing a disease, disorder, condition, or symptom or manifestation of such, or worsening of the severity of such, not to occur.

In other embodiments, the one or more Carbonic Anhydrase IX-expressing tumors or cells is selected from the group consisting of: a renal cell carcinoma, a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof. In specific embodiments, the one or more Carbonic Anhydrase IX-expressing tumors or cells is a renal cell carcinoma. In other embodiments, the one or more Carbonic Anhydrase IX expressing tumors or cells is in vitro, in vivo, or ex vivo. In particular embodiments, the one or more Carbonic Anhydrase IX-expressing tumors or cells is present in a subject.

The subject treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal (non-human) subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein.

In some embodiments, a detectably effective amount of the imaging agent of the presently disclosed methods is administered to a subject. In accordance with the presently disclosed subject matter, "a detectably effective amount" of the imaging agent is defined as an amount sufficient to yield an acceptable image using equipment which is available for clinical use. A detectably effective amount of the imaging agent may be administered in more than one injection. The detectably effective amount of the imaging agent can vary according to factors such as the degree of susceptibility of the individual, the age, sex, and weight of the individual, idiosyncratic responses of the individual, the dosimetry, and instrument and film-related factors. Optimization of such factors is well within the level of skill in the art.

It is preferable that the compounds of the presently disclosed subject matter are excreted from tissues of the body quickly. Typically compounds of the presently disclosed subject matter are eliminated from the body in less than about 48 hours. More preferably, compounds of the presently disclosed subject matter are eliminated from the body in less than about 24 hours, 16 hours, 12 hours, 8 hours, 6 hours, 4 hours, 2 hours, 90 minutes, or 60 minutes.

In some embodiments, the presently disclosed methods comprise clearance of the compound comprising the imaging agent from the tumor or cell in the subject. In some other embodiment, the imaging agent is cleared more rapidly from a subject's kidneys than from a tumor in the subject.

In some embodiments, the presently disclosed methods use compounds that are stable in vivo such that substantially all, e.g., more than about 50%, 60%, 70%, 80%, or more preferably 90% of the injected compound is not metabolized by the body prior to excretion. In other embodiments, the compound comprising the imaging agent is stable in vivo.

In general, the "effective amount" of an active agent refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

In some embodiments, the disease or condition is a cancer. Accordingly, the presently disclosed compounds can be administered prophylactically to prevent or reduce the incidence or recurrence of the cancer.

A "cancer" in a subject refers to the presence of cells possessing characteristics typical of cancer-causing cells, for example, uncontrolled proliferation, loss of specialized functions, immortality, significant metastatic potential, significant increase in anti-apoptotic activity, rapid growth and proliferation rate, and certain characteristic morphology and cellular markers. In some circumstances, cancer cells will be in the form of a tumor; such cells may exist locally within a subject, or circulate in the blood stream as independent cells, for example, leukemic cells.

A cancer can include, but is not limited to, renal cancer, head cancer, neck cancer, head and neck cancer, lung cancer, breast cancer, prostate cancer, colorectal cancer, esophageal cancer, stomach cancer, leukemia/lymphoma, uterine cancer, skin cancer, endocrine cancer, urinary cancer, pancreatic cancer, gastrointestinal cancer, ovarian cancer, cervical cancer, and adenomas. In some embodiments, a detectably effective amount of the therapeutic agent of the presently disclosed methods is administered to a subject.

In any of the above-described methods, the administering of a compound can result in at least about a 10%, 15%, 20%, 25%, 30%, 35%, 40%, 45%, 50%, 55%, 60%, 65%, 70%, 75%, 80%, 85%, 90%, 95%, or even 100% decrease in the amount of Carbonic Anhydrase IX released.

C. Pharmaceutical Compositions and Administration

In another aspect, the present disclosure provides a pharmaceutical composition including one compounds of formula (I), formula (II), formula (III) formula (IVa), formula (IVb), formula (IVc), and/or formula (IVd), alone or in combination with one or more additional therapeutic agents in admixture with a pharmaceutically acceptable excipient. One of skill in the art will recognize that the pharmaceutical compositions include the pharmaceutically acceptable salts of the compounds described above. Pharmaceutically acceptable salts are generally well known to those of ordinary skill in the art, and include salts of active compounds which are prepared with relatively nontoxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent or by ion exchange, whereby one basic counterion (base) in an ionic complex is substituted for another. Examples of pharmaceutically acceptable base addition salts include sodium, potassium, calcium, ammonium, organic amino, or magnesium salt, or a similar salt.

The term "combination" is used in its broadest sense and means that a subject is administered at least two agents, more particularly a compound of Formula (I), including compounds of formula (II), (III), (IVa), (IVb), (IVc), and/or (IVd), and optionally, one or more therapeutic agents. More particularly, the term "in combination" refers to the concomitant administration of two (or more) active agents for the treatment of a, e.g., single disease state. As used herein, the active agents may be combined and administered in a single dosage form, may be administered as separate dosage forms at the same time, or may be administered as separate dosage forms that are administered alternately or sequentially on the same or separate days. In one embodiment of the presently disclosed subject matter, the active agents are combined and administered in a single dosage form. In another embodiment, the active agents are administered in separate dosage forms (e.g., wherein it is desirable to vary the amount of one but not the other). The single dosage form may include additional active agents for the treatment of the disease state.

Advantageously, such combination therapies utilize lower dosages of the conventional therapeutics, thus avoiding possible toxicity and adverse side effects incurred when those agents are used as monotherapies.

The timing of administration of a compound of Formula (I) including compounds of formula (II), (III), (IVa), (IVb), (IVc), and/or (IVd), and at least one additional therapeutic agent can be varied so long as the beneficial effects of the combination of these agents are achieved. Accordingly, the phrase "in combination with" refers to the administration of a compound of Formula (I) including compounds of formula (II), (III), (IVa), (IVb), (IVc), and/or (IVd), and at least one additional therapeutic agent either simultaneously, sequentially, or a combination thereof. Therefore, a subject administered a combination of a compound of Formula (I) including compounds of formula (II), (III), (IVa), (IVb), (IVc), and/or (IVd), and at least one additional therapeutic agent can receive compound of Formula (I) including compounds of formula (II), (III), (IVa), (IVb), (IVc), and/or (IVd), and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of Formula (I), including compounds of formula (II), (III), (IVa), (IVb), (IVc), and/or (IVd),), and at least one additional therapeutic agent are administered simultaneously, they can be administered to the subject as separate pharmaceutical compositions, each comprising either a compound of Formula (I), including compounds of formula (II), (III), (IVa), (IVb), (IVc), and/or (IVd), or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of Formula (I), including compounds of formula (II), (III), (IVa), (IVb), (IVc), and/or (IVd), and at least one additional therapeutic agent is greater than the sum of the biological activities of the respective agents when administered individually.

Synergy can be expressed in terms of a "Synergy Index (SI)," which generally can be determined by the method described by F. C. Kull et al., Applied Microbiology 9, 538 (1961), from the ratio determined by:

$$Q_a/Q_A + Q_b/Q_B = \text{Synergy Index (SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

When compounds of the present disclosure contain relatively basic functionalities, acid addition salts can be obtained by contacting the neutral form of such compounds with a sufficient amount of the desired acid, either neat or in a suitable inert solvent or by ion exchange, whereby one acidic counterion (acid) in an ionic complex is substituted for another. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-toluenesulfonic, citric, tartaric, methanesulfonic, and the like. Also included are salts of amino acids such as arginate and the like, and salts of organic acids like glucuronic or galactunoric acids and the like (see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy (20$^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy (20$^{th}$ ed.) Lippincott, Williams & Wilkins (2000).

Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy (20$^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intrasternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, the bioavailability of the compound(s), the adsorption, distribution, metabolism, and excretion (ADME) toxicity of the compound(s), and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

D. Kits

In yet other embodiments, the presently disclosed subject matter provides a kit comprising a compound of formula (I), formula (II), formula (III), formula (IVa), formula (IVb), formula (IVc), and/or formula (IVd). In certain embodiments, the kit provides packaged pharmaceutical compositions comprising a pharmaceutically acceptable carrier, diluent, or excipient, and a presently disclosed compound. In certain embodiments the packaged pharmaceutical composition will comprise the reaction precursors necessary to generate the compound of the invention upon combination with a radio labeled precursor. Other packaged pharmaceutical compositions provided by the present invention further comprise indicia comprising at least one of: instructions for preparing compounds according to the invention from supplied precursors, instructions for using the composition to image cells or tissues expressing Carbonic Anhydrase IX, or instructions for using the composition to image glutamatergic neurotransmission in a patient suffering from a stress-related disorder, or instructions for using the composition to image prostate cancer.

II. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formula (I) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Description of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., C$_1$-C$_{10}$ means one to ten carbons, including 1, 2, 3, 4, 5, 6, 7, 8, 9, and 10 carbons). In particular embodiments, the term "alkyl" refers to C$_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, isopentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a C$_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to C$_{1-8}$ straight-chain alkyls. In other embodiments, "alkyl" refers, in particular, to C$_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, acylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized.

The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_{25}$—S(O)—$CH_3$, —$CH_2$—$CH_2$—S($O)_2$—$CH_3$, —CH=CH—O—$CH_3$, —Si($CH_3)_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3)_3$.

As described above, heteroalkyl groups, as used herein, include those groups that are attached to the remainder of the molecule through a heteroatom, such as —C(O)NR', —NR'R", —OR', —SR, —S(O)R, and/or —S($O_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, unsubstituted alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen molecule. Alkenyl groups include, for example, ethenyl (i.e., vinyl), propenyl, butenyl, 1-methyl-2-buten-1-yl, pentenyl, hexenyl, octenyl, allenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, and heptynyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH═CH— CH═CH—; —CH═CH—CH$_2$—; —CH$_2$CH$_2$CH$_2$CH$_2$—, —CH$_2$CH═CHCH$_2$—, —CH$_2$CsCCH$_2$—, —CH$_2$CH$_2$CH (CH$_2$CH$_2$CH$_3$)CH$_2$—, —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxyl (—O—(CH$_2$)$_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —CH$_2$—CH$_2$—S— CH$_2$—CH$_2$— and —CH$_2$—S—CH$_2$—CH$_2$—NH—CH$_2$—. For heteroalkylene groups, heteroatoms also can occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxy, arylthioxy, arylalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

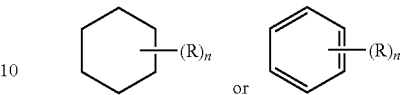

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

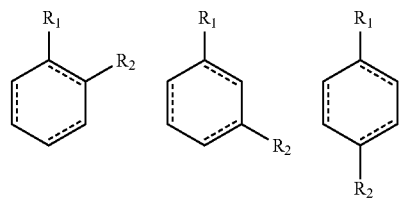

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ~~~ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', ═O, ═NR', —NR'R", —SR', -halogen, —SiR'R"R''', —OC(O)R', —C(O)R', —CO$_2$R', —C(O)

NR'R''', —OC(O)NR'R''', —NR''C(O)R', —NR'—C(O)NR''R''', —NR''C(O)OR', —NR—C(NR'R'')=NR''', —S(O)R', —S(O)$_2$R', —S(O)$_2$NR'R'', —NRSO$_2$R', —CN and —NO$_2$ in a number ranging from zero to (2m'+1), where m' is the total number of carbon atoms in such groups. R', R'', R''' and R'''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R'', R''' and R'''' groups when more than one of these groups is present. When R' and R'' are attached to the same nitrogen atom, they can be combined with the nitrogen atom to form a 4-, 5-, 6-, or 7-membered ring. For example, —NR'R'' is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R'', —SR', —SiR'R''R''', —OC(O)R', —C(O)R', —CO$_2$R', —C(O)NR'R'', —OC(O)NR'R'', —NR''C(O)R', —NR'—C(O)NR''R''', —NR''C(O)OR', —NR—C(NR'R''R''')=NR''', —NR—C(NR'R'')=NR'''—S(O)R', —S(O)$_2$R', —S(O)$_2$NR'R'', —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R'', R''' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R'', R''' and R'''' groups when more than one of these groups is present.

Two of the substituents on adjacent atoms of aryl or heteroaryl ring may optionally form a ring of the formula -T-C(O)—(CRR')$_q$-U-, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C''R''')$_d$—, where s and d are independently integers of from 0 to 3, and X' is —O—, —NR'—, —S—, —S(O)—, —S(O)$_2$—, or —S(O)$_2$NR'—. The substituents R, R', R'' and R''' may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as a 2-(furan-2-yl)acetyl)- and a 2-phenylacetyl group. Specific examples of acyl groups include acetyl and benzoyl. Acyl groups also are intended to include amides, —RC(=O)NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include C$_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, tert-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., C$_6$H$_5$—CH$_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and tert-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C(=O)— group wherein one of R and R' is hydrogen and the other of R and R' is alkyl and/or substituted alkyl as previously described. "Dialkylcarbamoyl" refers to a R'RN—C(=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —$(CH_2)_k$— where k is an integer from 2 to 6. Examples include, but are not limited to, methylamino, dimethylamino, ethylamino, diethylamino, diethylaminocarbonyl, methylethylamino, isopropylamino, piperidino, trimethylamino, and propylamino.

The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —$NO_2$ group.

The term "thio" refers to a compound described previously herein wherein a carbon or oxygen atom is replaced by a sulfur atom.

The term "sulfate" refers to the —$SO_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —$S(O_2)R$.

The term "sulfoxide" refers to a compound having a sulfinyl group —S(O)R

The term ureido refers to a urea group of the formula —NH—CO—$NH_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as D- or L- for amino acids, and individual isomers are encompassed within the scope of the present disclosure. The compounds of the present disclosure do not include those which are known in art to be too unstable to synthesize and/or isolate. The present disclosure is meant to include compounds in racemic, scalemic, and optically pure forms. Optically active (R)- and (S)-, or D- and L-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures with the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent or by ion exchange. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range.

Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Carbonic Anhydrase IX and Applications Thereof

Carbonic Anhydrase IX.

Carbonic anhydrase IX (CAIX) is a membrane-associated member of the carbonic anhydrase (CA) family (Krishnamurthy et al., 2008; Supuran, 2008; Alterio et al., 2012). These enzymes catalyze the reversible hydration of carbon dioxide to a bicarbonate anion and a proton. Fifteen human isoforms of CA have been identified. These isoforms show high sequence homology and share common structural features, including a zinc-containing catalytic site, a central twisted β-sheet surrounded by helical connections and additional β-strands (Altero et al., 2006; Lindskog et al., 1997; Hakansson et al., 1992; Christianson and Fierke, 1996). At the same time they are differ widely in molecular features, cellular localization, expression levels and tissue distribution (Clare and Supuran, 2006). CAIX is one of the transmembrane isoforms (along with CAIV, CAXII and CAXIV) and has limited expression in normal tissues with the exception of the gastrointestinal tract, gallbladder and pancreatic ducts (Supuran, 2008; Alterio et al., 2012; Christianson and Fierke, 1996).

CAIX as a Biomarker of Clear Cell RCC.

RCC is a primary epithelial malignancy of the renal parynchyma. To date, a number of different histologic variants of RCC have been described (Srigley et al., 2013). Most common among these is the clear cell (ccRCC) subtype. CcRCC is characterized by loss of the Von Hippel-Lindau (VHL) gene located at 3p25 (Cancer Genome Atlas Research Network, 2013). Under normoxic conditions, the VHL protein is responsible for ubiquitination of the hypoxia-inducible factor (HIF) (Gossage, 2015). Upon sensing hypoxia, the VHL gene releases its control over HIF leading to its localization to the nucleus where it up regulates the expression of a number of genes including CAIX and vascular endothelial growth factor (VEGF). Over-expression of CAIX has been demonstrated in approximately 95% of ccRCC specimens (Bui et al., 2003; Atkins et al., 2005; Leibovich et al., 2007). Given the ubiquitous overexpression of CAIX in cases of ccRCC, CAIX represents a rationale imaging and therapeutic target of this disease. Moreover, CAIX is unregulated in a number of other cancer types, both due to VHL loss and tissue hypoxia (include citations). Thus, ligands capable of selectively binding CAIX would have widespread utility in cancer imaging and therapeutics.

Significance for CAIX Imaging with Low-Molecular-Weight (LMW) Agents.

Feasibility for the non-invasive diagnosis of ccRCC via CAIX expression level has been extensively studied with the radiolabeled antibody G250, a murine monoclonal antibody (mAbG250) developed by immunization of mice with human ccRCC homogenates in 1986 (Oosterwijk et al., 1986). The clinical applications of this agent have been reviewed (Smaldone et al., 2012) and it was reported to identify ccRCC with 86% sensitivity, 87% specificity and 95% positive predictive value (Uzzo et al., 2010). However, antibodies as molecular imaging agents suffer from certain pharmacokinetic limitations, including slow blood/tissue clearance (normally 2-5 days or longer) and non-specific organ uptake. LMW imaging agents, especially $^{18}$F-labeled LMW agents, in principle, could provide superior imaging quality within 2 hours (Alauddin et al., 2012; Coenen et al., 2010; Cho et al., 2012). LMW agents are also more convenient to synthesize and to distribute to imaging centers. Although significant effort has been spent on sulfonamides and other CAIX ligands (Supuran, 2008; Alterio et al., 2012; Askoxylakis et al., 2010), no successful radionuclide-based molecular imaging agent has been reported (Pan et al., 2014; Akurathi et al., 2010; Lu et al., 2013; Doss et al., 2014; Rana et al., 2012). Most imaging results were reported with optical agents (Cecchi et al., 2005; Groves et al., 2012; Bao et al., 2012; Krall et al., 2014), but suffer from low tumor uptake (<2% ID/g) and highly variable imaging quality. Recently, significant progress in the field of CAIX imaging was reported by Wichert and coworkers with the identification of an additional surface binding pocket (Wichert et al., 2015). This dramatically reinforced the binding affinity of common sulfonamides over CAIX up to 0.2 nM and improved the tumor uptake by more than five times in ccRCC xenografts model as disclosed in FIG. 1A through FIG. 1D. In addition, the amino-containing western part of the molecule, was prove to expose to water and suitable for various modification. However, there are still two issues with this new generation dual-targeting agents: (1) the limited tissue penetration of optical agents and (2) the high kidney uptake precluding the use of this agent for imaging primary renal tumors apart from kidney background.

Fueled by the recent success of optical imaging of CAIX, PET/SPECT radioisotope labeled ligands have been investigated. As shown in FIG. 2A, the molecule contains an acetazolamide analog, 4,4-bis(4-hydroxyphenyl)valeric acid, an optimized linker and a modifiable amino group. FITC conjugated fluorescent ligand 1 has been synthesized, which reported with 0.2 nM Ki and excellent cellular uptake property on CAIX+ SK-RC-52 cells have been demonstrated, which is consistent with the earlier report (Wichert et al., 2015).

Significance for Nuclear Imaging and Radiotherapy.

Radionuclide molecular imaging including PET is the most mature molecular imaging technique without tissue penetration limitations. Due to its advantages of high sensitivity and quantifiability, radionuclide molecular imaging plays an important role in clinical and preclinical research (Youn and Honk, 2012; Chen et al., 2014). Many radionuclides, primarily β- and alpha emitters, have been investigated for targeted radioimmunotherapy and include both radiohalogens and radiometals (Table 1). The highly potent and specific binding moiety targeting CAIX enables its nuclear imaging and radiotherapy.

TABLE 1

Therapeutic Radionucleotides

| | |
|---|---|
| β-particle emitters | $^{90}$Y, $^{131}$I, $^{177}$Lu, $^{153}$Sm, $^{186}$Re, $^{188}$Re, $^{67}$Cu, $^{212}$Pb, $^{166}$Ho, $^{47}$Sc |
| α-particle emitters | $^{225}$Ac, $^{213}$Bi, $^{212}$Bi, $^{211}$At, $^{212}$Pb |
| Auger electron emitters | $^{125}$I, $^{123}$I, $^{67}$Ga, $^{111}$In, $^{80m}$Br |

Herein, the first synthesis of nuclear imaging and radiotherapy agents based on this dual-targeting moiety to CAIX is described. A new scaffold for radionuclide-based imaging and therapy of clear cell renal cell carcinoma (ccRCC) targeting carbonic anhydrase IX (CAIX) has been developed. The bivalent and low-molecular-weight ligands XYIMSR-01, a DOTA-conjugated, XYIMSR-04, a NOTA-conjugated, and XYIMSR-06, a Bz-NOTA-conjugated, have two moieties that target two separate sites on CAIX, imparting high affinity.

[$^{111}$In]XYIMSR-01 in 73.8-75.8% (n=3) yield has been synthesized with specific radioactivities ranging from 118-1,021 GBq/μmol (3,200-27,600 Ci/mmol). Single photon emission computed tomography of [$^{111}$In]XYIMSR-01 in immunocompromised mice bearing CAIX-expressing SK-RC-52 tumors revealed radiotracer uptake in tumor as early as 1 h post-injection. Rapid clearance from non-target tissues, including kidneys, allowed for high and specific signal by 24 h. Biodistribution studies demonstrated 26% injected dose per gram of radioactivity within tumor at 1 h. Tumor-to-blood, muscle and kidney ratios were 178.1±145.4, 68.4±29.0 and 1.7±1.2, respectively, at 24 h post-injection. Retention of radioactivity was exclusively observed in tumors by 48 h, the latest time point evaluated.

[$^{177}$Lu]XYIMSR-01 in 69.0% yield has been synthesized with specific radioactivity of 2,340 Ci/mmol; 73.0% with specific radioactivity of 2239 Ci/mmol, and in average yield of 60% (n=12), with average specific activity of 1,900 Ci/mmol (ranging from 1,200 Ci/mmol to 2,500 Ci/mmol). Single photon emission computed tomography of [$^{177}$Lu] XYIMSR-01 in immunocompromised mice bearing CAIX-expressing SK-RC-52 tumors revealed radiotracer uptake in tumor as early as 1 h post-injection. Rapid clearance from non-target tissues, including kidneys, allowed for high and specific signal by 24 h. Biodistribution studies confirmed the SPECT/CT data. Tumor-to-blood, muscle, and kidney ratios were 607.4±200.7, 128.4±25.4 and 4.5±1.4, respectively, at 24 h post-injection.

[Al$^{18}$F]XYIMSR-04 in 4.3% (n=3) yield has been synthetized with specific radioactivities of 2.1-3.4 GBq/μM (57-92 Ci/mmol). Positron emission tomography of [Al$^{18}$F] XYIMSR-04 in immunocompromised mice bearing CAIX-expressing SK-RC-52 tumors revealed radiotracer uptake in tumor at 1 h post-injection. Biodistribution studies demonstrated 14.40% injected dose per gram of radioactivity within tumor at 1 h. Tumor-to-blood, -muscle and -kidney ratio were 22.1, 9.74 and 0.28 respectively, at 1 h post-injection.

[$^{64}$Cu]XYIMSR-06, in 51.0±4.5% (n=5) yield has been synthetized with specific radioactivities of 4.1-8.9 GBq/μM (110-240 Ci/mmol). Positron emission tomography of [$^{64}$Cu]XYIMSR-06 in immunocompromised mice bearing CAIX-expressing SK-RC-52 tumors revealed radiotracer uptake in tumor as early as 1 h post-injection. By 24 h radioactivity within the tumors dropped to 6.2% injected dose per gram of radioactivity. Within 24 h, no significant radiotracer uptake within liver was observed, indicative of the in vivo stability of NOTA-$^{64}$Cu chelation.

The dual targeting strategy to engage CAIX enabled specific detection of ccRCC in this xenograft model, with pharmacokinetics surpassing those of previously described radionuclide-based probes against CAIX.

Example 2

Material and Methods

General Procedures.

Solvents and chemicals obtained from commercial sources were of analytical grade or better and used without further purification. Fmoc-protected azidolysine, HBTU, and N-α-fmoc-L-aspartic acid α-tert-butyl ester were purchased from Chem Impex International, Inc. (Wooddale, Ill.). Carrier-free [$^{111}$In]InCl$_3$ was purchased from MDS Nordion (Ottawa, ON, Canada). DOTA-NHS-ester (1,4,7,10-tetraazacyclododecane-1,4,7,10-tetraacetic acid mono N-hydroxysuccinimide ester) was purchased from Macrocyclics, Inc. (Dallas, Tex.). Indium (III) nitrate, triethylsilane (Et$_3$SiH), N,N-diisopropylethylamine (DIEA), triethylamine (TEA), piperidine, 4,4-bis(4-hydroxyphenyl)valeric acid, copper iodide (CuI), and tris[(1-benzyl-1H-1,2,3-triazol-4-yl)methyl]amine (TBTA) were purchased from Sigma-Aldrich (Saint Louis, Mo.). Pre-loaded O-bis-(aminoethyl)ethylene glycol on trityl resin was purchased from EMD Millipore (Billerica, Mass.). Flash chromatography was performed using MP SiliTech 32-63 D 60 Å silica gel purchased from Bodman (Aston, Pa.). Recombinant human CAIX was purchased from R&D Systems (Minneapolis, Minn.). 1H NMR spectra were recorded on a Bruker Ultrashield 500 MHz spectrometer. Chemical shifts (δ) were reported in ppm downfield by reference to proton resonances resulting from incomplete deuteration of the NMR solvent. ESI mass spectra were obtained on a Bruker Daltonics Esquire 3000 Plus spectrometer (Billerica, Mass.).

HPLC purification of non-labeled compounds were performed using a Phenomenex C18 Luna 10×250 mm column on a Agilent 1260 infinity LC system (Santa Clara, Calif.). HPLC purification of radiolabeled ($^{111}$In) ligand was performed on another Phenomenex C18 Luna 10×250 mm and a Varian Prostar System (Palo Alto, Calif.), equipped with a Varian ProStar 325 UV-Vis variable wavelength detector and a Bioscan (Poway, Calif.) Flow-count in-line radioactivity detector, all controlled by Galaxie software. The specific radioactivity was calculated as the ratio of the radioactivity eluting at the retention time of product during the preparative HPLC purification to the mass corresponding to the area under the curve of the UV absorption. The purity of tested compounds as determined by analytical HPLC with absorbance at 254 nm was >95%.

Synthesis of N$^4$—((S)-1-((2-(2-(2-aminoethoxy) ethoxy)ethyl)amino)-1-oxo-6-(4-(4-oxo-4-((5-sulfamoyl-1,3,4-thiadiazol-2-yl)amino)butyl)-1H-1,2,3-triazol-1-yl)hexan-2-yl)-N$^2$—((S)-3-(4,4-bis(4-hydroxyphenyl)pentanamido)-3-carboxypropanoyl)-L-asparagine (3)

Referring to FIG. 5, 3 was synthesized through an established solid phase based procedure (Wichert et al., 2015).

Synthesis of 2,2',2''-(10-((14S,18S,22S)-18,22-dicarboxy-27,27-bis(4-hydroxyphenyl)-2,13,16,20,24-pentaoxo-14-(4-(4-(4-oxo-4-((5-sulfamoyl-1,3,4-thiadiazol-2-yl)amino)butyl)-1H-1,2,3-triazol-1-yl) butyl)-6,9-dioxa-3,12,15,19,23-pentaazaoctacosyl)-1,4,7,10-tetraazacyclododecane-1,4,7-triyl)triacetic acid (XYIMSR-01)

Referring to FIG. 6, N$^4$—((S)-1-((2-(2-(2-aminoethoxy) ethoxy)ethyl)amino)-1-oxo-6-(4-(4-oxo-4-((5-sulfamoyl-1,3,4-thiadiazol-2-yl)amino)butyl)-1H-1,2,3-triazol-1-yl) hexan-2-yl)-N$^2$—((S)-3-(4,4-bis(4-hydroxyphenyl) pentanamido)-3-carboxypropanoyl)-L-asparagine (3) 19 mg (0.017 mmol), DOTA-NHS 7 16 mg (0.021 mmol) and N,N-diisopropylethylamine 150 μL were mixed in 2 mL DMSO. The reaction was stirred at room temperature for 2 h. Solvent was removed under vacuum. 21 mg (0.014 mmol) of product XYIMSR-01 was obtained as a white powder after purification by HPLC in 82% yield. HPLC conditions: Phenomenex, Luna 10×250 mm, 10 μm. Gradient 10/90/0.1 to 50/50/0.1 MeCN/H$_2$O/TFA, 0-10 min, flow 10 mL/min. Product eluted at 6.3 min. $^1$H-NMR (500 MHz, DMSO-d6): δ 13.01 (s, 1H), 12.77 (br. 2H), 9.17 (br. s, 2H), 8.53 (br, 1H), 8.33 (s, 2H), 8.19 (d, J=8.0, 1H), 8.09 (d, J=7.9, 1H), 7.91 (d, J=8.1, 1H), 7.88 (t, J=6.0, 1H), 7.84 (s, 1H), 7.45 (br. 2H), 6.92 (d, J=8.4, 4H), 6.64 (d, J=8.4, 4H), 4.54-4.44 (m, 2H), 4.24 (t, J=7.2, 2H), 4.17 (td, J=8.3, 5.5, 1H), 4.0-3.0 (36H, overlap with water signal), 2.65 (t, J=7.5, 2H), 2.64-2.55 (m, 4H), 2.51-2.41 (m, 2H), 2.17 (t, J=8.2, 2H) 1.94 (m, J=7.5, 2H), 1.88-1.82 (m, 2H), 1.75 (m, J=7.5, 2H), 1.66-1.60 (m, 1H), 1.53-1.46 (m, 1H), 1.45 (s, 3H), 1.28-1.17 (m, 2H). MS, calculated for $C_{61}H_{88}N_{16}NaO_{22}S_2^+$ [M+Na]$^+$: 1483.6; Found: 1483.4.

Synthesis of DOTA-In conjugated compound [In]-XYIMSR-01

Referring to FIG. 7, XYIMSR-01 2 mg (0.0013 mmol) was dissolved in 1 mL of 0.2 M NaOAc. Then, 20 μL of In(NO$_3$)$_3$ solution was added (containing 0.6 mg of In(NO$_3$)$_3$). The solution was kept at 60° C. for 30 min. 2.0 mg [In]-XYIMSR-01 was obtained as white crystal, after HPLC purification. Yield is 98%. HPLC condition: column Phenomenex, Luna 10×250 mm, 10 μm. 20/80/TFA MeCN/H$_2$O/TFA, flow 10 mL/min. Product was eluded at 10.6 min. MS, calculated for $C_{61}H_{85}InN_{16}NaO_{22}S_2^+$ [M+Na]$^+$: 1595.4; Found: 1595.3.

Synthesis of DOTA-Ga Conjugated Compound [Ga]-XYIMSR-01

Referring to FIG. 8, XYIMSR-01 2 mg (0.0013 mmol) was dissolved in 1 mL of pure water. Then, 20 µL of Ga(NO$_3$)$_3$ solution was added (containing 0.5 mg of Ga(NO$_3$)$_3$). The solution was kept at 60° C. for 30 min. 1.8 mg [Ga]-XYIMSR-01 was obtained as white crystal, after HPLC purification. Yield is 90%. HPLC condition: column Phenomenex, Luna 10×250 mm, 10 µm. 20/80/TFA MeCN/H$_2$O/TFA, flow 10 mL/min. Product was eluded at 10.2 min. MS, calculated for C$_{61}$H$_{85}$GaN$_{16}$NaO$_{22}$S$_2{}^+$ [M+Na]$^+$: 1549.5; Found: 1549.7.

Synthesis of DOTA-Lu Conjugated Compound [$^{175}$Lu]2,2',2''-(10-((14S,18S,22S)-18,22-dicarboxy-27,27-bis(4-hydroxyphenyl)-2,13,16,20,24-pentaoxo-14-(4-(4-(4-oxo-4-((5-sulfamoyl-1,3,4-thiadiazol-2-yl)amino)butyl)-1H-1,2,3-triazol-1-yl)butyl)-6,9-dioxa-3,12,15,19,23-pentaazaoctacosyl)-1,4,7,10-tetraazacyclododecane-1,4,7-triyl)triacetic acid ([Lu]XYIMSR-01)

Synthesis of DOTA-Lu conjugated compound [$^{175}$Lu]XYIMSR-01. Referring to FIG. 9, XYIMSR-01 1 mg (0.0007 mmol) was dissolved in 1 mL of 0.2 M NaOAc. Then, 10 µL of Lu(NO$_3$)$_3$ solution was added (containing 0.4 mg of Lu(NO$_3$)$_3$). The solution was kept at 60° C. for 30 min. 1.0 mg [$^{175}$Lu]XYIMSR-01 was obtained as white crystal, after HPLC purification. Yield is 90%. MS, calculated for C$_{61}$H$_{85}$LuN$_{16}$NaO$_{22}$S$_2{}^+$ [M+Na]$^+$: 1655.4766; Found: 1655.4787. HPLC, Column Phenomenex, Luna 10×250 mm, 10 µm, 20/80/0.1 MeCN/H$_2$O/TFA, flow 10 mL/min. Product was eluded at 14.1 min, with free ligand eluted first at 13.1. It is applied to preparative runs.

Synthesis of SFB Conjugated Compound XYIMSR-02.

Referring to FIG. 10, compound 3 10 mg (0.009 mmol), 4 5 mg (0.021 mmol) and di-isopropylethylamine 10 µL were dissolved in 1 mL DMF. The reaction was kept at room temperature for 1.5 hour. The solvent was removed under vacuum. 9 mg XYIMSR-02 was obtained after HPLC as white powder. Yield is 81%. HPLC condition: column Phenomenex, Luna 10×250 mm, 10 µm, Gradient 15/85/0.1 to 60/40/0.1 MeCN/H$_2$O/TFA, 0-10 min, flow 10 mL/min. Product was eluded at 7.1 min. $^1$H-NMR (500 MHz, DMSO-d6): δ 13.01 (s, 1H), 12.62 (br, 1H), 12.49 (br, 1H), 9.16 (br. s, 2H), 8.55 (br, 1H), 8.32 (s, 2H), 8.17 (d, J=8.0, 1H), 8.09 (d, J=7.9, 1H) 7.91 (d, J=8.1, 1H), 7.88 (t, J=6.0, 1H), 7.84 (s, 1H), 6.92 (d, J=8.4, 4H), 6.64 (d, J=8.4, 4H), 6.54 (br, 2H), 4.51-4.45 (m, 2H), 4.26 (t, J=7.2, 2H), 4.21 (td, J=8.3, 5.5, 1H), 3.53 (t, J=5.3, 2H), 3.56-3.50 (m, 4H), 3.38 (t, J=6.1, 2H), 3.24-3.15 (m, 2H), 2.65 (t, J=7.5, 2H), 2.64-2.55 (m, 4H), 2.51-2.41 (m, 2H), 2.17 (t, J=8.2, 2H) 1.95 (quin, J=7.5, 2H), 1.88-1.82 (m, 2H), 1.76 (quin, J=7.5, 2H), 1.66-1.60 (m, 1H), 1.53-1.46 (m, 1H), 1.45 (s, 3H), 1.28-1.17 (m, 2H). MS, calculated for C$_{52}$H$_{65}$FN$_{12}$NaO$_{16}$S$_2{}^+$ [M+Na]$^+$: 1219.4; Found: 1219.3.

Synthesis of 6-fluoro-pyridine-3-carbonyl Conjugated Compound (XYIMSR-03)

Referring to FIG. 11, compound 3 5 mg (0.0045 mmol), 5 4 mg and di-isopropylethylamine 20 µL were dissolved in 1 mL DMF. The reaction was kept at room temperature for 2 hour. The solvent was removed under vacuum. 2.8 mg XYIMSR-03 was obtained after HPLC as white powder. Yield is 52%. HPLC condition: column Phenomenex, Luna 10×250 mm, 10 µm. Gradient 15/85/0.1 to 60/40/0.1 MeCN/H$_2$O/TFA, 0-10 min, flow 10 mL/min. Product was eluded at 6.9 min. MS, calculated for C$_{51}$H$_{63}$FN$_{13}$O$_{15}$S$_2{}^+$ [M+H—H$_2$O]$^+$: 1180.4; Found: 1180.4.

Synthesis of NOTA Conjugated Compound 2,2'-(7-((14S,18S,22S)-18,22-dicarboxy-27,27-bis(4-hydroxyphenyl)-2,13,16,20,24-pentaoxo-14-(4-(4-(4-oxo-4-((5-sulfamoyl-1,3,4-thiadiazol-2-yl)amino)butyl)-1H-1,2,3-triazol-1-yl)butyl)-6,9-dioxa-3,12,15,19,23-pentaazaoctacosyl)-1,4,7-triazonane-1,4-diyl)diacetic acid (XYIMSR-04)

Referring to FIG. 12, 3 14 mg (0.0126 mmol), NOTA-NHS 10 mg (0.0151 mmol) and triethylamine 50 µL were mixed in 2 mL DMF. The reaction was stirred at room temperature for 2 hours. All the solvent was removed under vacuum. 9.0 mg product XYIMSR-04 was obtained as white powder, after HPLC purification. Yield is 52%. HPLC condition: column Phenomenex, Luna 10×250 mm, 10 µm. Gradient 10/90/0.1 to 50/50/0.1 MeCN/H$_2$O/TFA, 0-10 min, flow 10 mL/min. Product was eluded at 6.9 min. $^1$H-NMR (500 MHz, DMSO-d6): δ 12.99 (s, 1H), 12.25 (br. 2H), 9.15 (br. s, 2H), 8.31 (s, 2H), 8.24 (m, 1H), 8.16 (d, J=8.0, 1H), 8.05 (d, J=7.9, 1H), 7.90 (d, J=8.1, 1H), 7.88 (t, J=6.0, 1H), 7.83 (s, 1H), 6.92 (d, J=8.4, 4H), 6.64 (d, J=8.4, 4H), 6.50 (br, 2H), 4.52-4.46 (m, 2H), 4.24 (t, J=7.2, 2H), 4.17 (td, J=8.3, 5.5, 1H), 4.0-2.84 (overlap with water signal), 2.65 (t, J=7.5, 2H), 2.64-2.55 (m, 4H), 2.47-2.41 (m, 2H), 2.17 (t, J=8.2, 2H), 1.94 (m, J=7.5, 2H), 1.88-1.82 (m, 2H), 1.75 (m, J=7.5, 2H), 1.66-1.60 (m, 1H), 1.53-1.46 (m, 1H), 1.45 (s, 3H), 1.28-1.17 (m, 2H). MS, calculated for C$_{57}$H$_{81}$N$_{15}$NaO$_{20}$S$_2{}^+$ [M+Na]$^+$: 1382.5; Found: 1382.8.

Synthesis of NOTA-Al—F Conjugated Compound [Al$^{19}$F] 2,2'-(7-((14S,18S,22S)-18,22-dicarboxy-27,27-bis(4-hydroxyphenyl)-2,13,16,20,24-pentaoxo-14-(4-(4-(4-oxo-4-((5-sulfamoyl-1,3,4-thiadiazol-2-yl)amino)butyl)-1H-1,2,3-triazol-1-yl)butyl)-6,9-dioxa-3,12,15,19,23-pentaazaoctacosyl)-1,4,7-triazonane-1,4-diyl)diacetic acid ([Al$^{19}$F]XYIMSR-04)

Referring to FIG. 13, XYIMSR-04 1 mg (0.0007 mmol) was dissolved in 1 mL water/Ethanol 1:1. To the solution, 500 µL of AlCl$_3$ 2 mmol/NaOAc 2 mmol water solution (pH=4) was added. Then, 500 µL of 10 mmol KF solution was added, together with 1 mL of ethanol. The resulting solution was heated at 110° C. for 30 min. 0.6 mg of [Al$^{19}$F]XYIMSR-04 was obtained as white crystal, after HPLC purification. Yield is 61%. HPLC condition: column Phenomenex, Luna 10×250 mm, 10 µm. 20/80/TFA MeCN/H$_2$O/TFA, flow 4 mL/min. Product was eluded at 35.5 min. MS, calculated for C$_{57}$H$_{79}$AlFN$_{15}$NaO$_{20}$S$_2{}^+$ [M+Na]$^+$: 1426.4759; Found: 1426.4777.

Synthesis of Conjugated Compound XYIMSR-05

Referring to FIG. 14, compound 3 4 mg (0.0036 mmol), 6 4 mg and di-isopropylethylamine 20 µL were dissolved in 1 mL DMF. The reaction was kept at room temperature for 2 hour. The solvent was removed under vacuum. 2.9 mg XYIMSR-05 was obtained after HPLC as white powder. Yield is 62%. HPLC condition: column Phenomenex, Luna 10×250 mm, 10 µm. Gradient 15/85/0.1 to 60/40/0.1 MeCN/

H₂O/TFA, 0-10 min, flow 10 mL/min. Product was eluded at 7.6 min. MS, calculated for $C_{52}H_{66}IN_{12}O_{16}S_2^+$ [M+H]+: 1305.3; Found: 1305.2.

Synthesis of NOTA Conjugated Compound 2,2',2''-(2-(4-(3-(((11S,15S,19S)-15,19-dicarboxy-24,24-bis(4-hydroxyphenyl)-10,13,17,21-tetraoxo-11-(4-(4-(4-oxo-4-((5-sulfamoyl-1,3,4-thiadiazol-2-yl)amino)butyl)-1H-1,2,3-triazol-1-yl)butyl)-3,6-dioxa-9,12,16,20-tetraazapentacosyl)thioureido)benzyl)-1,4,7-triazonane-1,4,7-triyl)triacetic acid (XYIMSR-06)

Referring to FIG. 15, compound 3 (Wichert et al., 2015) 12 mg (0.0111 mmol), p-SCN-Bn-NOTA 8 mg (0.0143 mmol) and N,N-diisopropylethylamine 50 μL were mixed in 2 mL DMF. The reaction was stirred at room temperature for 2 h. Solvent was removed under vacuum. 14.0 mg of product XYIMSR-06 was obtained as a white powder after HPLC purification. Yield was 83%. HPLC conditions: column Phenomenex, Luna 10×250 mm, 10 μm. 25/75/0.1 MeCN/H₂O/TFA, flow 10 mL/min. Product eluted at 12.0 min. ¹H-NMR (500 MHz, DMSO-d₆): δ 12.98 (s, 1H), 12.63 (br. 2H), 9.60 (m, 1H), 9.15 (br. s, 2H), 8.31 (s, 2H), 8.16 (d, J=8.0, 1H), 8.05 (d, J=7.9, 1H), 7.90 (d, J=8.1, 1H), 7.88 (t, J=6.0, 1H), 7.83 (s, 1H), 7.69 (br, 1H), 7.41 (d, J=8.0 Hz, 2H), 7.19 (d, J=8.0 Hz, 2H), 6.92 (d, J=8.4, 4H), 6.64 (d, J=8.4, 4H), 6.50 (br, 2H), 4.52-4.46 (m, 2H), 4.24 (t, J=7.2, 2H), 4.17 (td, J=8.3, 5.5, 1H), 4.0-2.90 (overlaps with water signal), 2.65 (t, J=7.5, 2H), 2.64-2.55 (m, 4H), 2.47-2.41 (m, 2H), 2.17 (t, J=8.2, 2H), 1.94 (m, J=7.5, 2H), 1.88-1.82 (m, 2H), 1.75 (m, J=7.5, 2H), 1.66-1.60 (m, 1H), 1.53-1.46 (m, 1H), 1.45 (s, 3H), 1.28-1.17 (m, 2H). MS, calculated for $C_{65}H_{89}N_{16}O_{21}S_3^+$ [M+H]⁺: 1525.5545; Found: 1525.5527.

Synthesis of [$^{63/65}$Cu]2,2',2''-(2-(4-(3-(((11S,15S,19S)-15,19-dicarboxy-24,24-bis(4-hydroxyphenyl)-10,13,17,21-tetraoxo-11-(4-(4-(4-oxo-4-((5-sulfamoyl-1,3,4-thiadiazol-2-yl)amino)butyl)-1H-1,2,3-triazol-1-yl)butyl)-3,6-dioxa-9,12,16,20-tetraazapentacosyl)thioureido)benzyl)-1,4,7-triazonane-1,4,7-triyl)triacetic acid ([$^{63/65}$Cu]XYIMSR-06)

Referring to FIG. 16, XYIMSR-06 1 mg (0.0007 mmol) was dissolved in 0.5 mL 0.2 M NaOAc solution. To the solution 0.2 mg Cu(NO₃)₂3H₂O was added in 0.1 mL of water. The reaction was heated at 100° C. for 10 min and then loaded onto HPLC for purification. 0.5 mg of product was obtained as blue crystals. Yield was 48%. HPLC conditions: column Phenomenex, Luna 10×250 mm, 10 μm. 25/75/TFA MeCN/H₂O/TFA, flow 10 mL/min. Product eluted at 8.3 min with the starting material eluting at 12.6 min. MS, calculated for $C_{65}H_{87}CuN_{16}O_{21}S_3^+$ [M+H]+: 1586.4684; Found: 1586.4683.

Radiolabeling of [$^{111}$In]XYIMSR-01

20 μg XYIMSR-01 was dissolved in 10 μL of 0.2 M NaOAc followed by addition of 3.3 mCi of $^{111}$InCl₃ solution to provide a final pH=5.5-6. The mixture was heated in a water bath at 65° C. for 30 min. Radiolabeling was monitored by HPLC. At completion, the reaction mixture was diluted with 1 mL of water then loaded onto a preparative HPLC column for purification. Retention times for the radiolabeled compound, [$^{111}$In]XYIMSR-01, and starting material, XYIMSR-01, were optimized to the point of baseline separation, with [$^{111}$In]XYIMSR-01 eluting first. 2.5 mCi of [$^{111}$In]XYIMSR-01 was obtained at a radiochemical yield of 75.8% in specific radioactivities of 118.4 GBq/μmol (3,200 Ci/mmol). The identity of the radiolabeled product was confirmed by co-injection with [$^{113/115}$In]XYIMSR-01 and co-elution on HPLC with the same condition. Another two syntheses were performed under similar conditions. The average yield was 74% (n=3). The specific activities ranged from 118 to 1021.2 GBq/μmol (3,200 to 27,600 Ci/mmol). For preparative runs, the HPLC solvent was removed under vacuum. [$^{111}$In]XYIMSR-01 was formulated in phosphate-buffered saline (PBS) for the imaging study. HPLC conditions: Phenomenex, Luna 10×250 mm, 19/81/0.1 MeCN/H₂O/TFA, flow 4 mL/min. Product eluted at 28.3 min, while starting material eluted at 30.2 min.

Radiolabeling of XYIMSR-01-[$^{177}$Lu]

20 μg XYIMSR-01 was dissolved in 10 μL of 0.2M NaOAc followed by addition of 10.1 mCi of $^{177}$LuCl₃ solution to provide a final pH=5.5-6. The mixture was heated in a water bath at 65° C. for 30 min. Radiolabeling was monitored by HPLC. At completion, the reaction mixture was diluted with 0.2 mL of water then loaded onto a preparative HPLC column for purification. Retention times for the radiolabeled compound, [$^{177}$Lu]XYIMSR-01, and starting material, XYIMSR-01, were optimized to the point of baseline separation, with XYIMSR-01-[$^{177}$Lu] eluting first. 6.97 mCi of XYIMSR-01-[$^{177}$Lu] was obtained at a radiochemical yield of 69.0% in specific radioactivities of 2,340 Ci/mmol. The identity of the radiolabeled product was confirmed by co-injection with XYIMSR-01-[Lu] and co-elution on HPLC with the same condition. Another one syntheses were performed under similar conditions, starting with 10.2 mCi and obtaining 7.30 mCi at yield of 73.0% and specific radioactivity of 2239 Ci/mmol. The product was diluted with water, loaded onto Sep-Pak and eluded with 2 mL pure ethanol. After the concentrated under nitrogen gas, XYIMSR-01-[$^{177}$Lu] was formulated in phosphate-buffered saline (PBS) for the study. HPLC conditions: Phenomenex, Luna 4.6×250 mm, 5 μm. 22/78/0.1 MeCN/H2O/TFA, flow 0.5 mL/min. Product eluted at 24.5 min, while starting material eluted at 29.0 min.

Yet other syntheses were performed under similar conditions, starting with 8.4-20.7 mCi. At completion, the reaction mixture was diluted with 200 μL of water, loaded onto a HPLC column for purification. With Method B, [$^{177}$Lu]XYIMSR-01 got eluted first and collected. Base line separation between radiolabel product and starting material was achieved. The average radiochemical yield is 60% (n=12), with average specific activity of 1,900 Ci/mmol (ranging from 1,200 Ci/mmol to 2,500 Ci/mmol). HPLC column Phenomenex, Luna 4.6×250 mm, 5 μm. 21/79/0.1 MeCN/H2O/TFA, flow 0.5 mL/min. Product was eluded at 30.5 min, with free ligand eluted second at 36.1 min.

Radiolabeling of XYIMSR-04-[Al$^{18}$F]

20 μL of 1 mM XYIMSR-04 in water/EtOH 1/1 was added to 200 μL of Na$^{18}$F in 0.9% saline containing 1.3 mCi activity. To this mixture, 1 μL of 2 mM AlCl₃/NaOAc solution and 200 μL of ethanol were added. The reaction was kept at 105° C. for 20 min, then diluted with 1.5 mL of water and loaded onto a preparative HPLC column for purification. Retention times for the radiolabeled compound, XYIMSR-04-[Al$^{18}$F], and starting material, XYIMSR-04, were optimized to the point of baseline separation, with XYIMSR-04-[Al$^{18}$F] eluting first. 180 μCi of XYIMSR-04-

[Al$^{18}$F] was obtained a radiochemical yield of 13.8% in specific radioactivity of >1000 Ci/mmol in 1 hour. HPLC conditions: Phenomenex, Luna 10×250 mm, 10 μm. 20/80/0.1 MeCN/H2O/TFA, flow 0.5 mL/min. Product eluted at 35.5 min, while starting material eluted at 39.0 min.

Another radiosynthesis of XYIMSR-04-[Al$^{18}$F] was performed. Na$^{18}$F in saline was purchased from PETNET (Hackensack, N.J.) and was directly used in the synthesis 400 μg of XYIMSR-04 in 200 μL water/ethanol 1:1 was added to 1 mL of Na$^{18}$F in 0.9% saline containing 0.17-0.52 GBq (4.6-14.0 mCi) of radioactivity. To this mixture 20 μL of 2 mM AlCl$_3$/NaOAc solution and 200 μL of ethanol were added. The reaction was kept at 105° C. for 20 min, then diluted to 2.0 mL with water and loaded onto a preparative HPLC column for purification. Retention times for the radiolabeled compound, [Al$^{18}$F]XYIMSR-04, and starting material, XYIMSR-04, were optimized to the point of baseline separation, with [Al$^{18}$F]XYIMSR-04 eluting first. [Al$^{18}$F]XYIMSR-04 was obtained in a radiochemical yield of 4.3% (n=3) in specific radioactivity of 2.1-3.4 GBq/μmol (57-92 Ci/mmol) in 1.5 h. HPLC conditions: Phenomenex, Luna 10×250 mm, 10 μm. 20/80/0.1 MeCN/H$_2$O/TFA, flow 4 mL/min. Product eluted at 35.5 min, while starting material eluted at 39.0 min. The collected activity was diluted with 20 mL of water and loaded onto an activated Sep-Pak column (WAT020515, Waters, Milford Mass.). After the Sep-Pak was washed with 10 mL of water, [Al$^{18}$F]XYIMSR-04 was eluted with 2 mL of ethanol. The ethanol was evaporated under a gentle stream of N$_2$ (to a total volume of <50 μL). The resulting solution was formulated in saline for the imaging and biodistribution studies.

Radiolabeling of [$^{64}$Cu]XYIMSR-06

40 μg of XYIMSR-06 in 20 μL 0.2 M NaOAc solution was added to 60 μL $^{64}$CuCl$_2$ with 0.16-0.26 GBq (4.2-6.9 mCi) of radioactivity. The reaction was heated in a water bath at 65° C. and pH 5.5-6 for 0.5 h. The reaction was then diluted with 1.5 mL of water and injected onto the HPLC for purification. Baseline separation was achieved between [$^{64}$Cu]XYIMSR-06 and XYIMSR-06 with [$^{64}$Cu]XYIMSR-06 eluting first. The average non-decay corrected radiochemical yield was 51.0±4.5% (n=5) and specific activities were 4.1-8.9 GBq/μmol (110-240 Ci/mmol). HPLC conditions: column Phenomenex, Luna 10×250 mm, 10 μm. 23/77/TFA MeCN/H$_2$O/TFA, flow 4 mL/min. Product eluted at 29.2 min. The collected radioactivity was diluted with 20 mL of water and loaded onto activated Sep-Pak (WAT020515, Waters, Milford Mass.). After the Sep-Pak was washed with 10 mL of water, [$^{64}$Cu]XYIMSR-06 was eluted with 2 mL of ethanol. The ethanol was evaporated under a gentle stream of N$_2$ (to a total volume of <50 μL). The resulting solution was formulated in saline for the imaging and biodistribution studies.

Cell Lines and Mouse Models.

Animal experiments were performed in accordance with protocols approved by the Johns Hopkins Animal Care and Use Committee (ACUC). Six-week-old female NOD/SCID mice were purchased from the Animal Resource Core of the Sidney Kimmel Comprehensive Cancer Center of Johns Hopkins and were subcutaneously injected in the lower left flank or upper right flank with 1×10$^6$ SK-RC-52 cells in RPMI 1640 GlutaMAX™ media (Life Technologies, Frederick, Md.) supplemented with 1% fetal bovine serum (FBS). Mice were monitored for tumor size and used for SPECT/CT imaging when the size of the tumor reached 100 mm$^3$.

FACS Analysis.

CAIX-positive SK-RC-52 and CAIX-negative BxPC3 cells were maintained in RPMI 1640 media supplemented with 10% FBS and 1× penicillin-streptomycin in a 37° C. humidified incubator. Cells were detached from the flask with trypsin and reconstituted in RPMI 1640 media supplemented with 1% FBS at a density of 1×10$^6$ cells per mL. FITC-labeled 8 was added to the cells at the indicated concentration and incubated at room temperature for 30 min. Cells were washed twice with the same media for staining and analyzed using the FACSCalibur (BD Bioscience, San Jose, Calif.) instrument.

Competitive Fluorescence Polarization Assay for [$^{113/115}$In]YIMSR-01.

Fluorescence polarization (FP) experiments were performed in 21 μL of the assay buffer (12.5 mM Tris-HCl, pH 7.5, 75 mM NaCl) in black flat bottom 384-well microplates (Corning, Inc., New York, N.Y.) The FP reaction employed 100 nM of purified CAIX (R&D systems, Minneapolis, Minn.) and 80 nM FITC-labeled 8 (Wichert, et al., 2015) within the assay buffer. The FP values were measured as mP units using the Victor3 multi-label plate reader equipped with excitation (485 nm) and emission (535 nm) filters (Perkin Elmer, Waltham, Mass.). 100 nM CAIX was incubated with serially diluted (from 1 μM to 61 fM) concentrations of the three targeting molecules, 2, XYIMSR-01, and [$^{113/115}$In]XYIMSR-01 for 30 min at room temperature in 384-well plates. 80 nM 8 was added to each well and the reaction was incubated for 30 min at room temperature followed by FP measurement. Experiments were carried out in triplicate and the concentration resulting in 50% response (IC$_{50}$) was calculated in GraphPad Prism 5 (GraphPad Software, La Jolla, Calif.) using the sigmoidal dose-response regression function.

Competitive Fluorescence Polarization Assay for [Al$^{19}$F]XYIMSR-04, [$^{63/65}$Cu]XYIMSR-06, and [$^{175}$Lu]XYIMSR-01.

Fluorescence polarization (FP) experiments were performed in 21 μL of the assay buffer (12.5 mM Tris-HCl, pH 7.5, 75 mM NaCl) in transparent flat bottom 384 well Small Volume™ LoBase Microplates (Greiner Bio-One, Frickenhausen Germany). The FP reaction employed 100 nM of purified CAIX (R&D systems, Minneapolis, Minn.) and 80 nM FITC-labeled ligand within the assay buffer. The FP values were measured as mP units using the Safire2™ plate reader (Tecan, Morrisville, N.C.) with excitation at 475 nm and emission at 532 nm emission. 100 nM CAIX was incubated with serially diluted (from 8 μM to 488.2 fM) concentrations of the three targeting molecules, [Al$^{19}$F]XYIMSR-04, [$^{63/65}$Cu]XYIMSR-06 and [$^{175}$Lu]XYIMSR-01 for 30 min at room temperature in 384 well plates. 80 nM FITC-labeled ligand was added to each well and the reaction was incubated for 30 min at room temperature followed by FP measurements. Experiments were carried out in triplicate and the concentration resulting in 50% response (IC$_{50}$) was calculated in GraphPad Prism 5 (GraphPad Software, La Jolla, Calif.) using the sigmoidal dose-response regression function.

SPECT/CT Imaging of [$^{111}$In]XYIMSR-01.

Mice harboring subcutaneous SK-RC-52 tumors with the lower left flank were injected with 14.8 MBq (400 μCi) of [$^{111}$In]XYIMSR-01 in 250 μL of PBS (pH=7.0) intravenously (tail vein). Anesthesia was then induced with 3% isofluorane and maintained at 2% isoflurane. Physiologic temperature was maintained with an external light source while the mouse was on the gantry. Imaging employed a CT-equipped Gamma Medica-Ideas SPECT scanner (Northridge, Calif.). SPECT data were acquired in 64 projections at 65 s per projection using medium energy pinhole collimators. A CT scan was performed in 512 projections at the end of each SPECT scan for anatomic co-registration. CT and SPECT scans were performed at 1, 4, 8, 24, and 48 h post-injection of [$^{111}$In]XYIMSR-01. Imaging data sets were reconstructed using the manufacturer's software. Display of images utilized Amide software (Dice Holdings, Inc. NY).

SPECT/CT Imaging of [$^{177}$Lu]XYIMSR-01.

Mice were injected with 1.7 mCi of [$^{177}$Lu]XYIMSR-01 in 250 uL of PBS (pH7.0) intravenously, anesthetized under 3% isofluorane prior to being placed on the scanner bed and kept warm with an external light source while being scanned. Isofluorane levels were decreased to 1% throughout the scanning process in order to ensure mouse survival. Imaging of mice was then carried out using a CT-equipped Gamma Medica-Ideas SPECT scanner (Northridge, Calif.). A CT scan was performed at the end of each SPECT scan for anatomical co-registration. CT and SPECT scans were performed at 1, 4, 8, 24, and 48 hrs post injection of the [$^{177}$Lu]XYIMSR-01. Obtained data sets were subsequently reconstructed using the provided Gamma Medica-Ideas software. Final data visualization and image generation was accomplished using Amide software (Dice Holdings, Inc. NY).

PET/CT Imaging of [Al$^{18}$F]XYIMSR-04.

Mice harboring subcutaneous SK-RC-52 tumors with the lower left flank were injected with 7.4 MBq (200 µCi) of [Al$^{18}$F]XYIMSR-04 in 250 µL of PBS (pH=7.0) intravenously (tail vein). Anesthesia was then induced with 3% isofluorane and maintained at 2% isoflurane. Physiologic temperature was maintained with an external light source while the mouse was on the gantry. Imaging employed a CT-equipped Gamma Medica-Ideas SPECT scanner (Northridge, Calif.). Whole body 2-bed PET scan was performed using ARGUS small-animal PET/CT scanner (Sedecal, Madrid, Spain) at 250-700 keV energy window. PET acquisition times were: 5 min/bed (1 h) post-injection of [Al$^{18}$F]XYIMSR-04. PET images were co-registered with the corresponding 360-slice CT images. Imaging datasets were reconstructed using the 3D-FORE/2D-OSEM iterative algorithm with 2 iterations and 16 subsets, using the manufacturer's software. Display of images utilized Amide software (Dice Holdings, Inc. NY).

PET/CT Imaging of [$^{64}$Cu]XYIMSR-06.

Mice harboring subcutaneous SK-RC-52 tumors within the upper right flank were injected intravenously (tail vein) with 22.2 MBq (600 µCi) of [$^{64}$Cu]XYIMSR-06 in 250 µL of PBS (pH=7.0). Anesthesia was then induced with 3% isoflurane and maintained with 2% isoflurane. Physiologic temperature was maintained with an external light source while the mouse was on the gantry. Whole body, 2-bed PET/CT imaging was performed using the SuperArgus small animal PET/CT scanner (Sedecal, Madrid, Spain), CT employing a 250-700 keV energy window. PET acquisition times were: 5 min/bed position (1 h post-injection of [$^{64}$Cu]XYIMSR-06); 10 min/bed position (4 and 8 h) and 20 min/bed position (24 h). PET images were co-registered with the corresponding 360-slice CT images. Imaging datasets were reconstructed using the 3D-FORE/2D-OSEM iterative algorithm with 2 iterations and 16 subsets, using the manufacturer's software. Imaging data sets were reconstructed using the manufacturer's software. Display of images utilized the software package PMOD (v3.3, PMOD Technologies Ltd, Zurich, Switzerland).

Biodistribution of [$^{111}$In]XYIMSR-01 and [$^{177}$Lu]XYIMSR-01.

Mice bearing SK-RC-52 xenografts at lower left flank were injected intravenously with 740 kBq (20 µCi) of [$^{111}$In]XYIMSR-01, or [$^{177}$Lu]XYIMSR-01 in 200 µL of PBS. For competitive blocking, same tumor bearing mice were injected with 740 kBq (20 µCi) of [$^{111}$In]XYIMSR-01 and 200 nmole of 8 in 200 µL of PBS. At 1 h, 4 h, 8 h, 24 h and 48 h post-injection, mice were sacrificed by cervical dislocation and the blood was immediately collected by cardiac puncture. Heart, lungs, pancreas, spleen, fat, brain, muscle, small intestines, liver, stomach, kidney, urinary bladder, and tumor were collected. Each organ was weighed and the tissue radioactivity was measured with an automated gamma counter (1282 Compugamma CS, Pharmacia/LKB-Nuclear, Inc., Mt. Waverly, Vic. Australia). The percentage of injected dose per gram of tissue (% ID/g) was calculated by comparison with samples of a standard dilution of the initial dose. All measurements were corrected for radioactive decay.

Data were expressed as mean±standard deviation (SD). Prism software (GraphPAD, San Diego, Calif.) was used to determine statistical significance. Statistical significance was calculated using a paired t test. P-values <0.0001 were considered significant.

Biodistribution of [Al$^{18}$F]XYIMSR-04.

Mice bearing SK-RC-52 xenografts within the lower left flank were injected intravenously with 740 kBq (20 µCi) of [Al$^{18}$F]XYIMSR-04 in 200 µL of PBS. At specific 1 hour time point mentioned in the paper, mice (n=5) were sacrificed by cervical dislocation and the blood was immediately collected by cardiac puncture. Heart, lungs, pancreas, spleen, fat, brain, muscle, small intestines, liver, bone, stomach, kidney, urinary bladder, and tumor were collected. Each organ was weighed and the tissue radioactivity was measured with an automated gamma counter (1282 Compugamma CS, Pharmacia/LKBNuclear, Inc., Mt. Waverly, Vic. Australia). The percentage of injected dose per gram of tissue (% ID/g) was calculated by comparison with samples of a standard dilution of the initial dose. All measurements were corrected for radioactive decay. Data were expressed as mean±standard deviation (SD). Prism software (GraphPAD, San Diego, Calif.) was used to determine statistical significance. Statistical significance was calculated using a paired t test. P-values <0.0001 were considered significant.

Biodistribution of [$^{64}$Cu]XYIMSR-06.

Mice bearing SK-RC-52 xenografts within the upper right flank were injected intravenously with 740 kBq (20 µCi) of [$^{64}$Cu]XYIMSR-06 in 200 µL of PBS. For in vivo competition (binding specificity) studies, tumor-bearing mice were injected with 740 kBq (20 µCi) of [$^{64}$Cu]XYIMSR-06 and 200 nmole of 8 in 200 µL of PBS concurrently. At specific times after injection (1 h, 4 h, 8 h and 24 h), mice (n=5) were sacrificed by cervical dislocation with blood immediately collected by cardiac puncture. Heart, lungs, pancreas, spleen, fat, brain, muscle, small intestines, liver, stomach, kidney, urinary bladder, and tumor were also collected. Each organ was weighed and the tissue radioactivity was measured with an automated gamma counter (1282 Compugamma CS, Pharmacia/LKBNuclear, Inc., Mt. Waverly, Vic. Australia). The percentage of injected dose per gram of tissue (% ID/g) was calculated by comparison with samples of a standard dilution of the initial dose. All measurements were corrected for radioactive decay. Data were expressed as mean±standard deviation (SD). Prism software (GraphPAD, San Diego, Calif.) was used to determine statistical significance. Statistical significance was calculated using a paired t test. P-values <0.0001 were considered significant.

Radio-Therapy of [$^{177}$Lu]XYIMSR-01.

Mice bearing SK-RC-52 xenografts at lower left flank were injected intravenously with PBS, 11.1 MBq (300 KO and 18.5 MBq (500 µCi) of [$^{177}$Lu]XYIMSR-01 in 200 µL of PBS (n=4). Size of the tumors was measured twice a week after the injection. Delays in tumor growth were observed from mice injected with [$^{177}$Lu]XYIMSR-01 in compared with control non-treated mice. The P-values were 0.042 and 0.031 for the 11.1 and 18/5 MBq doses, respectively.

Example 3

Results

Chemical synthesis of XYIMSR-01, XYIMSR-04, and XYIMSR-06 were achieved as in FIG. 5, FIG. 6, FIG. 12 and FIG. 15 respectively. Following a reported procedure, key intermediate 3 was obtained via solid support synthetic methods (Wichert et al., 2015). XYIMSR-01 has been generated by conjugating the commercially available DOTA-NHS ester with 3 in 82% yield. In(III) was incorporated into DOTA in nearly quantitative yield in 0.2 M NaOAc buffer at 60° C., providing the non-radiolabeled standard, [$^{113/115}$In]XYIMSR-01 (FIG. 7). After optimization, baseline separation between XYIMSR-01 and [$^{113/115}$In]XYIMSR-01 could be achieved by high performance liquid chromatography (HPLC). Lu(III) was incorporated into DOTA in excellent yield in 0.2 M NaOAc buffer at 60° C., providing the non-radiolabeled standard, [$^{175}$Lu]XYIMSR-01 (FIG. 9). After optimization, baseline separation between XYIMSR-01 and [$^{175}$Lu]XYIMSR-01 could be achieved by high performance liquid chromatography (HPLC). XYIMSR-04 has been generated by conjugating the commercially available NOTA-NHS ester with 3 in 52% yield. Al(III) was incorporated into NOTA in fair yield in 0.2 M NaOAc buffer at 60° C., providing the non-radiolabeled standard, [Al$^{19}$F]XYIMSR-04 (FIG. 13). After optimization, baseline separation between XYIMSR-04 and [Al$^{19}$F]XYIMSR-04 could be achieved by high performance liquid chromatography (HPLC). XYIMSR-06 has been generated by conjugating the commercially available p-SCN-Bn-NOTA with 3 in 83% yield. Cu(II) was incorporated into Bn-NOTA in fair yield in 0.2 M NaOAc buffer at 60° C., providing the non-radiolabeled standard, [$^{63/65}$Cu]XYIMSR-06 (FIG. 16). After optimization, baseline separation between XYIMSR-06 and [$^{63/65}$Cu]XYIMSR-06 could be achieved by high performance liquid chromatography (HPLC).

Fluorescein isothiocyanate (FITC)-labeled 8, as shown on FIG. 2A, has been synthesized as a standard to measure CAIX binding affinities of the corresponding radiotracers. Compound 8 bound specifically to CAIX-expressing SK-RC-52 cells, but not to CAIX-negative BxPC3 cells (FIG. 2B and FIG. 2C) (Rana et al., 2012; Wichert et al., 2015). In order to test the relative binding of XYIMSR-01 and [$^{113/115}$In]XYIMSR-01 to CAIX a competitive fluorescence polarization assay (Alquicer et al., 2012) for use with 8 has been modified. For the competitive binding assay, after optimization for background fluorescence, concentrations of 80 nM and 100 nM have been chosen for 8 and CAIX, respectively. As a positive control, non-fluorescent 3 has been employed, which has a reported $K_d$ value of 2.6 nM (Wichert et al., 2015). Increasing concentrations of 3, XYIMSR-01 and [$^{113/115}$In]XYIMSR-01 were incubated with CAIX for 30 min at room temperature. After 8 was added, fluorescence polarization signal was recorded. The IC$_{50}$ values determined for 3, XYIMSR-01 and [$^{113/115}$In]XYIMSR-01 were 75.9, 67.0, and 108.2 nM, respectively (FIG. 3A, FIG. 3B, and FIG. 3C). Using a similar method, the IC$_{50}$ value determined for 3, [$^{63/65}$Cu]XYIMSR-06, [Al$^{19}$F]XYIMSR-04, and [$^{175}$Lu]XYIMSR-01 were 63.6±2.8, 156.5±4.3 nM, 96.7±3.3 nM, and 122.4±3.8 nM (FIG. 4A, FIG. 4B, FIG. 4C and FIG. 3D). These findings suggest that the DOTA/NOTA-modified adducts were capable of binding CAIX with high affinity, on the order of positive control 3.

The capacity for [$^{111}$In]XYIMSR-01, [$^{177}$Lu]XYIMSR-01], [Al$^{18}$F] XYIMSR-04, and [$^{64}$Cu]XYIMSR-06, to detect CAIX-expressing tumors in vivo using PET or SPECT imaging was further investigated. The synthesis and purification of [$^{111}$In]XYIMSR-01 were achieved within 1.5 h in yield of 73.8-75.8% (n=3) and with specific radioactivities of 118.4-1021.2 GBq/µM (3,200-27,600 Ci/mmol). The synthesis and purification of [$^{177}$Lu]XYIMSR-01 was achieved within 1.5 h in yield of 69.0% with specific radioactivity of 2,340 Ci/mmol; 73.0% with specific radioactivity of 2239 Ci/mmol, and in average yield of 60% (n=12), with average specific activity of 1,900 Ci/mmol (ranging from 1,200 Ci/mmol to 2,500 Ci/mmol). The synthesis and purification of [Al$^{18}$F]XYIMSR-04, were achieved within 1.5 h in yield of 4.3% (n=3) and with specific radioactivity of 2.1-3.4 GBq/µM (57-92 Ci/mmol). The synthesis and purification of [$^{64}$Cu]XYIMSR-06, were achieved within 1.5 h in yield of 51.0±4.5% (n=5) and with specific radioactivities of 4.1-8.9 GBq/µM (110-240 Ci/mmol).

SPECT/CT Imaging of [$^{111}$In]XYIMSR-01.

[$^{111}$In]XYIMSR-01 was administered intravenously to two mice with SK-RC-52 flank tumors, followed by SPECT/CT. As shown in FIG. 17, radiotracer uptake was observed within the tumors at 1 h post-injection. By 24 h post-injection, nearly all the radioactivity in the kidneys and other organs had been eliminated, with tumor still retaining significant amounts of radiotracer. Image contrast improved even further by 48 h post-injection.

SPECT/CT Imaging of [$^{177}$Lu]XYIMSR-01.

[$^{177}$Lu]XYIMSR-01 was administered intravenously to mice with SK-RC-52 flank tumors, followed by SPECT/CT. [$^{177}$Lu]XYIMSR-01 exhibited CAIX specific uptake in vitro. As shown in FIG. 18, SPECT/CT imaging demonstrated tumor visualization by 1 h post-injection and achieved high signal contrast by 24 h.

PET/CT Imaging of [Al$^{18}$E]XYIMSR-04.

[Al$^{18}$F]XYIMSR-04 was administered intravenously to mice with SK-RC-52 flank tumors, followed by PET/CT. As shown in FIG. 19, PET/CT imaging demonstrated tumor visualization by 1 h post-injection.

PET/CT Imaging of [$^{64}$Cu]XYIMSR-06.

As shown in FIG. 20, the imaging findings closely matched the results of the biodistribution study (Table 3). At 1 h, tumor could be observed distinctly with additional visible signal in the kidneys and urinary bladder. Relatively selective tumor imaging could be achieved at 8 h with target selectivity continuing to improve by 24 h, with the SK-RC-52 ccRCC tumor xenografts as the only remaining visible radiotracer-avid structures. There was no significant background signal from blood or muscle. The liver did not retain significant radioactivity at any time.

Biodistribution of [$^{111}$In]XYIMSR-01.

Table 2 shows the biodistribution of [$^{111}$In]XYIMSR-01 at 1 h, 4 h, 8 h, 24 h and 48 h post-injection; results are expressed as the percentage injected dose per gram (% ID/g)

of tissue, n=5; block was done by simultaneously injecting 200 nmole of non-labeled 1 with [$^{111}$In]XYIMSR-01. Biodistribution confirmed tumor-selective uptake and retention of [$^{111}$In]XYIMSR-01 observed in imaging studies (Table 2). At 1 h post-injection, 26.0% ID/g of radiotracer uptake was observed within the tumor. Tumor/blood, and tumor/muscle ratios reached 19.7 and 12.7, respectively. Major non-specific organ uptake was observed in kidney, lung, stomach, small intestine and liver (Table 2).

Biodistribution studies conducted at later time points showed that the radiotracer continued to wash out from those organs while being retained within the tumor. At 24 h post-injection, tumor/blood and tumor/muscle ratios reached 178 and 68, respectively. Importantly, tumor/kidney ratio reached 1.7, suggesting that it might be possible to detect local ccRCC in the kidney at 24 h. The enhanced hydrophilicity of [$^{111}$In]XYIMSR-01, relative to the reported optical analog (Wichert et al., 2015), may have contributed to the low liver uptake. Tumor/liver ratio for [$^{111}$In]XYIMSR-01 and optical agent were 8.5 and 4.0 at 24 h, respectively (Wichert et al., 2015). All other organs showed tumor/organ ratio close to or higher than 10, indicating that good image contrast can be expected from these imaging agents. Biodistribution of [$^{111}$In]XYIMSR-01 simultaneously injected with non-radioactive competitor 8 at 24 h and 48 h post injection showed competitive inhibition of the uptake to tumors to 1% level (Table 2). The fast normal tissue clearance and the long lasting tumor retention may enable applications to radiopharmaceutical therapy with appropriately selected therapeutic radiometals.

TABLE 2

Biodistribution of [$^{111}$In]XYIMSR-01 at 1 h, 4 h, 8 h, 24 h and 48 h post-injection

| Organs | 1 hr | 4 hr | 8 hr | 24 hr | 24 hr + Block | 48 hr | 48 hr + Block |
|---|---|---|---|---|---|---|---|
| Blood | 1.34 ± 0.17 | 0.65 ± 0.06 | 0.48 ± 0.02 | 0.15 ± 0.02 | 0.03 ± 0.00 | 0.06 ± 0.02 | 0.03 ± 0.00 |
| Heart | 5.98 ± 0.53 | 2.91 ± 0.45 | 2.61 ± 0.35 | 1.16 ± 0.20 | 0.04 ± 0.01 | 0.84 ± 0.16 | 0.04 ± 0.01 |
| Lung | 45.85 ± 19.89 | 17.85 ± 3.55 | 17.39 ± 8.99 | 11.01 ± 3.71 | 0.12 ± 0.02 | 9.22 ± 1.25 | 0.09 ± 0.02 |
| Pancreas | 3.81 ± 0.72 | 1.54 ± 0.40 | 1.61 ± 0.28 | 0.69 ± 0.18 | 0.03 ± 0.00 | 0.59 ± 0.18 | 0.03 ± 0.01 |
| Spleen | 0.52 ± 0.04 | 0.51 ± 0.08 | 0.64 ± 0.07 | 0.69 ± 0.39 | 0.08 ± 0.01 | 0.67 ± 0.13 | 0.11 ± 0.03 |
| Fat | 1.03 ± 0.24 | 0.42 ± 0.22 | 0.45 ± 0.08 | 0.28 ± 0.19 | 0.02 ± 0.01 | 0.25 ± 0.08 | 0.03 ± 0.01 |
| Brain | 1.23 ± 1.10 | 0.45 ± 0.06 | 0.59 ± 0.09 | 0.71 ± 0.85 | 0.03 ± 0.00 | 0.41 ± 0.05 | 0.03 ± 0.01 |
| Muscle | 2.34 ± 2.19 | 1.01 ± 0.28 | 1.09 ± 0.15 | 0.35 ± 0.12 | 0.02 ± 0.00 | 0.39 ± 0.28 | 0.02 ± 0.00 |
| Small intestine | 9.37 ± 1.26 | 4.27 ± 0.69 | 4.31 ± 0.67 | 2.11 ± 0.33 | 0.08 ± 0.01 | 1.22 ± 0.44 | 0.08 ± 0.02 |
| Liver | 8.36 ± 0.73 | 4.00 ± 0.8 | 3.65 ± 0.65 | 3.02 ± 3.46 | 0.10 ± 0.02 | 1.65 ± 0.26 | 0.13 ± 0.04 |
| Stomach | 16.71 ± 2.46 | 7.91 ± 1.28 | 8.74 ± 1.26 | 3.31 ± 1.25 | 0.14 ± 0.02 | 1.82 ± 0.43 | 0.14 ± 0.03 |
| Kidney | 71.26 ± 8.74 | 41.52 ± 6.07 | 28.79 ± 21.35 | 15.29 ± 1.69 | 0.68 ± 0.14 | 8.78 ± 1.89 | 0.45 ± 0.09 |
| Bladder | 4.90 ± 4.96 | 2.68 ± 1.89 | 2.28 ± 0.51 | 0.74 ± 0.17 | 0.20 ± 0.07 | 0.38 ± 0.18 | 0.14 ± 0.03 |
| Tumor | 26.01 ± 5.74 | 20.83 ± 6.25 | 34.00 ± 15.16 | 25.62 ± 17.67 | 1.41 ± 0.20 | 13.92 ± 6.67 | 1.22 ± 0.54 |
| Tumor/Blood | 19.7 ± 4.8 | 31.9 ± 9.4 | 77.0 ± 32.5 | 178.1 ± 145.4 | 45.2 ± 9.7 | 212.0 ± 41.4 | 45.4 ± 13.8 |
| Tumor/Muscle | 12.7 ± 5.8 | 21.4 ± 7.2 | 34.2 ± 16.0 | 68.4 ± 29.0 | 91.4 ± 11.1 | 52.0 ± 21.0 | 75.1 ± 17.7 |
| Tumor/Kidney | 0.36 ± 0.06 | 0.50 ± 0.15 | 3.1 ± 3.1 | 1.7 ± 1.2 | 2.1 ± 0.3 | 1.5 ± 0.5 | 2.7 ± 0.8 |

Biodistribution of [$^{177}$Lu]XYIMSR-01.

Biodistribution studies confirmed the SPECT/CT data. Tumor-to-blood, muscle, and kidney ratios were 607.4±200.7, 128.4±25.4 and 4.5±1.4, respectively, at 24 h post-injection.

TABLE 3

Biodistribution of [$^{177}$Lu]XYIMSR-01

| Organs | 1 hr | 4 hr | 8 hr | 24 hr | 24 hr + Block | 48 hr | 48 hr + Block |
|---|---|---|---|---|---|---|---|
| Blood | 0.55 ± 0.06 | 0.18 ± 0.02 | 0.16 ± 0.05 | 0.02 ± 0.01 | 0.04 ± 0.02 | 0.04 ± 0.01 | 0.04 ± 0.07 |
| Heart | 3.59 ± 0.73 | 1.52 ± 0.54 | 1.49 ± 0.59 | 0.28 ± 0.14 | 0.08 ± 0.04 | 0.12 ± 0.17 | 0.04 ± 0.01 |
| Lung | 23.72 ± 6.49 | 10.35 ± 1.86 | 8.87 ± 3.30 | 1.48 ± 0.59 | 0.73 ± 0.58 | 0.90 ± 0.05 | 0.18 ± 0.05 |
| Pancreas | 2.03 ± 0.25 | 0.99 ± 0.19 | 1.03 ± 0.50 | 0.16 ± 0.07 | 0.05 ± 0.03 | 0.06 ± 0.01 | 0.02 ± 0.00 |
| Spleen | 0.29 ± 0.07 | 0.15 ± 0.03 | 0.29 ± 0.05 | 0.20 ± 0.07 | 0.38 ± 0.32 | 0.13 ± 0.04 | 0.15 ± 0.06 |
| Fat | 1.07 ± 0.58 | 0.56 ± 0.14 | 0.46 ± 0.17 | 0.05 ± 0.04 | 0.03 ± 0.03 | 0.03 ± 0.01 | 0.02 ± 0.01 |
| Brain | 0.49 ± 0.08 | 0.33 ± 0.04 | 0.44 ± 0.08 | 0.28 ± 0.10 | 0.04 ± 0.01 | 0.17 ± 0.03 | 0.02 ± 0.00 |
| Muscle (mm) | 1.42 ± 0.40 | 0.65 ± 0.19 | 0.47 ± 0.18 | 0.10 ± 0.05 | 0.03 ± 0.01 | 0.04 ± 0.01 | 0.01 ± 0.00 |
| Sm. intestine | 6.11 ± 0.68 | 2.64 ± 0.17 | 3.67 ± 0.93 | 0.96 ± 0.32 | 0.18 ± 0.07 | 0.20 ± 0.05 | 0.05 ± 0.01 |
| Liver | 4.15 ± 0.39 | 1.79 ± 0.44 | 1.87 ± 0.77 | 0.47 ± 0.21 | 0.46 ± 0.34 | 0.19 ± 0.03 | 0.23 ± 0.04 |
| Stomach | 12.20 ± 1.66 | 6.06 ± 1.57 | 6.15 ± 2.65 | 1.02 ± 0.56 | 0.21 ± 0.07 | 0.35 ± 0.04 | 0.09 ± 0.02 |
| Kidney (kid) | 40.77 ± 6.68 | 19.17 ± 2.82 | 18.99 ± 6.14 | 3.11 ± 1.59 | 1.54 ± 1.44 | 0.76 ± 0.11 | 0.39 ± 0.05 |
| Bladder | 26.55 ± 11.08 | 6.60 ± 3.66 | 6.00 ± 3.52 | 1.29 ± 1.10 | 0.73 ± 0.55 | 0.20 ± 0.01 | 0.28 ± 0.09 |
| Tumor | 26.91 ± 6.06 | 26.28 ± 4.25 | 27.48 ± 4.32 | 12.51 ± 3.02 | 1.70 ± 0.79 | 5.82 ± 2.14 | 0.65 ± 0.10 |
| Tumor/Blood | 47.9 ± 13.4 | 150.3 ± 34.6 | 178.6 ± 36.6 | 607.4 ± 200.7 | 42.0 ± 20.9 | 200.2 ± 101.7 | 42.7 ± 23.7 |
| Tumor/mm | 18.8 ± 5.0 | 43.7 ± 16.8 | 65.0 ± 19.0 | 128.4 ± 25.4 | 58.6 ± 25.3 | 141.5 ± 71.7 | 62.5 ± 34.5 |
| Tumor/kid | 0.6 ± 0.2 | 1.4 ± 0.4 | 1.5 ± 0.3 | 4.5 ± 1.4 | 1.4 ± 0.6 | 7.1 ± 1.8 | 1.7 ± 0.3 |

Biodistribution of [Al$^{18}$F]XYIMSR-04.

The biodistribution data at 1 h is shown in Table 4. The tumor uptake is 14.40% ID/g, with tumor-to-blood, -muscle and -kidney of 22.1, 9.74 and 0.28.

TABLE 4

Biodistribution of [Al$^{18}$F]XYIMSR-04

| Organs | 1 h (% ID/g) |
|---|---|
| Blood | 0.65 ± 0.11 |
| Heart | 5.03 ± 0.51 |
| Lung | 34.07 ± 5.85 |
| Pancreas | 3.47 ± 0.16 |
| Spleen | 0.54 ± 0.18 |
| Fat | 1.54 ± 0.25 |
| Brain | 0.66 ± 0.04 |
| Muscle (mm) | 1.74 ± 0.58 |
| Sm. intestine | 9.59 ± 1.04 |
| Liver | 5.55 ± 0.91 |
| Stomach | 21.62 ± 1.85 |
| Kidney (kid) | 50.84 ± 2.65 |
| Bladder | 20.12 ± 12.51 |
| Bone | 1.91 ± 1.39 |
| Tumor | 14.40 ± 2.18 |
| Tumor/Blood | 22.1 ± 1.5 |
| Tumor/mm | 9.74 ± 2.9 |
| Tumor/kid | 0.28 ± 0.03 |

Biodistribution of [$^{64}$Cu]XYIMSR-06.

Table 5 shows the radiotracer uptake in selected organs. Radiotracer uptake within tumor was 14.5% ID/g at 1 h with tumor-to-blood and muscle ratios >10. After the radiotracer reached a maximum of 19.3% ID/g in tumor at 4 h, it began to wash out from tumors slowly. By 24 h radioactivity within the tumors dropped to 6.2% ID/g. Compared with [$^{111}$In]XYIMSR-01 (20.8% ID/g at 4 h, 34.0% ID/g at 8 h, 25.6% ID/g at 24 h and 13.9% ID/g at 48 h)[33], [$^{64}$Cu]XYIMSR-06 demonstrated faster clearance, likely due to the more hydrophilic nature of NOTA-Cu(II), which has an additional non-coordinated free carboxylate not present for DOTA-In (III). At 8 h post-injection tumor signal was predominant, with kidney, lung and stomach as the only readily visible organs. Tumor-to-blood, muscle and kidney ratios were 129.6±18.8, 84.3±21.0 and 2.1±0.26, respectively. In principle those ratios would allow the detection of localized tumor in kidney. At 24 h, tumor-to-kidney and -lung ratios were further improved to 7.1 and 4.9, with all other tumor-to-organ ratios tested >10.0. Co-injection of 200 nmole of 8 along with [$^{64}$Cu]XYIMSR-06 blocked tumor uptake of the latter (Table 3) indicating specific, CAIX-mediated binding of this radiotracer. Within 24 h, no significant radiotracer uptake within liver was observed, indicative of the in vivo stability of NOTA-$^{64}$Cu chelation.

TABLE 5

Biodistribution of [$^{64}$Cu]XYIMSR-06

| Organs | 1 h | 4 h | 8 h | 8 h + block | 24 h | 24 h + block |
|---|---|---|---|---|---|---|
| Blood | 0.66 ± 0.05 | 0.33 ± 0.06 | 0.13 ± 0.02 | 0.08 ± 0.01 | 0.00 ± 0.06 | 0.01 ± 0.08 |
| Heart | 3.41 ± 0.79 | 1.78 ± 0.33 | 0.65 ± 0.10 | 0.16 ± 0.03 | 0.12 ± 0.03 | 0.08 ± 0.01 |
| Lung | 25.52 ± 3.35 | 12.03 ± 1.61 | 4.64 ± 0.58 | 0.77 ± 0.14 | 1.27 ± 0.38 | 0.29 ± 0.05 |
| Pancreas | 2.94 ± 0.24 | 1.36 ± 0.19 | 0.47 ± 0.21 | 0.14 ± 0.03 | 0.21 ± 0.29 | 0.07 ± 0.02 |
| Spleen | 0.36 ± 0.08 | 0.24 ± 0.04 | 0.18 ± 0.02 | 0.14 ± 0.02 | 0.09 ± 0.01 | 0.11 ± 0.04 |
| Fat | 0.80 ± 0.17 | 0.52 ± 0.29 | 0.28 ± 0.27 | 0.05 ± 0.01 | 0.03 ± 0.01 | 0.01 ± 0.01 |
| Brain | 1.46 ± 2.23 | 0.29 ± 0.06 | 0.24 ± 0.06 | 0.04 ± 0.01 | 0.13 ± 0.02 | 0.02 ± 0.01 |
| Muscle (mm) | 1.28 ± 0.27 | 0.70 ± 0.18 | 0.21 ± 0.05 | 0.05 ± 0.02 | 0.02 ± 0.01 | 0.04 ± 0.06 |
| Sm. intestine | 7.35 ± 0.78 | 4.15 ± 0.69 | 1.98 ± 0.14 | 0.38 ± 0.06 | 0.47 ± 0.03 | 0.19 ± 0.05 |
| Liver | 3.25 ± 0.97 | 2.18 ± 0.57 | 0.99 ± 0.22 | 0.55 ± 0.08 | 0.38 ± 0.03 | 0.42 ± 0.04 |
| Stomach | 14.80 ± 2.27 | 8.19 ± 0.97 | 4.02 ± 0.53 | 0.69 ± 0.18 | 0.65 ± 0.04 | 0.29 ± 0.04 |
| Kidney (kid) | 33.65 ± 3.91 | 19.99 ± 2.88 | 8.14 ± 1.15 | 1.82 ± 0.39 | 0.90 ± 0.12 | 0.48 ± 0.09 |
| Bladder | 11.12 ± 6.33 | 17.05 ± 8.86 | 7.43 ± 7.72 | 1.45 ± 1.53 | 0.34 ± 0.09 | 0.45 ± 0.50 |
| Tumor | 14.47 ± 2.69 | 19.31 ± 4.51 | 16.74 ± 1.58 | 2.39 ± 0.24 | 6.23 ± 1.41 | 1.20 ± 0.47 |
| Tumor/Blood | 21.9 ± 4.6 | 57.7 ± 9.3 | 129.6 ± 18.8 | 32.0 ± 3.8 | 142.6 ± 115.8 | 27.1 ± 26.7 |
| Tumor/mm | 10.8 ± 3.7 | 29.4 ± 9.9 | 84.3 ± 21.0 | 53.0 ± 12.6 | 261.3 ± 47.3 | 49.0 ± 28.7 |
| Tumor/kid | 0.4 ± 0.1 | 1.0 ± 0.1 | 2.1 ± 0.26 | 1.3 ± 10.2 | 7.1 ± 2.5 | 2.4 ± 0.4 |

Radio-Therapy of [$^{177}$Lu]YIMSR-01.

Delays in tumor growth were observed from mice injected with [$^{177}$Lu]XYIMSR-01 in compared with control non-treated mice. The P-values were 0.042 and 0.031 for the 11.1 and 18/5 MBq doses, respectively.

Example 4

Discussion

Recently, Wichert and co-workers (Wichert et al., 2015) identified 4,4-bis(4-hydroxyphenyl)valeric acid/acetazolamide as a dual-motif CAIX inhibitor, from a DNA-encoded chemical library (Krall et al., 2013; Franzini et al., 2014; Brenner and Lerner, 1992; Dower et al., 1993). The addition of a second binding motif significantly improved the potency of sulfonamide inhibitors (up to 40 times) (Wichert et al., 2015), while also suggesting a solution to the problem of generating an isoform-selective CAIX inhibitor caused by conserved structures at the active site. It has been hypothesized that the slow renal clearance and high liver uptake of the reported optical agent might derive from the hydrophobicity of the molecule. To improve the pharmacokinetics, the IRDye®750 portion of the molecule has been replaced with 1,4,7,10-tetraazacyclododecane-1,4,7,10-tetraacetic acid (DOTA), a more hydrophilic species that also enables convenient radiolabeling with metal isotopes for positron emission tomography (PET), single photon emission computed tomography (SPECT), and radiopharmaceutical therapy (Wadas et al., 2010; Cutler et al., 2013). Indium-111 has been chosen as the initial radionuclide for its relatively long half-life (2.8 day) to enable extended monitoring of pharmacokinetics.

Despite intensive effort expended in the development of CAIX inhibitors designed to engage only the active site, nuclear imaging analogs continued to demonstrate limited success, showing <2% ID/g within tumor and high radiotracer uptake within kidney and liver (Pan et al., 2014; Akurathi et al., 2010; Lu et al., 2013; Doss et al., 2014; Peeters et al., 2015). Peptides that bind to the surface of CAIX may provide an alternative solution to selective targeting, but they are limited by low potency and in vivo stability (Rana et al., 2012). Dual-motif ligands that may concurrently engage the CAIX active site and surface binding demonstrated high potency and tumor uptake for [$^{111}$In]XYIMSR-01, [$^{177}$Lu]XYIMSR-01, [Al$^{18}$F]XYIMSR-04, and [$^{64}$Cu]XYIMSR-06, and for the previously reported optical agent (Wichert et al., 2015). The hydrophilicity of these compounds, with multiple carboxylates and heteroatoms, improved non-targeted organ clearance, including that from kidney and liver.

In summary, highly potent and selective low-molecular-weight (LMW) ligands of carbonic anhydrase IX (CAIX) with a dual-targeting moiety were conjugated with metal chelators, metal complexes and fluorine prosthetic groups, enabling radio-labeling with a wide array of PET, SPECT and radiotherapeutic isotopes. As examples, a $^{111}$In labeled ligand ([$^{111}$In]XYIMSR-01) a $^{177}$Lu labeled ligand ([$^{177}$Lu]XYIMSR-01), a $^{18}$F labeled ligand ([Al$^{18}$F]XYIMSR-04), and a $^{64}$Cu labeled ligand ([$^{64}$Cu]XYIMSR-06), were successfully synthesized in high yield and purity. These compounds were then injected into mice bearing CA IX+ tumors (SK-RC-52) and allowed for successful imaging with rapid uptake and minimum non-specific organ uptake. In addition, [$^{111}$In]XYIMSR-01 showed long lasting tumor residence, and also demonstrates improved pharmacokinetics, with fast clearance from non-targeted tissues, including kidney. Further, PET imaging ligands, such as [$^{64}$Cu]XYIMSR-06 and [Al$^{18}$F]XYIMSR-04, enabled detecting CAIX expressing tumor in higher sensitivity and resolution. Moreover, the structure modifications on [$^{64}$Cu]XYIMSR-06 and [$^{177}$Lu]XYIMSR-01 enabled significant improvement on in vivo pharmacokinetics for both imaging and therapy applications.

Finally, [$^{177}$Lu]XYIMSR-01 showed significant therapeutic effect in controlling tumor growth.

Radioisotope labeled CA IX targeting agents stand to enable a wide range of imaging and therapeutic applications, including but not limited to renal cell carcinoma (RCC). Based on the structural similarity of the ligands synthesized, kinetic data of these ligands could help to predict the in vivo properties of other PET/SPECT/radiotherapeutic isotope labeled ligands. These analogs of [$^{111}$In]XYIMSR-01, [$^{177}$Lu]XYIMSR-01, [Al$^{18}$F]XYIMSR-04 and [$^{64}$Cu]XY-IMSR-06, with other radiometals should allow for their use in other nuclear imaging modalities and targeted radiopharmaceutical therapy, including but not limited to renal cell carcinoma (RCC).

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

Akurathi V, Dubois L, Lieuwes N G, Chitneni S K, Cleynhens B J, Vullo D, Supuran C T, Verbruggen A M, Lambin P and Bormans G M. Synthesis and biological evaluation of a 99mTc-labelled sulfonamide conjugate for in vivo visualization of carbonic anhydrase IX expression in tumor hypoxia. Nuclear medicine and biology. 2010; 37(5):557-564.

Alauddin M M. Positron emission tomography (PET) imaging with (18)F-based radiotracers. Am J Nucl Med Mol Imaging. 2012; 2:55-76. PMID:23133802.

Alquicer G, Sedlak D, Byun Y, Pavlicek J, Stathis M, Rojas C, Slusher B, Pomper M G, Bartunek P and Barinka C. Development of a high-throughput fluorescence polarization assay to identify novel ligands of glutamate carboxypeptidase II. Journal of biomolecular screening. 2012; 17(8):1030-1040.

Alterio V, Di Fiore A, D'Ambrosio K, Supuran C T and De Simone G. Multiple binding modes of inhibitors to carbonic anhydrases: how to design specific drugs targeting 15 different isoforms? Chemical reviews. 2012; 112(8): 4421-4468.

Askoxylakis V, Garcia-Boy R, Rana S, Krämer S, Hebling U, Mier W, Altmann A, Markert A, Debus J, Haberkorn U. A new peptide ligand for targeting human carbonic anhydrase IX, identified through the phage display technology. PLoS One. 2010; 5:e15962. PMCID:PMC3013143.

Atkins M, Regan M, McDermott D, Mier J, Stanbridge E, Youmans A, Febbo P, Upton M, Lechpammer M and Signoretti S. Carbonic anhydrase IX expression predicts outcome of interleukin 2 therapy for renal cancer. Clinical cancer research: an official journal of the American Association for Cancer Research. 2005; 11(10):3714-3721.

Bao B, Groves K, Zhang J, Handy E, Kennedy P, Cuneo G, Supuran C T, Yared W, Rajopadhye M, Peterson. In vivo imaging and quantification of carbonic anhydrase IX expression as an endogenous biomarker of tumor hypoxia. PLoS One. 2012; 7:e50860 PMCID:PMC3511310.

Brenner S and Lerner R A. Encoded combinatorial chemistry. Proceedings of the National Academy of Sciences of the United States of America. 1992; 89(12):5381-5383.

Bui M H, Seligson D, Han K R, Pantuck A J, Dorey F J, Huang Y, Horvath S, Leibovich B C, Chopra S, Liao S Y, Stanbridge E, Lerman M I, Palotie A, Figlin R A and Belldegrun A S. Carbonic anhydrase IX is an independent predictor of survival in advanced renal clear cell carcinoma: implications for prognosis and therapy. Clinical cancer research: an official journal of the American Association for Cancer Research. 2003; 9(2):802-811.

Cecchi A, Hulikova A, Pastorek J, Pastorekova S, Scozzafava A, Winum J Y, Montero J L, Supuran C T. Carbonic anhydrase inhibitors. Design of fluorescent sulfonamides as probes of tumor-associated carbonic anhydrase IX that inhibit isozyme IX-mediated acidification of hypoxic tumors. J Med Chem. 2005; 48:4834-41. PMID: 16033263.

Chen Z Y, Wang Y X, Lin Y, Zhang J S, Yang F, Zhou Q L, Liao Y Y. Advance of molecular imaging technology and targeted imaging agent in imaging and therapy. Biomed Res Int. 2014; 2014: 819324. PMCID: PMC3943245.

Cho S Y, Gage K L, Mease R C, Senthamizhchelvan S, Holt D P, Jeffrey-Kwanisai A, Endres C J, Dannals R F, Sgouros G, Lodge M, Eisenberger M A, Rodriguez R, Carducci M A, Rojas C, Slusher B S, Kozikowski A P, et al. Biodistribution, tumor detection, and radiation dosimetry of 18F-DCFBC, a low-molecular-weight inhibitor of prostate-specific membrane antigen, in patients with metastatic prostate cancer. Journal of nuclear medicine: official publication, Society of Nuclear Medicine. 2012; 53(12):1883-1891.

Christianson D W, Fierke C A. Carbonic anhydrase: evolution of the zinc binding site by nature and by design. Acc. Chem. Res. 1996; 29: 331.

Clare B W and Supuran C T. A perspective on quantitative structure-activity relationships and carbonic anhydrase inhibitors. Expert opinion on drug metabolism & toxicology. 2006; 2(1):113-137.

Coenen H H, Elsinga P H, Iwata R, Kilbourn M R, Pillai M R, Rajan M G, Wagner H N, Jr. and Zaknun J J. Fluorine-18 radiopharmaceuticals beyond [18F]FDG for use in oncology and neurosciences. Nuclear medicine and biology. 2010; 37(7):727-740.

Cutler C S, Hennkens H M, Sisay N, Huclier-Markai S and Jurisson S S. Radiometals for combined imaging and therapy. Chemical reviews. 2013; 113(2):858-883.

Doss M, Kolb H C, Walsh J C, Mocharla V P, Zhu Z, Haka M, Alpaugh R K, Chen D Y and Yu J Q. Biodistribution and radiation dosimetry of the carbonic anhydrase IX imaging agent [(18) F]VM4-037 determined from PET/CT scans in healthy volunteers. Molecular imaging and biology:MIB:the official publication of the Academy of Molecular Imaging. 2014; 16(5):739-746.

Dower W J, Barrett, R. W., Gallop, M. A., Needels, M. C. (1993). Method of synthesizing diverse collections of oligomers.

Franzini R M, Neri D and Scheuermann J. DNA-encoded chemical libraries: advancing beyond conventional small-molecule libraries. Accounts of chemical research. 2014; 47(4):1247-1255.

Gossage L, Eisen T, Maher E R. VHL, the story of a tumour suppressor gene. Nat Rev Cancer. 2015 January; 15(1): 55-64.

Grabmaier K, M C AdW, Verhaegh G W, Schalken J A and Oosterwijk E. Strict regulation of CAIX (G250/MN) by HIF-1alpha in clear cell renal cell carcinoma. Oncogene. 2004; 23(33):5624-5631.

Groves K, Bao B, Zhang J, Handy E, Kennedy P, Cuneo G, Supuran C T, Yared W, Peterson J D, Rajopadhye M. Synthesis and evaluation of near-infrared fluorescent sulfonamide derivatives for imaging of hypoxia-induced carbonic anhydrase IX expression in tumors. Bioorg Med Chem Lett. 2012; 22:653-7. PMID:22079760.

Håkansson K, Carlsson M, Svensson L A, Liljas A. Structure of native and apo carbonic anhydrase II and structure of some of its anion-ligand complexes. J Mol Biol. 1992; 227:1192-204.

Ivanov S, Liao S Y, Ivanova A, Danilkovitch-Miagkova A, Tarasova N, Weirich G, Merrill M J, Proescholdt M A, Oldfield E H, Lee J, Zavada J, Waheed A, Sly W, Lerman M I and Stanbridge E J. Expression of hypoxia-inducible cell-surface transmembrane carbonic anhydrases in human cancer. The American journal of pathology. 2001; 158(3):905-919.

Krall N, Scheuermann J and Neri D. Small targeted cytotoxics: current state and promises from DNA-encoded chemical libraries. Angewandte Chemie. 2013; 52(5): 1384-1402.

Krall N, Pretto F, Decurtins W, Bernardes G J, Supuran C T, Neri D. A small-molecule drug conjugate for the treatment of carbonic anhydrase IX expressing tumors. Angew Chem Int Ed Engl. 2014; 53(16): 4231-5. PMID: 24623670.

Krishnamurthy V M, Kaufman G K, Urbach A R, Gitlin I, Gudiksen K L, Weibel D B, Whitesides G M. Carbonic anhydrase as a model for biophysical and physical-organic studies of proteins and protein-ligand binding. Chem Rev. 2008; 108:946-1051. PMCID:PMC2740730.

Leibovich B C, Sheinin Y, Lohse C M, Thompson R H, Cheville J C, Zavada J and Kwon E D. Carbonic anhydrase IX is not an independent predictor of outcome for patients with clear cell renal cell carcinoma. Journal of clinical oncology: official journal of the American Society of Clinical Oncology. 2007; 25(30):4757-4764.

Lindskog S. Structure and mechanism of carbonic anhydrase. Pharmacol Ther. 1997; 74:1-20. PMID:9336012.

Lipworth L, Morgans A K, Edwards T L, Barocas D A, Chang S S, Herrell S D, Penson D F, Resnick M J, Smith J A and Clark P E. Renal cell cancer histologic subtype distribution differs by race and sex. BJU international. 2014.

Lu G, Hillier S M, Maresca K P, Zimmerman C N, Eckelman W C, Joyal J L and Babich J W. Synthesis and SAR of novel Re/99mTc-labeled benzenesulfonamide carbonic anhydrase IX inhibitors for molecular imaging of tumor hypoxia. Journal of medicinal chemistry. 2013; 56(2): 510-520.

Oosterwijk E, Ruiter D J, Hoedemaeker P J, Pauwels E K, Jonas U, Zwartendijk J and Warnaar S O. Monoclonal antibody G 250 recognizes a determinant present in renal-cell carcinoma and absent from normal kidney. International journal of cancer Journal international du cancer. 1986; 38(4):489-494.

Pan J, Lau J, Mesak F, Hundal N, Pourghiasian M, Liu Z, Benard F, Dedhar S, Supuran C T and Lin K S. Synthesis and evaluation of 18F-labeled carbonic anhydrase IX inhibitors for imaging with positron emission tomography. Journal of enzyme inhibition and medicinal chemistry. 2014; 29(2):249-255.

Pichler M, Hutterer G C, Chromecki T F, Jesche J, Kampel-Kettner K, Eberhard K, Hoefler G, Pummer K and Zigeuner R. Trends of stage, grade, histology and tumour necrosis in renal cell carcinoma in a European centre surgical series from 1984 to 2010. Journal of clinical pathology. 2012; 65(8):721-724.

Peeters S G, Dubois L, Lieuwes N G, Laan D, Mooijer M, Schuit R C, Vullo D, Supuran C T, Eriksson J, Windhorst A D and Lambin P. [F]VM4-037 MicroPET Imaging and Biodistribution of Two In Vivo CAIX-Expressing Tumor Models. Molecular imaging and biology:MIB:the official publication of the Academy of Molecular Imaging. 2015.

Potter C and Harris A L. Hypoxia inducible carbonic anhydrase IX, marker of tumour hypoxia, survival pathway and therapy target. Cell cycle. 2004; 3(2):164-167. Rana S, Nissen F, Man A, Markert A, Altmann A, Mier W, Debus J, Haberkorn U and Askoxylakis V. Optimization of a novel peptide ligand targeting human carbonic anhydrase IX. PloS one. 2012; 7(5):e38279.

Rana S, Nissen F, Marr A, Markert A, Altmann A, Mier W, Debus J, Haberkorn U, Askoxylakis V. Optimization of a novel peptide ligand targeting human carbonic anhydrase IX. PLoS One. 2012; 7:e38279. PMCID:PMC3365038.

Reilly R M, Lam K, Chan C and Levine M. Advancing Novel Molecular Imaging Agents from Preclinical Studies to First-in-Humans Phase I Clinical Trials in Academia-A Roadmap for Overcoming Perceived Barriers. Bioconjugate chemistry. 2015; 26(4):625-632.

Shuch B, Amin A, Armstrong A J, Eble J N, Ficarra V, Lopez-Beltran A, Martignoni G, Rini B I and Kutikov A. Understanding pathologic variants of renal cell carcinoma: distilling therapeutic opportunities from biologic complexity. European urology. 2015; 67(1):85-97.

Siegel R L, Miller K D and Jemal A. Cancer statistics, 2015. CA: a cancer journal for clinicians. 2015; 65(1):5-29.

Smaldone M C, Chen D Y, Yu J Q and Plimack E R. Potential role of (124)I-girentuximab in the presurgical diagnosis of clear-cell renal cell cancer. Biologics: targets & therapy. 2012; 6:395-407.

Srigley J R, Delahunt B, Eble J N, Egevad L, Epstein J I, Grignon D, Hes O, Moch H, Montironi R, Tickoo S K, Zhou M, Argani P and Panel IRT. The International Society of Urological Pathology (ISUP) Vancouver Classification of Renal Neoplasia. The American journal of surgical pathology. 2013; 37(10):1469-1489.

Supuran C T. Carbonic anhydrases: novel therapeutic applications for inhibitors and activators. Nature reviews Drug discovery. 2008; 7(2):168-181.

Umbreit E C, Shimko M S, Childs M A, Lohse C M, Cheville J C, Leibovich B C, Blute M L and Thompson R H. Metastatic potential of a renal mass according to original tumour size at presentation. BJU international. 2012; 109(2):190-194; discussion 194.

Uzzo R G, Russo P, Chen D, et al. The multicenter phase III Redect trial: a comparative study of 124 I-girentuximab-PET/CT versus diagnostic CT for the pre-operative diagnosis of clear cell renal cell carcinoma (ccRCC) [late-breaking abstract]. AUA Annual Meeting; May 29-Jun. 3 2010; San Francisco, Calif., USA.

Wichert M, Krall N, Decurtins W, Franzini R M, Pretto F, Schneider P, Neri D and Scheuermann J. Dual-display of small molecules enables the discovery of ligand pairs and facilitates affinity maturation. Nature chemistry. 2015; 7(3):241-249.

Wadas T J, Wong E H, Weisman G R and Anderson C J. Coordinating radiometals of copper, gallium, indium, yttrium, and zirconium for PET and SPECT imaging of disease. Chemical reviews. 2010; 110(5):2858-2902.

Youn H., Hong K. In vivo noninvasive small animal molecular imaging. Osong Public Health Res Perspect. 2012; 3:48-59. PMCID: PMC3738683.

Cancer Genome Atlas Research Network. Comprehensive molecular characterization of clear cell renal cell carcinoma. Nature. 2013 Jul. 4; 499(7456):43-9.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound of formula (I):

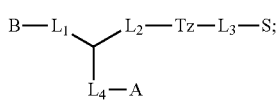

wherein:
- B is a metal chelating moiety optionally comprising a metal or a radiometal, or a halogenated or radiohalogenated prosthetic group;
- $L_1$, $L_2$, $L_3$, and $L_4$ are —$C_1$-$C_{24}$ alkyl-, wherein each alkyl group is optionally substituted with one to four groups selected from the group consisting of =O, =S, and —COOR and one to six of the methylene groups in each alkyl group is optionally replaced by —O—, —S—, or —(NR')—, provided that no two adjacent methylene groups are both replaced by —O—, —S—, or —(NR')—;
- each R and R' is independently selected from the group consisting of hydrogen, $C_1$-$C_6$ alkyl, $C_2$-$C_{12}$ aryl, and $C_4$-$C_{16}$ alkyl aryl;
- Tz is a triazole group selected from the group consisting of

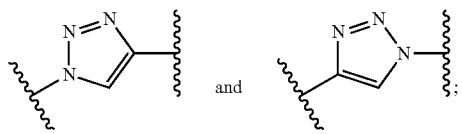 [SMILES: *c1cn(*)nn1 ; *c1cn(*)nn1]

S is a sulfonamide selected from the group consisting of:

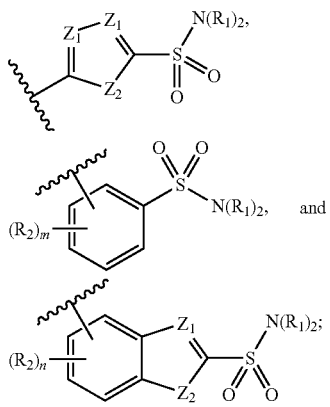

each $R_1$ is independently selected from the group consisting of hydrogen, substituted or unsubstituted alkyl, substituted and unsubstituted aryl, and substituted and unsubstituted heteroaryl;

each $R_2$ is selected from the group consisting of hydrogen, halogen, hydroxyl, alkoxyl, —CN, —$CF_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl;

m is an integer selected from the group consisting of 1, 2, 3, and 4;

n is an integer selected from the group consisting of 1, 2, and 3;

each $Z_1$ is independently selected from the group consisting of $CR_3$, and N;

each $Z_2$ is independently selected from the group consisting of $CR_3$, and S;

each $R_3$ is independently selected from the group consisting of hydrogen, halogen, hydroxyl, alkoxyl, —CN, —$CF_3$, amino, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl;

A is

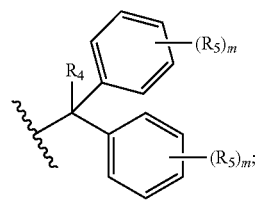

$R_4$ is independently selected from the group consisting of hydrogen, hydroxyl, alkoxyl, substituted or unsubstituted alkyl, substituted or unsubstituted alkenyl, and substituted or unsubstituted alkynyl;

$R_5$ is independently selected from the group consisting of hydrogen, halogen, hydroxyl, alkoxyl, —CN, —$CF_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl;

or a pharmaceutically acceptable salt thereof.

2. The compound of claim 1, wherein the compound of formula (I) is a compound of formula (II):

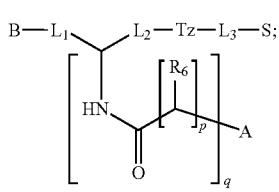

(II)

wherein:
  p is an integer selected from the group consisting of 0, 1, 2, 3, and 4;
  q is an integer selected from the group consisting of 1, 2, 3, and 4;
  each $R_6$ is independently selected from the group consisting of H and COOR;
  wherein R is independently selected from the group consisting of hydrogen, $C_1$-$C_6$ alkyl, $C_6$-$C_{12}$ aryl, and $C_4$-$C_{16}$ alkyl aryl
  or a pharmaceutically acceptable salt thereof.

3. The compound of claim 2, wherein the compound of formula (II) is a compound of formula (III):

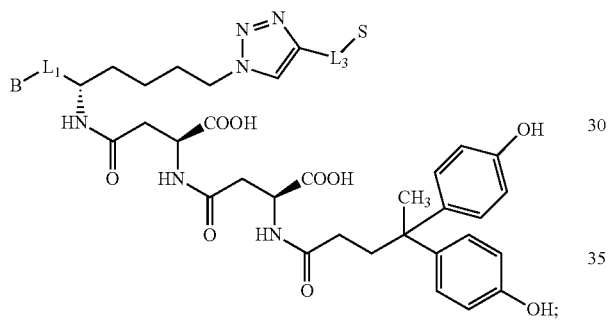

(III)

or a pharmaceutically acceptable salt thereof.

4. The compound of claim 1, wherein S is selected from the group consisting of:

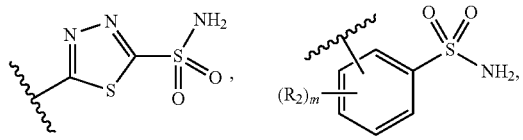

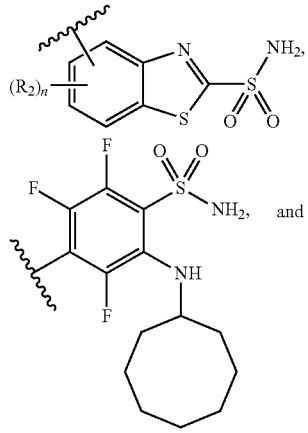

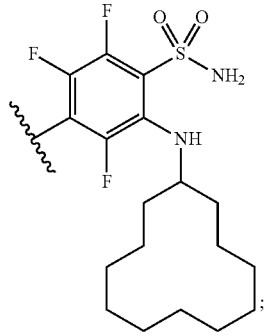

or a pharmaceutically acceptable salt thereof.

5. The compound of claim 1, wherein B is a metal chelating moiety optionally comprising a metal or a radiometal selected from the group of:

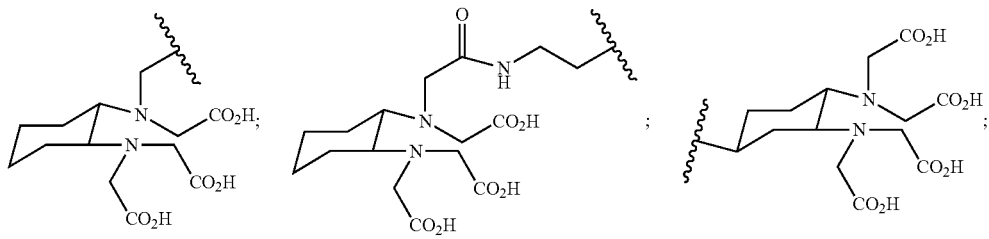

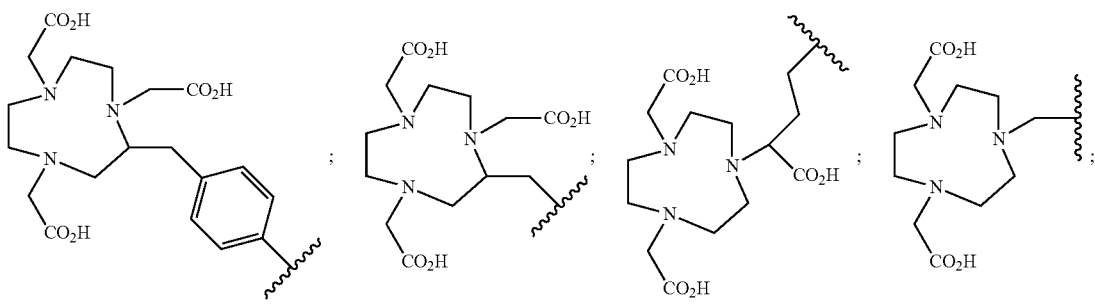

-continued
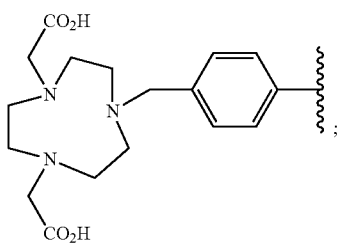
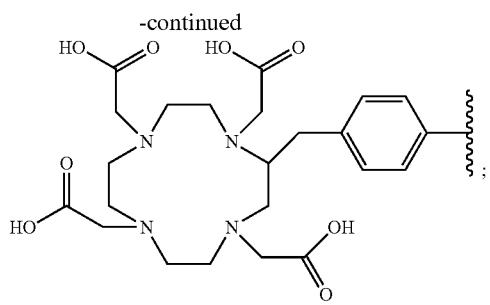
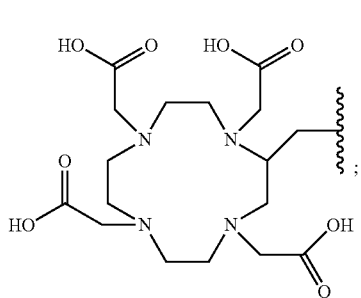
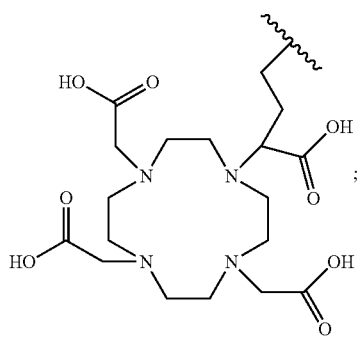
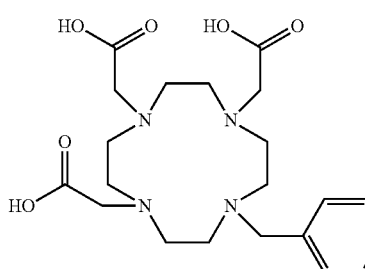
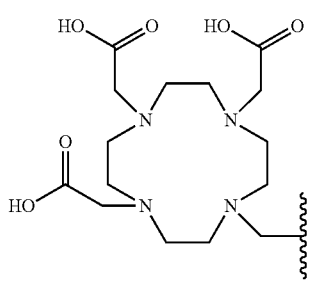
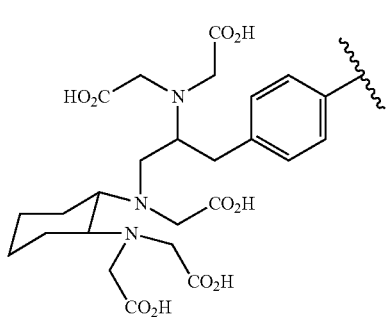
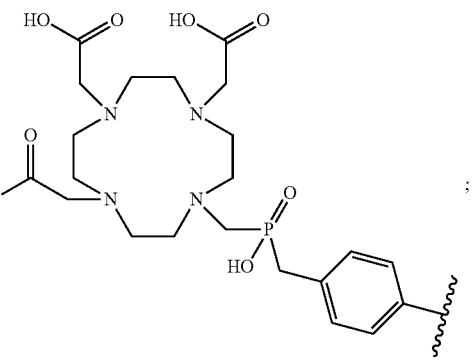
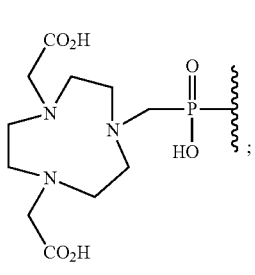
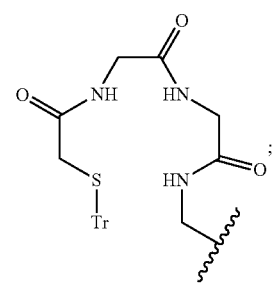
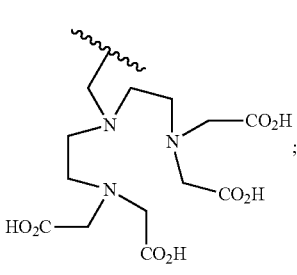

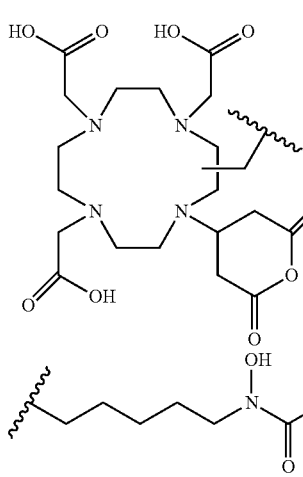
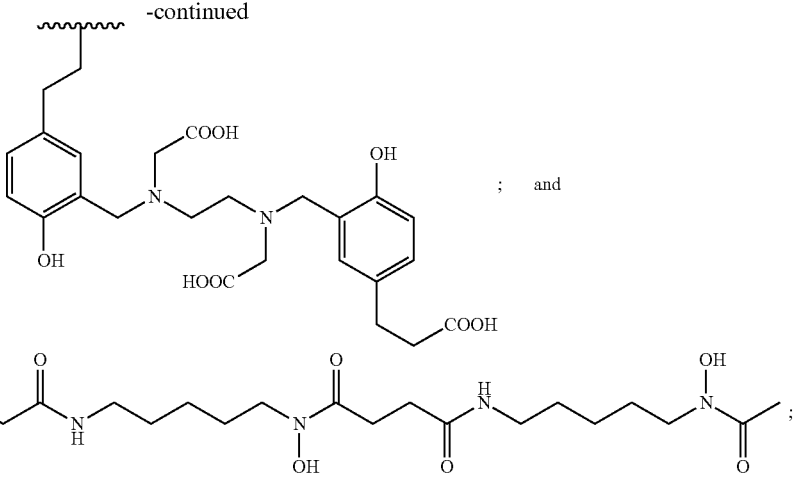
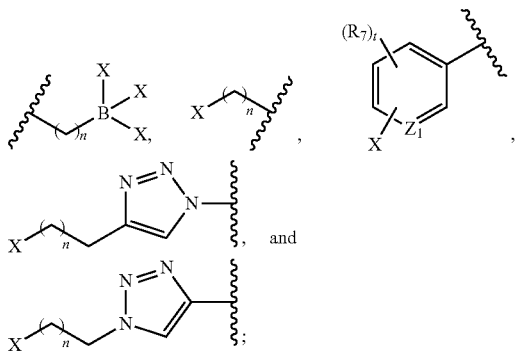

or wherein B is a halogenated or radio-halogenated prosthetic group selected from the group consisting of:

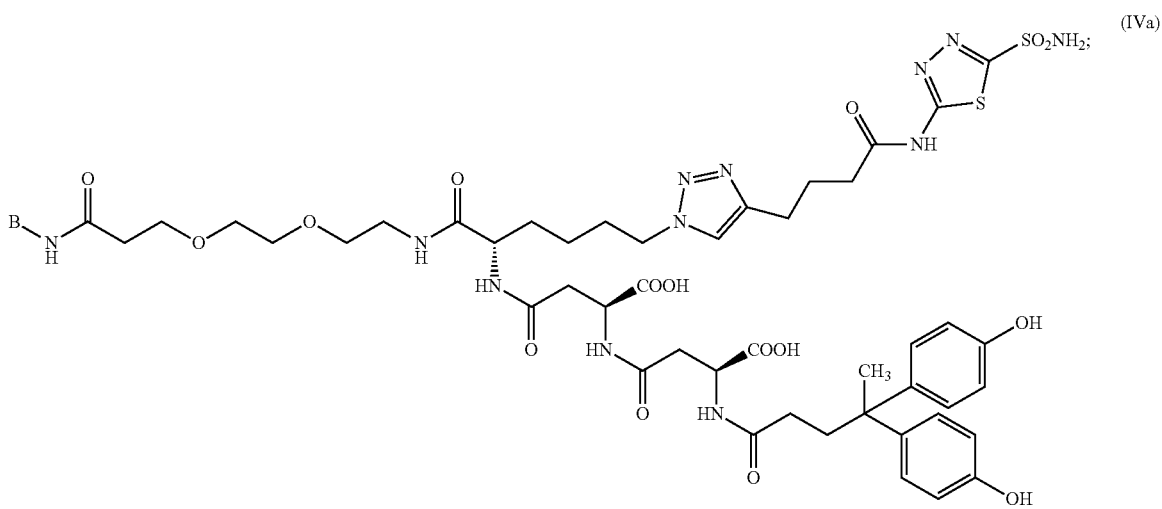

wherein:
X is a halogen or a radio-halogen;
n is an integer selected from the group consisting of 1, 2, 3, 4, 5 and 6;
t is an integer selected from the group consisting of 1, 2, and 3;
$Z_1$ is independently selected from the group consisting of $CR_3$, and N;
each $R_3$ and $R_7$ is selected from the group consisting of hydrogen, halogen, hydroxyl, alkoxyl, —CN, —$CF_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl;
or a pharmaceutically acceptable salt thereof.

6. The compound of claim 5, wherein the metal chelating agent comprises a metal selected from the group consisting of: Y, Lu, Tc, Zr, In, Sm, Re, Cu, Pb, Ac, Bi, Al, Ga, Re, Ho and Sc.

7. The compound of claim 5, wherein the metal is a radiometal and is selected from the group consisting of: $^{67}$Ga, $^{68}$Ga, $^{64}$Cu, $^{67}$Cu, Al-$^{18}$F, $^{86}$Y, $^{90}$Y, $^{89}$Zr, $^{111}$In, $^{99m}$Tc, $^{177}$Lu, $^{153}$Sm, $^{186}$Re, $^{188}$Re, $^{203}$Pb, $^{212}$Pb, $^{225}$Ac, $^{212}$Bi, $^{213}$Bi, $^{47}$Sc, and $^{166}$Ho.

8. The compound of claim 5, wherein the halogen is selected from the group consisting of: F, Br, I, and At.

9. The compound of claim 5, wherein the radio-halogen is selected from the group consisting of: $^{18}$F, $^{76}$Br, $^{77}$Br, $^{80m}$Br, $^{125}$I, $^{124}$I, $^{131}$I, and $^{211}$At.

10. The compound of claim 1, wherein the compound of formula (I) is selected from the group consisting of:

-continued
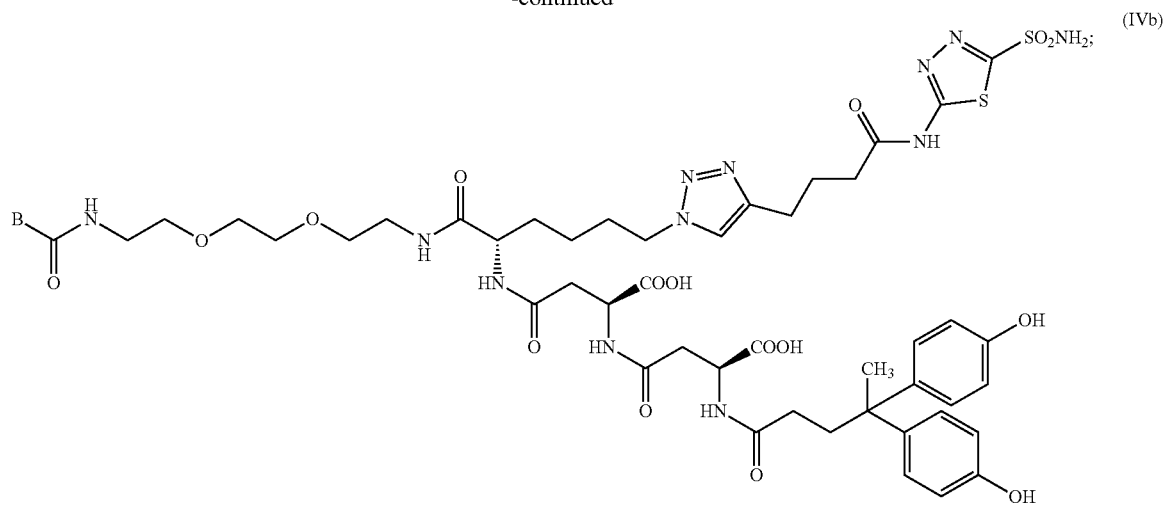
(IVb)
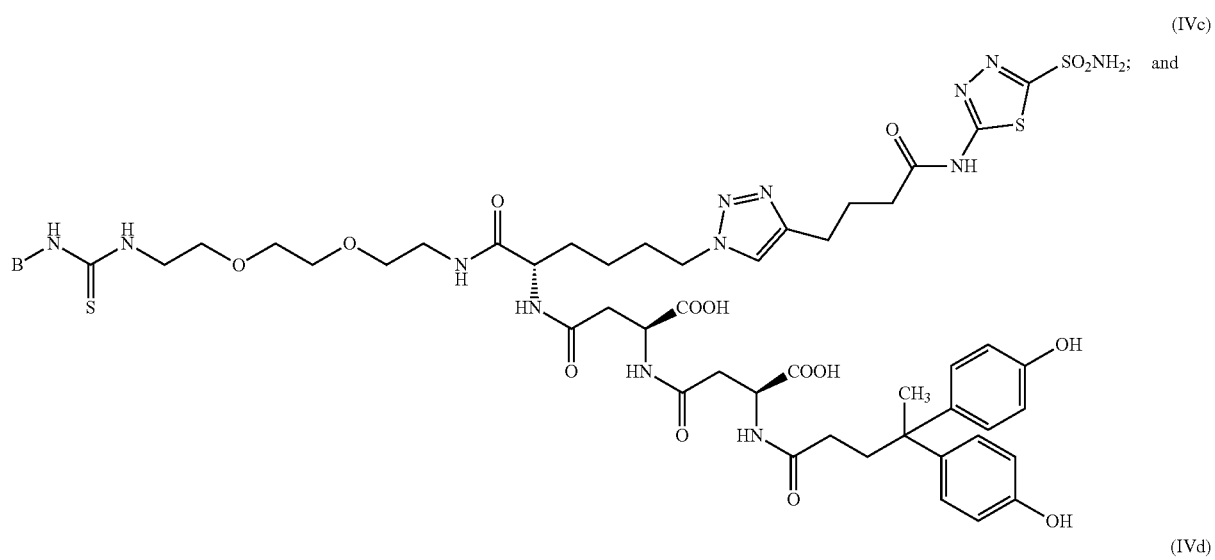
(IVc) and
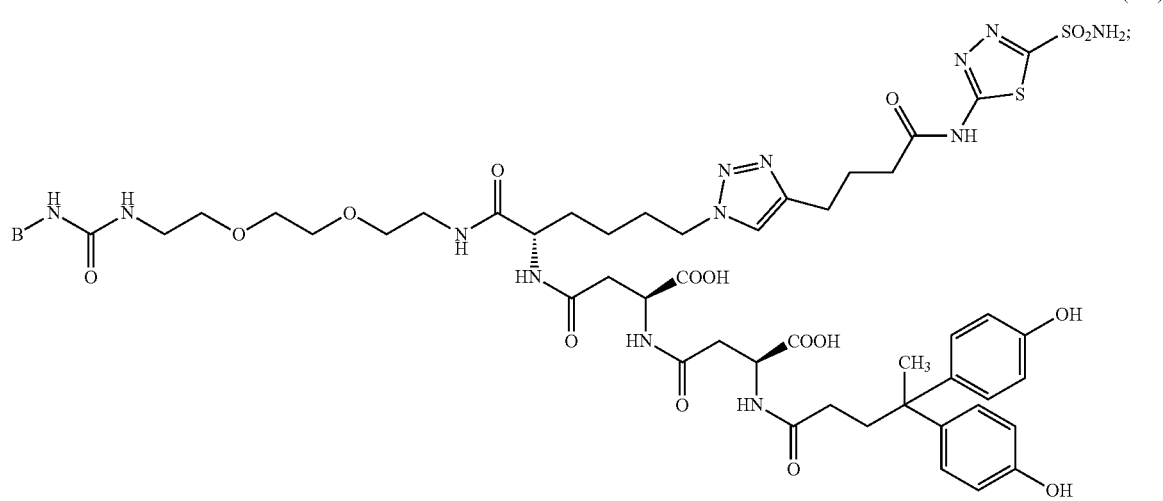
(IVd)
or a pharmaceutically acceptable salt thereof.
11. The compound of claim 1, wherein the compound of formula (I) is selected from the group consisting of:

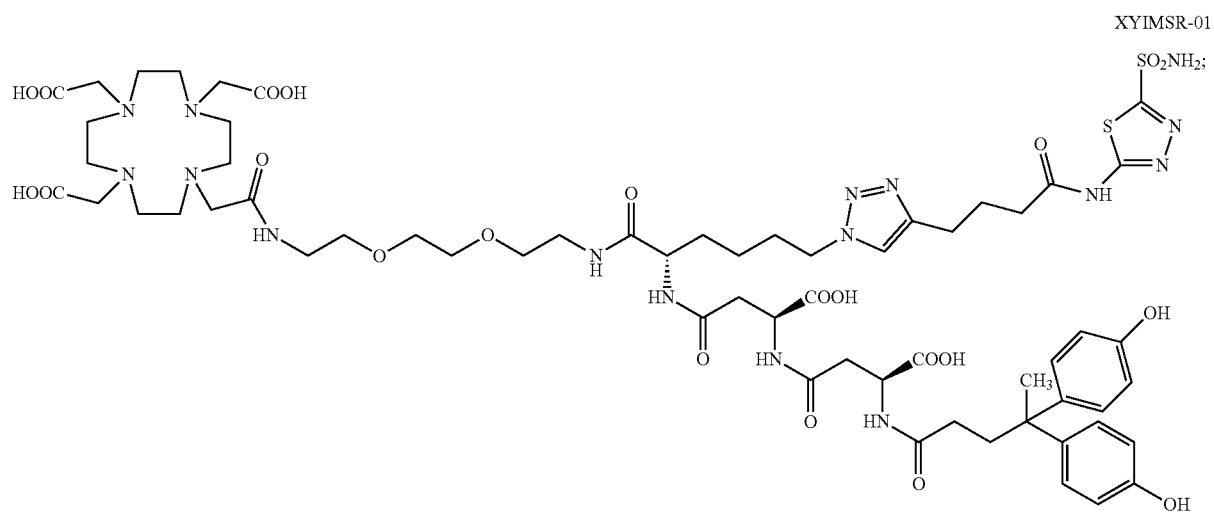
XYIMSR-01
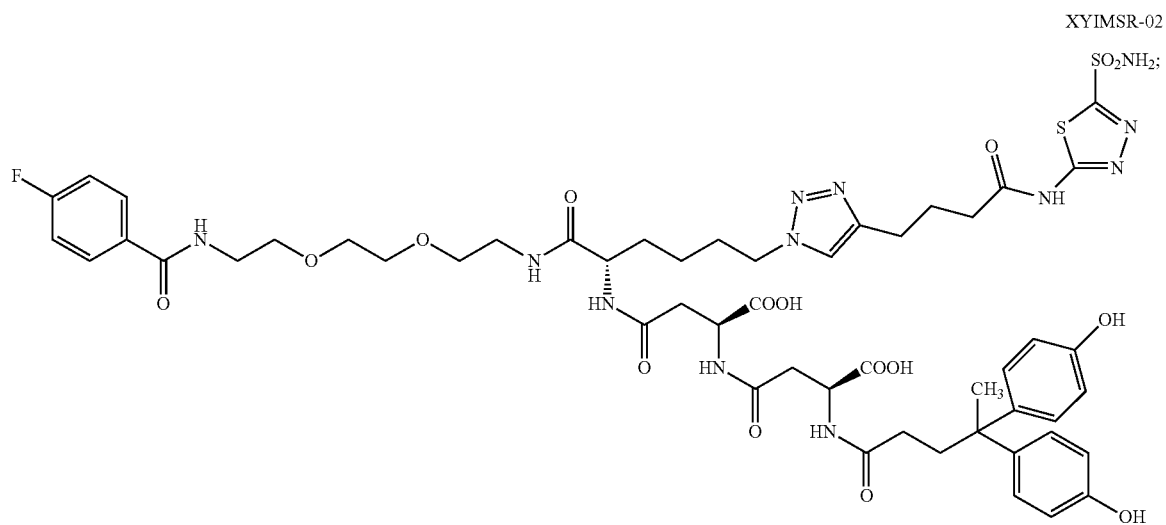
XYIMSR-02
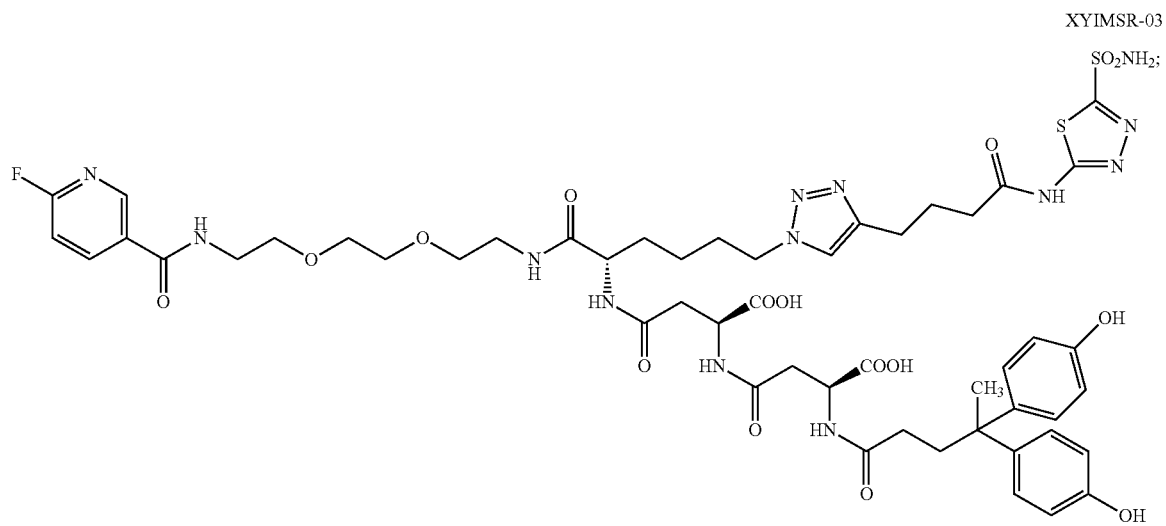
XYIMSR-03

-continued
XYIMSR-04
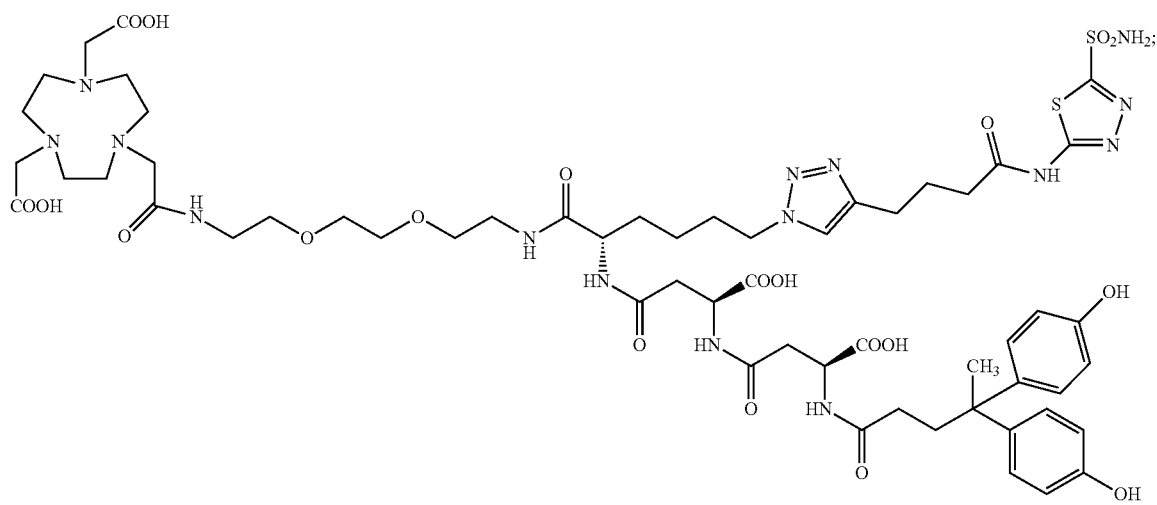
XYIMSR-05
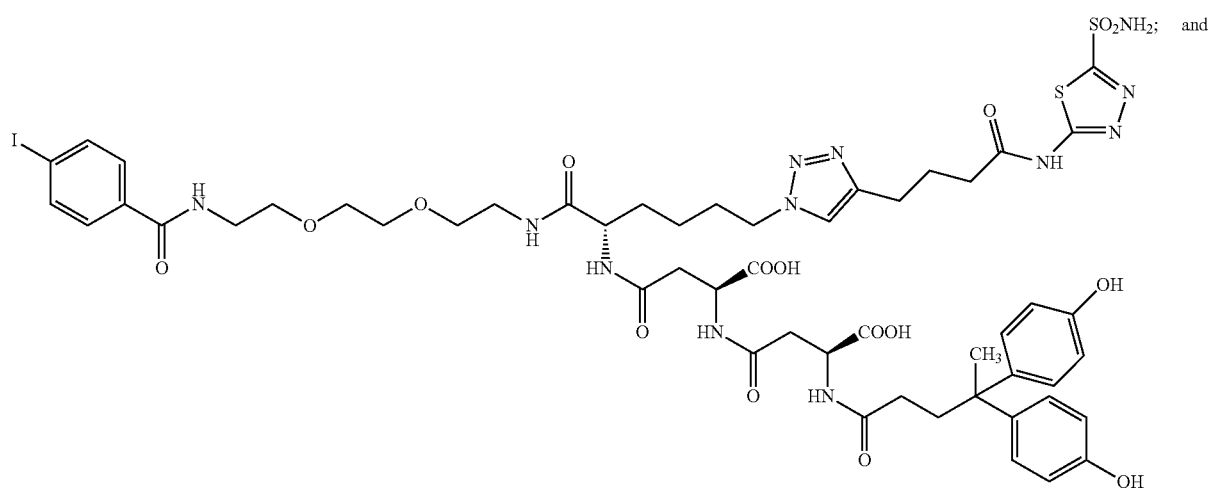
XYIMSR-06
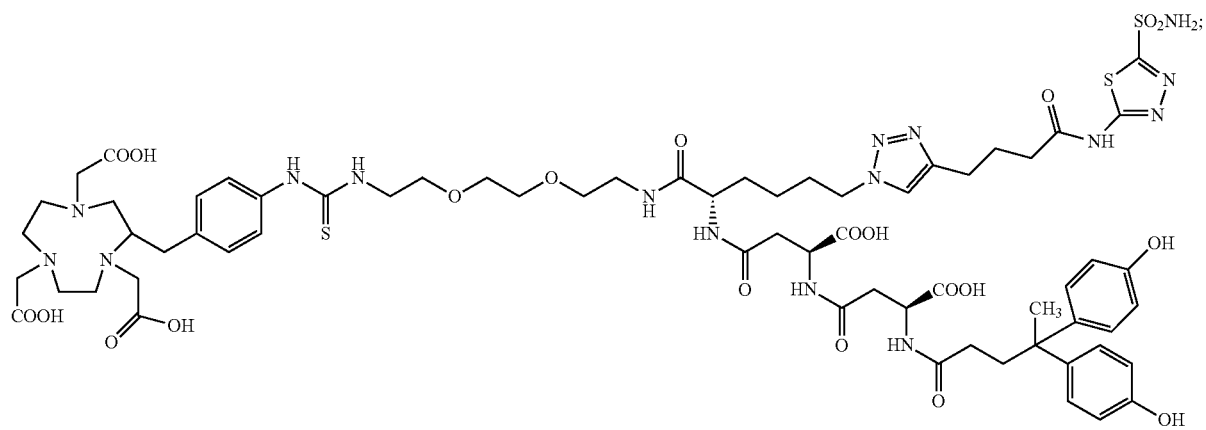
or a pharmaceutically acceptable salt thereof.
12. The compound of claim 1, wherein the compound of formula (I) is selected from the group consisting of:

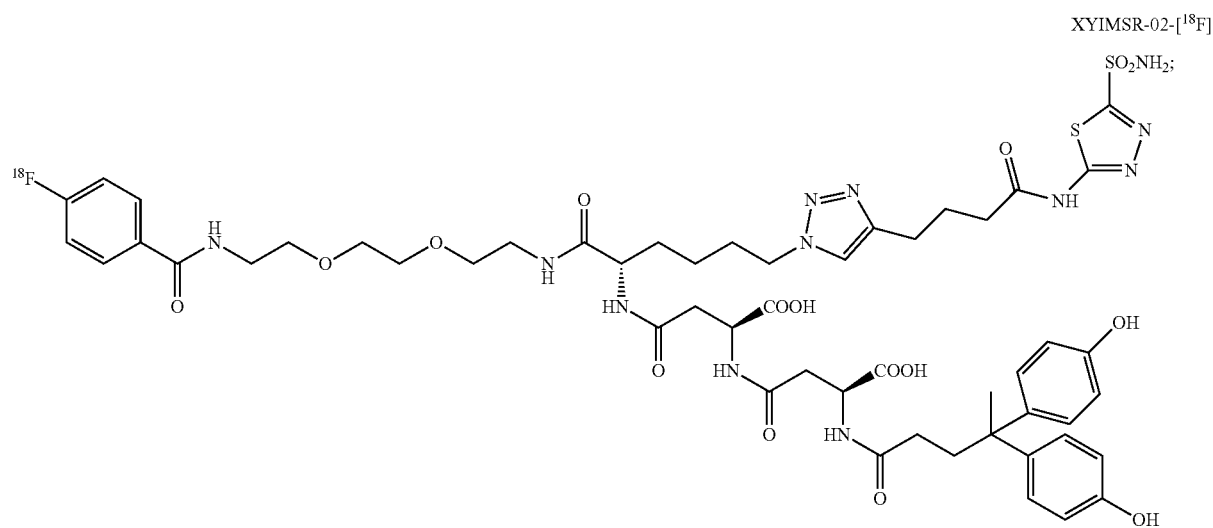
XYIMSR-02-[18F]
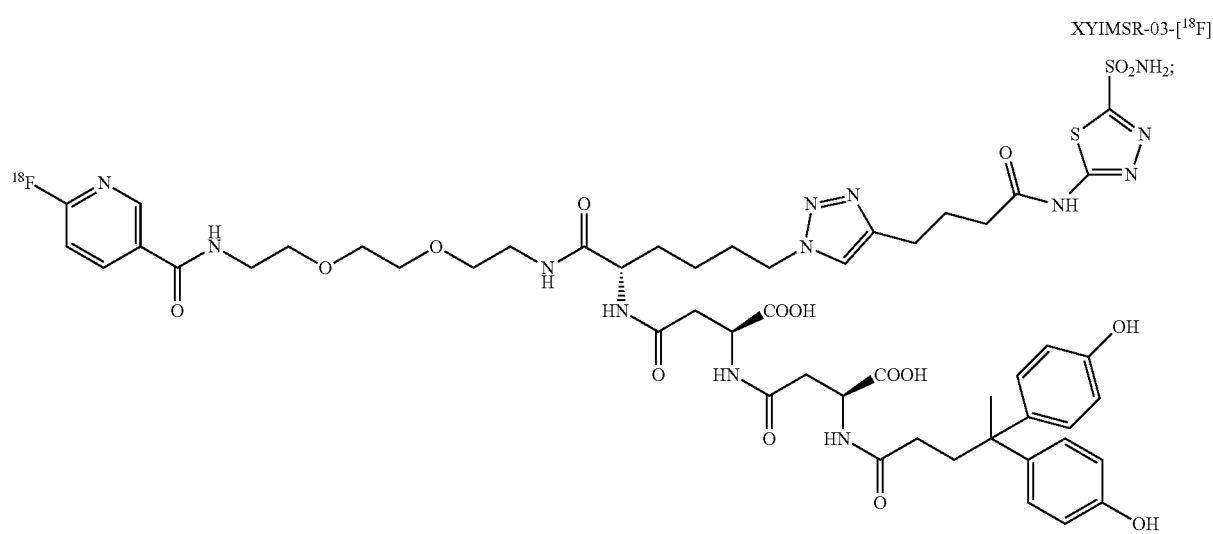
XYIMSR-03-[18F]
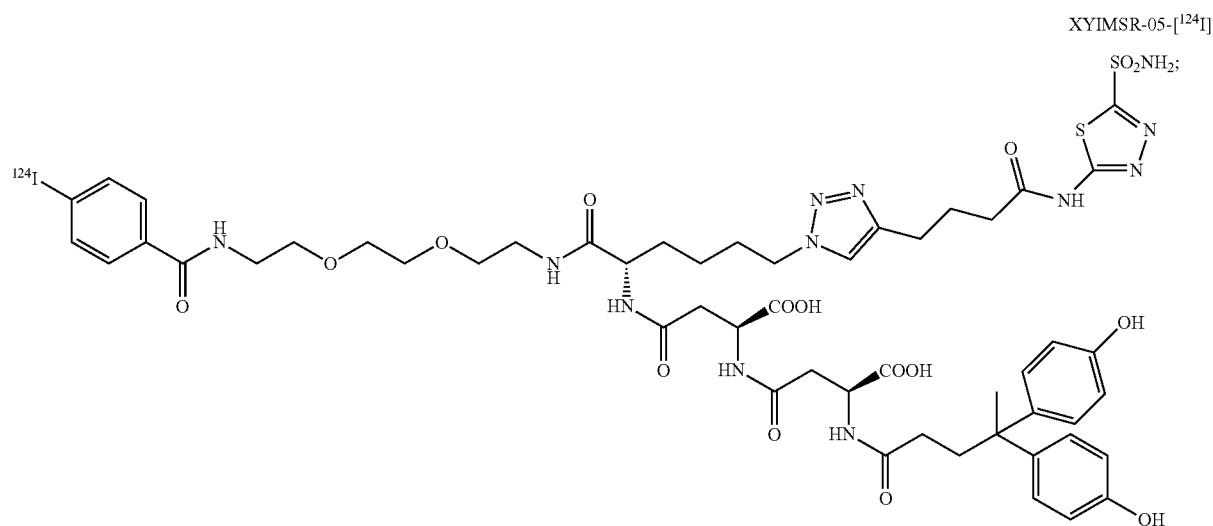
XYIMSR-05-[124I]

-continued
XYIMSR-05-[125I]
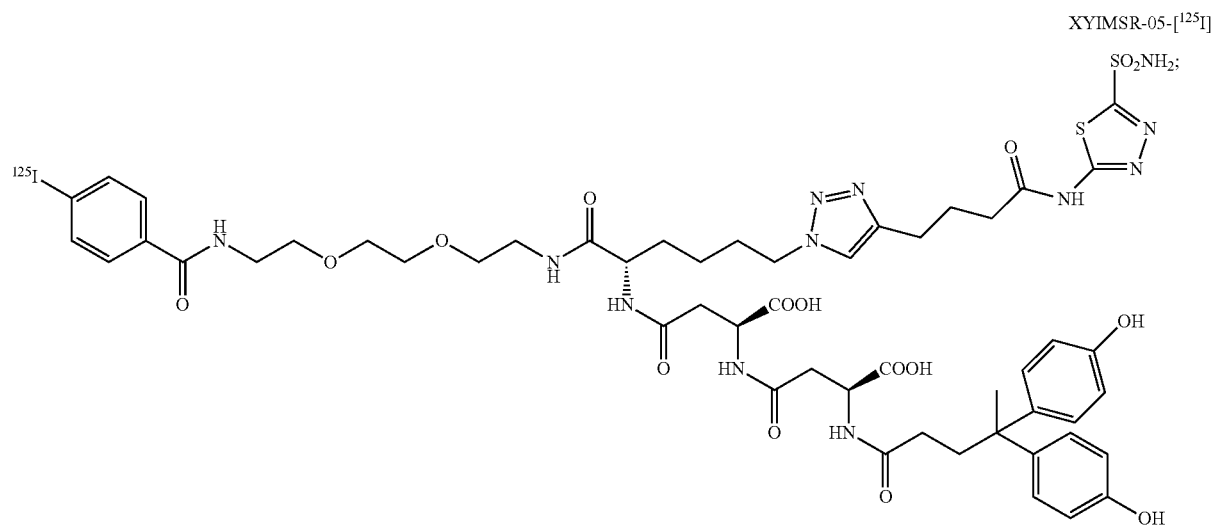
XYIMSR-05-[131I]
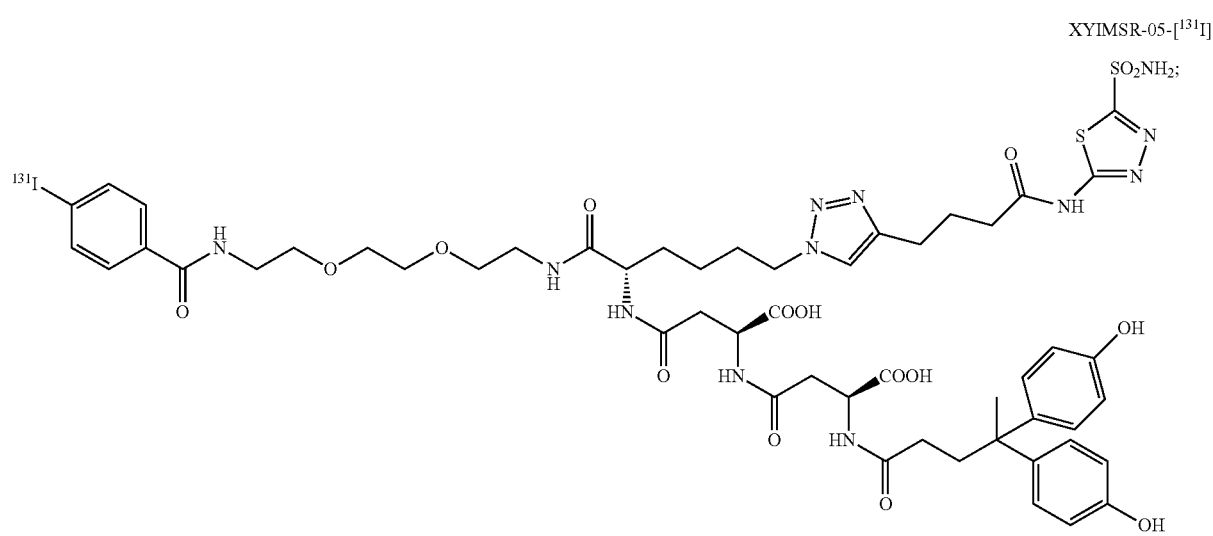
XYIMSR-01-[111In]
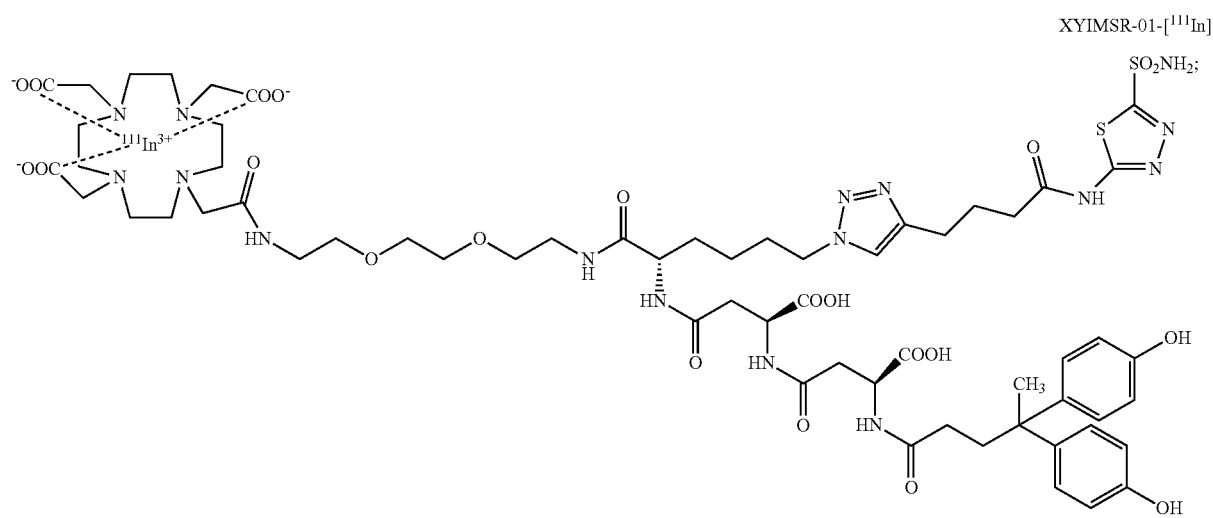

-continued
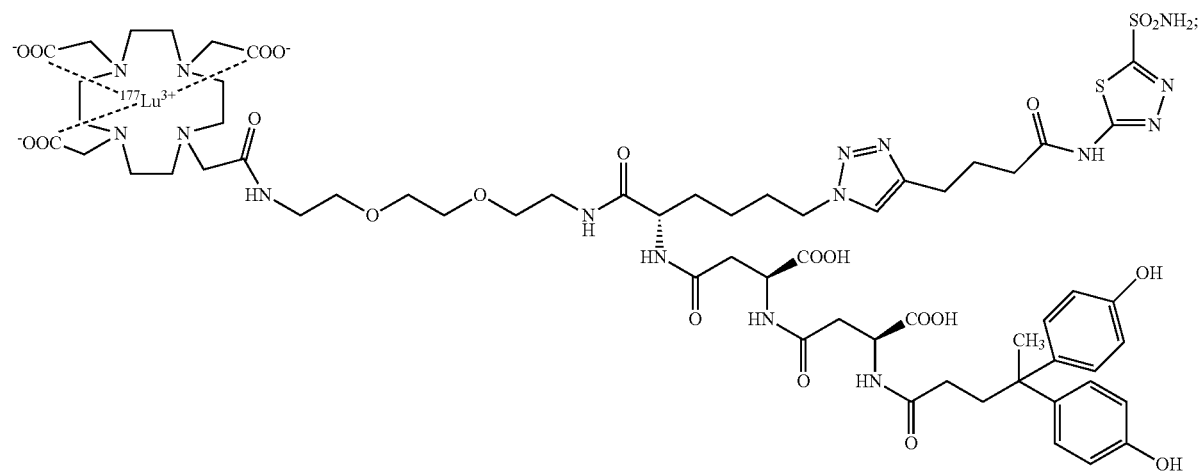
XYIMSR-01-[¹⁷⁷Lu]
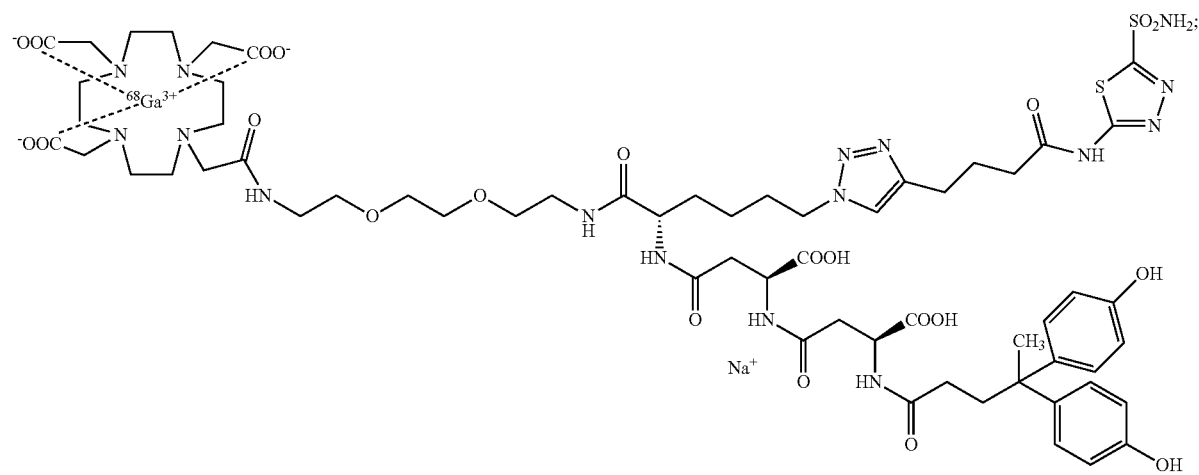
XYIMSR-01-[⁶⁸Ga]
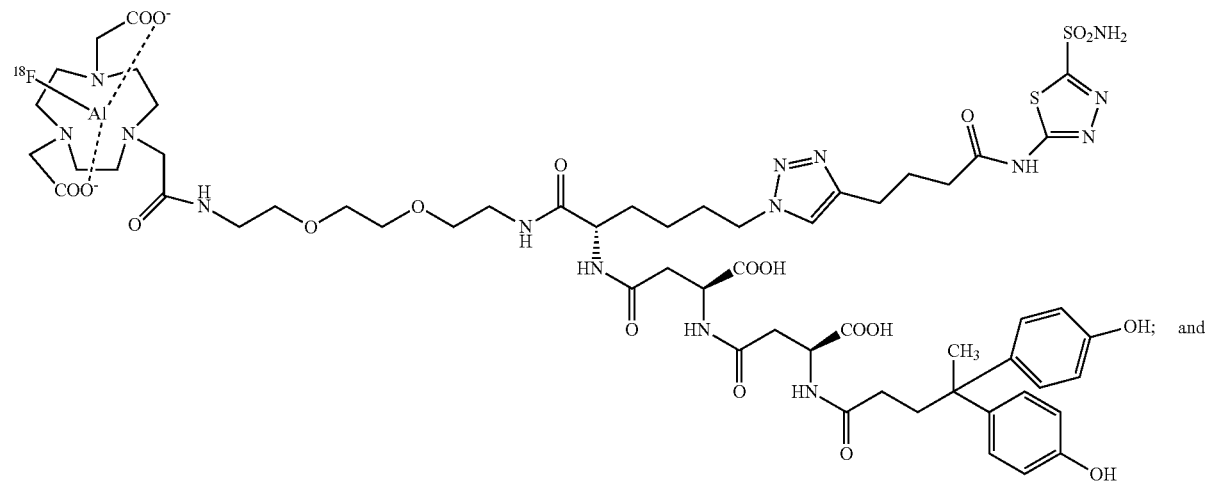
XYIMSR-04-[Al¹⁸F]
and -continued XYIMSR-06-[$^{64}$Cu]

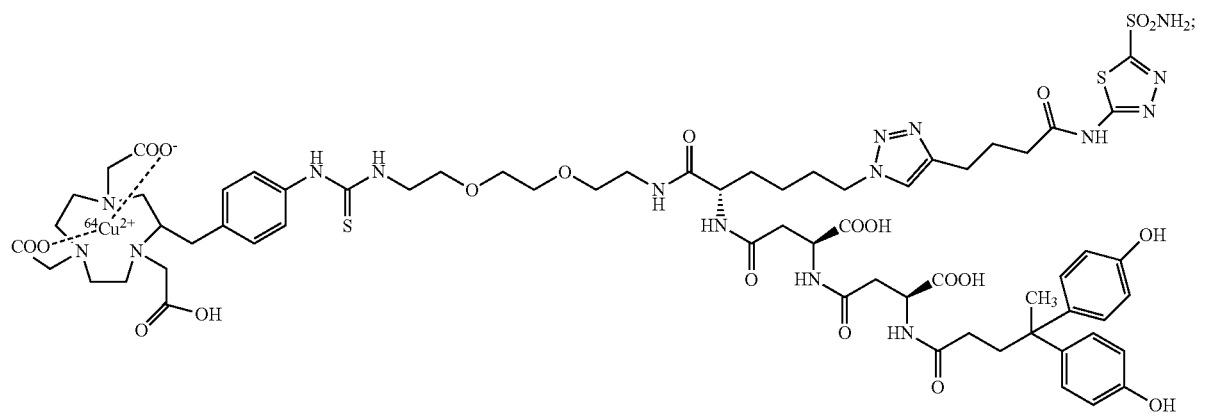

or a pharmaceutically acceptable salt thereof.

13. A method for imaging or treating one or more Carbonic Anhydrase IX expressing tumors or cells, the method comprising administering and or contacting the one or more tumors or cells with an effective amount of a compound of formula (I) and taking an image, the compound of formula (I) comprising:

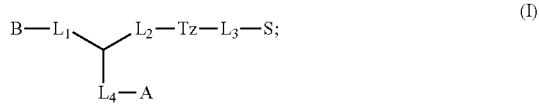

wherein:
B is a metal chelating moiety comprising a radiometal, or a radio-halogenated prosthetic group;
$L_1$, $L_2$, $L_3$, and $L_4$ are —$C_1$-$C_{24}$ alkyl-, wherein each alkyl group is optionally substituted with one to four groups selected from the group consisting of =O, =S, and —COOR and one to six of the methylene groups in each alkyl group is optionally replaced by —O—, —S—, or —(NR')—, provided that no two adjacent methylene groups are both replaced by —O—, —S—, or —(NR')—;
each R and R' is independently selected from the group consisting of hydrogen, $C_1$-$C_6$ alkyl, $C_2$-$C_{12}$ aryl, and $C_4$-$C_{16}$ alkyl aryl;
Tz is a triazole group selected from the group consisting of

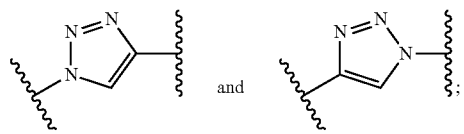 [SMILES: *c1cn(*)nn1 ; *c1cn(*)nn1]

S is a sulfonamide targeting a catalytic pocket of CAIX selected from the group consisting of:

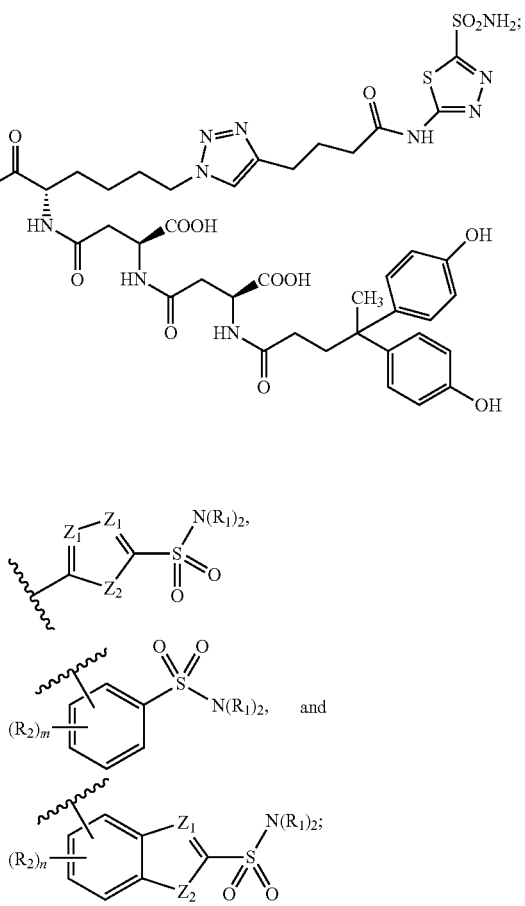

each $R_1$ is independently selected from the group consisting of hydrogen, substituted or unsubstituted alkyl, substituted and unsubstituted aryl, and substituted and unsubstituted heteroaryl;
each $R_2$ is selected from the group consisting of hydrogen, halogen, hydroxyl, alkoxyl, —CN, —CF$_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl;
m is an integer selected from the group consisting of 1, 2, 3, and 4;
n is an integer selected from the group consisting of 1, 2, and 3;
each $Z_1$ is independently selected from the group consisting of CR$_3$, and N;
each $Z_2$ is independently selected from the group consisting of CR$_3$, and S;
each $R_3$ is independently selected from the group consisting of hydrogen, halogen, hydroxyl, alkoxyl, —CN, —CF$_3$, amino, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl;

A is

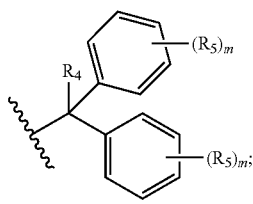

$R_4$ is independently selected from the group consisting of hydrogen, hydroxyl, alkoxyl, substituted or unsubstituted alkyl, substituted or unsubstituted alkenyl, and substituted or unsubstituted alkynyl;

$R_5$ is independently selected from the group consisting hydrogen, halogen, hydroxyl, alkoxyl, —CN, —CF$_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl;

or a pharmaceutically acceptable salt thereof.

14. The method of claim 13, wherein the compound of formula (I) is a compound of formula (II):

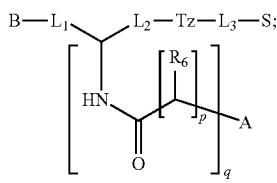

wherein:
p is an integer selected from the group consisting of 1, 2, 3, and 4;
q is an integer selected from the group consisting of 0, 1, 2, 3, and 4;
each $R_6$ is independently selected from the group consisting of H and —COOR;
or a pharmaceutically acceptable salt thereof.

15. The method of claim 14, wherein the compound of formula (II) is a compound of formula (III):

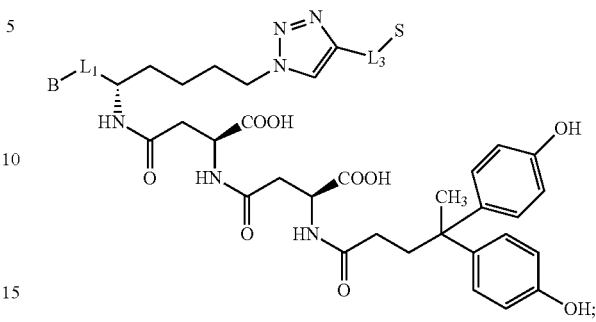

or a pharmaceutically acceptable salt thereof.

16. The method of claim 13, wherein S is selected from the group of:

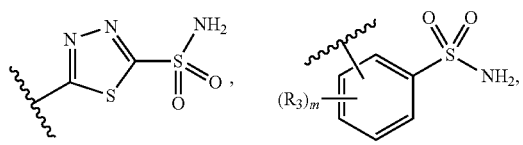

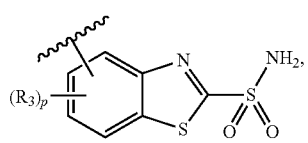

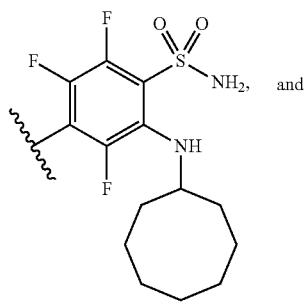

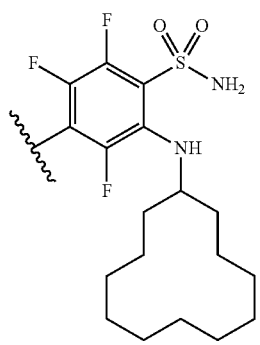

or a pharmaceutically acceptable salt thereof.

17. The method of claim 13, wherein B is a metal chelating moiety comprising a radiometal selected from the group of:

107 108
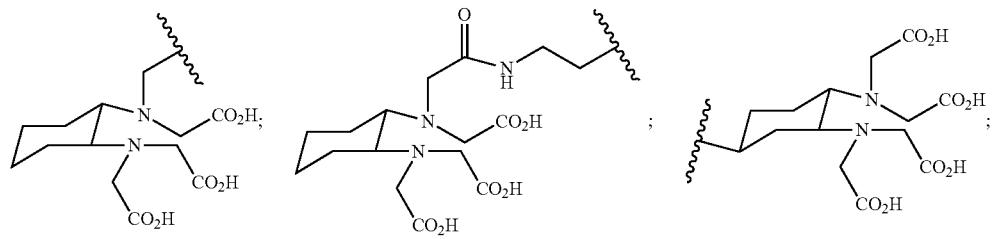
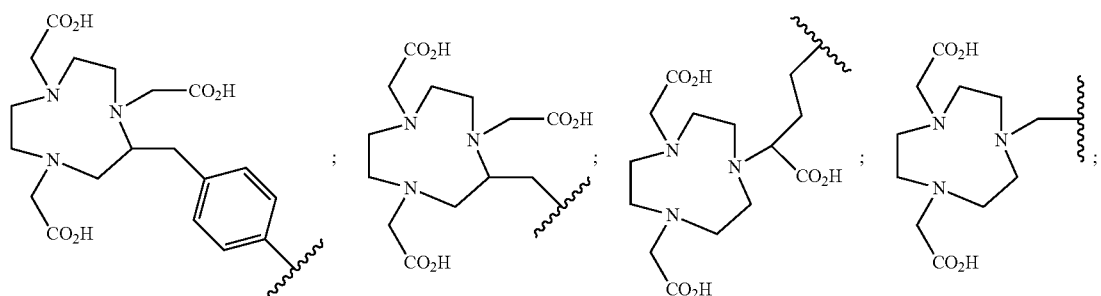
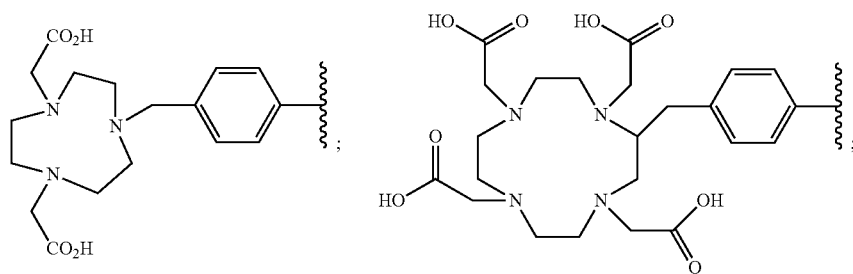
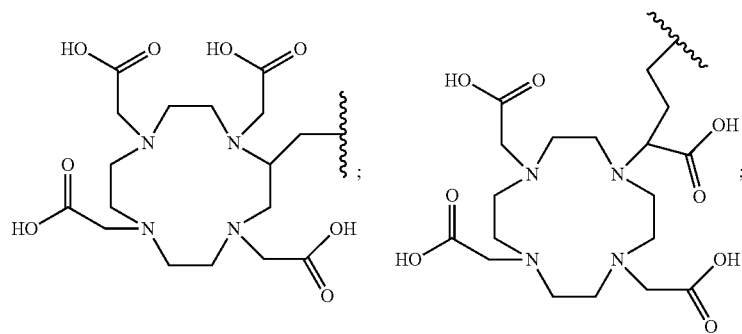
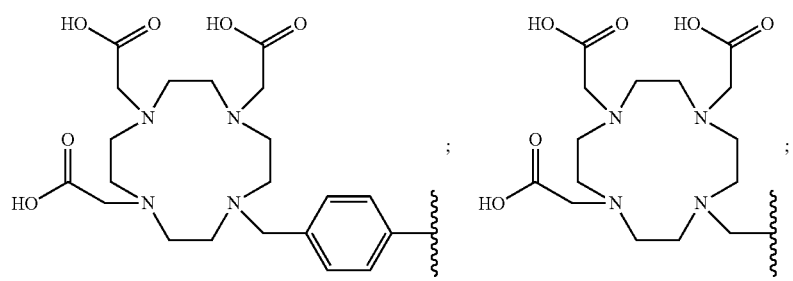

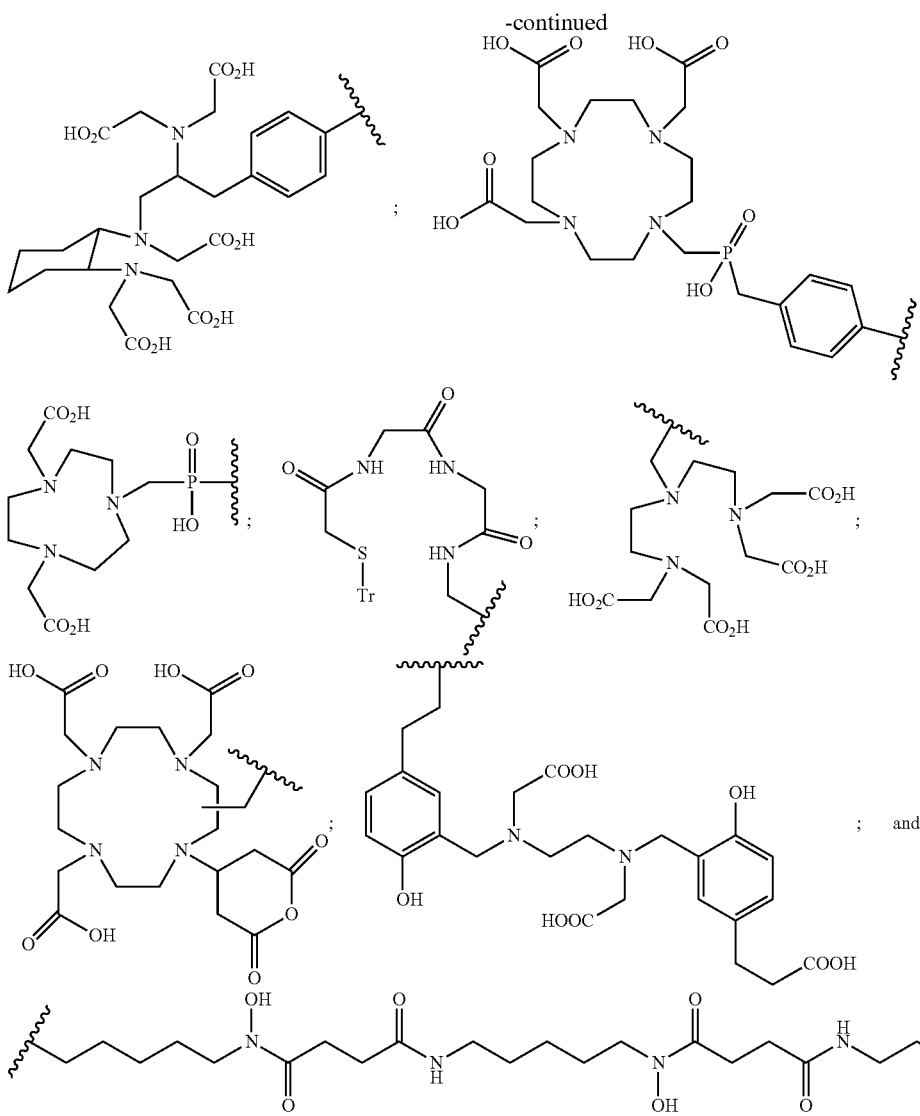

and the radiometal and is selected from the group consisting of: $^{67}$Ga, $^{68}$Ga, $^{64}$Cu, $^{67}$Cu, Al-$^{18}$F, $^{86}$Y, $^{90}$Y, $^{89}$Zr, $^{111}$In, $^{99m}$Tc, $^{177}$Lu, $^{153}$Sm, $^{186}$Re, $^{188}$Re, $^{203}$Pb, $^{212}$Pb, $^{225}$Ac, $^{212}$Bi, $^{213}$Bi, $^{47}$Sc, and $^{166}$Ho;

or wherein B is a radio-halogenated prosthetic group selected from the group consisting of:

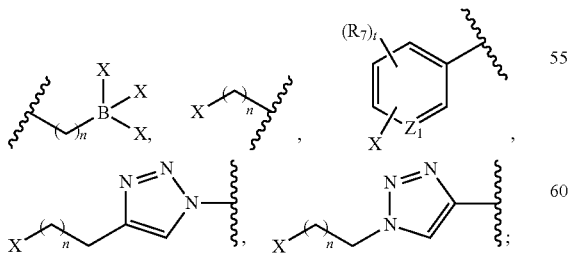

wherein:

X is a radio-halogen selected from the group consisting of: $^{18}$F, $^{76}$Br, $^{77}$Br, $^{80m}$Br, $^{125}$I, $^{124}$I, $^{131}$I, and $^{211}$At;

n is an integer selected from the group consisting of 1, 2, 3, 4, 5 and 6;

t is an integer selected from the group consisting of 1, 2, and 3;

Z1 is independently selected from the group consisting of $CR_3$, and N;

each $R_3$ and $R_7$ is selected from the group consisting of hydrogen, halogen, hydroxyl, alkoxyl, —CN, —$CF_3$, substituted or unsubstituted amine, nitro, sulfonyl, substituted or unsubstituted alkyl, substituted or unsubstituted alkenyl, substituted or unsubstituted alkynyl, substituted or unsubstituted aryl, substituted or unsubstituted heteroalkyl, substituted or unsubstituted alkylaryl substituted or unsubstituted arylalkyl, substituted or unsubstituted alkylheteroaryl, substituted or unsubstituted heteroalkylaryl, and substituted or unsubstituted naphthyl, substituted or unsubstituted biphenyl;

or a pharmaceutically acceptable salt thereof.

18. The method of claim 13, wherein the compound of formula (I) is selected from the group consisting of:

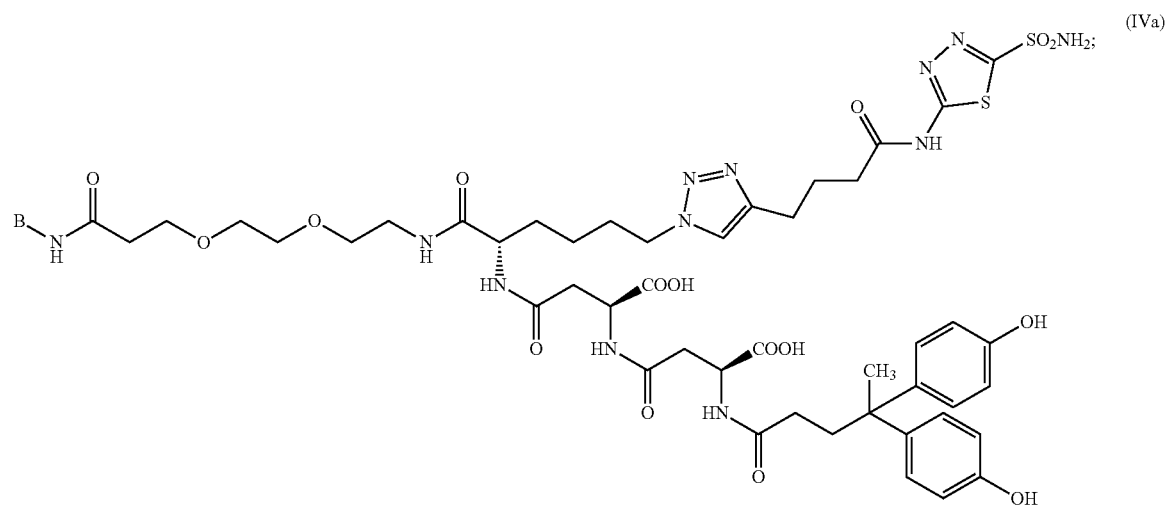
(IVa)
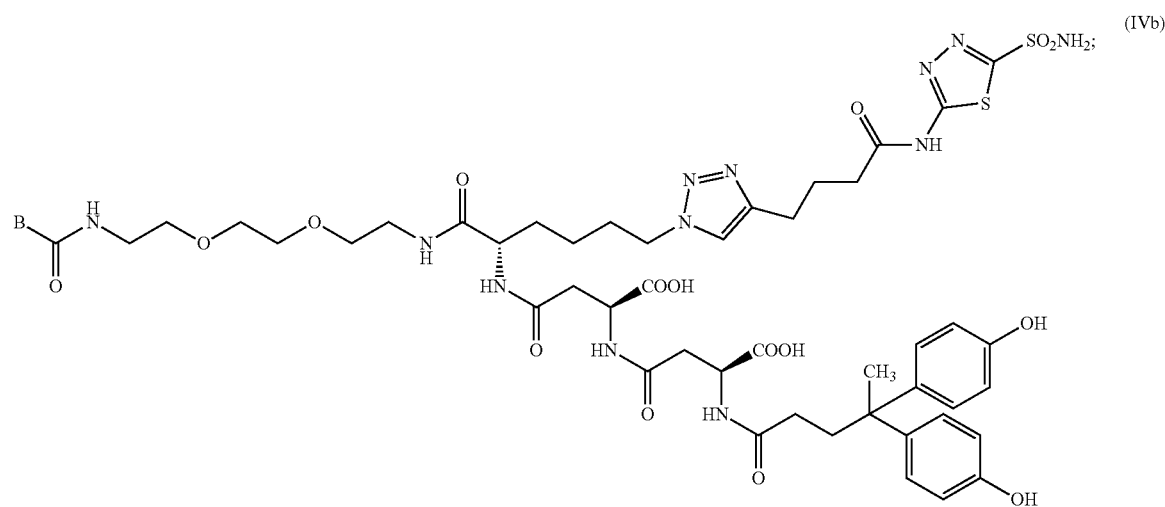
(IVb)
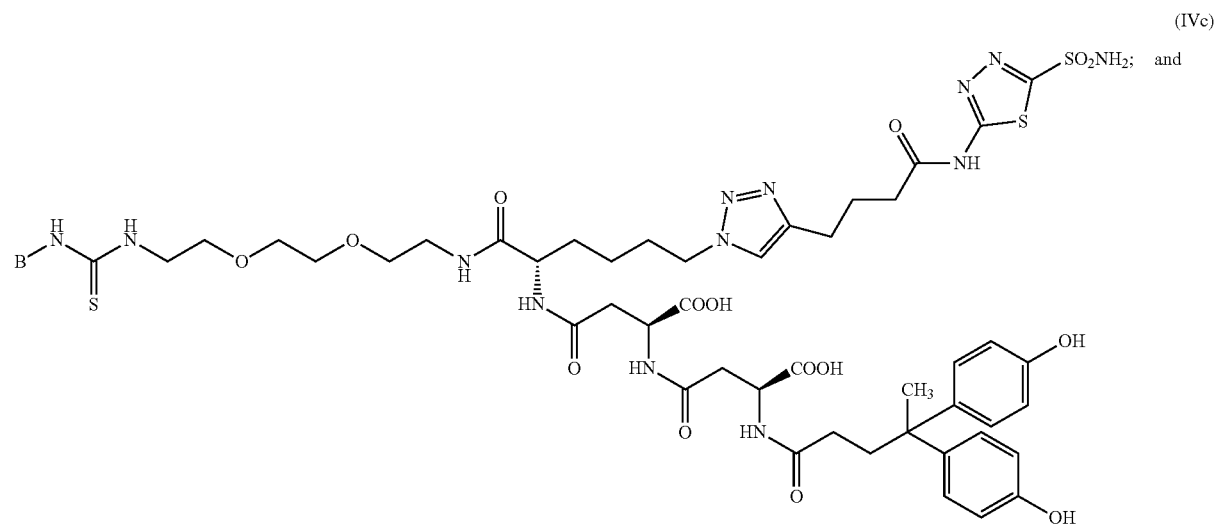
(IVc) and

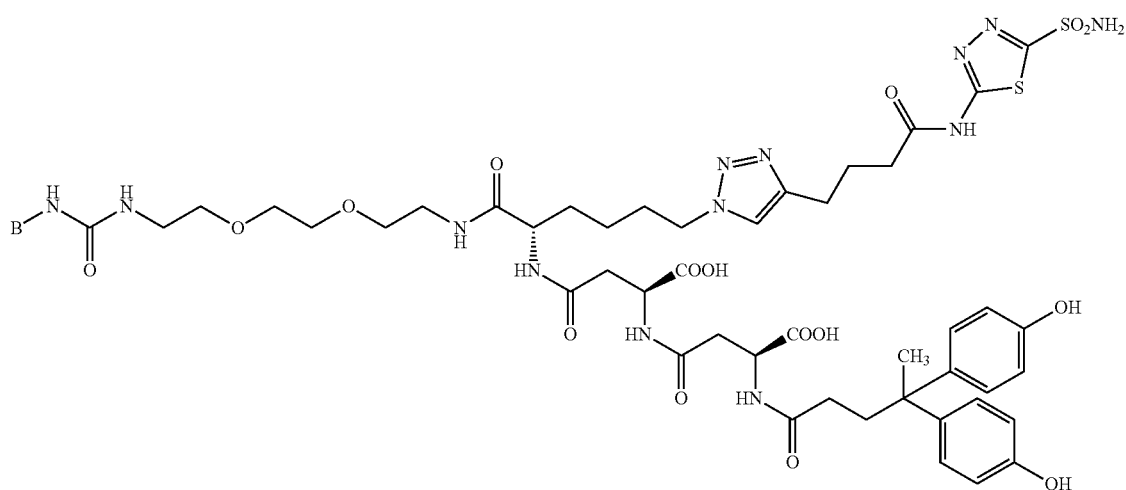
(IVd)
or a pharmaceutically acceptable salt thereof.
19. The method of claim 13, wherein the compound of formula (I) is selected from the group consisting of:
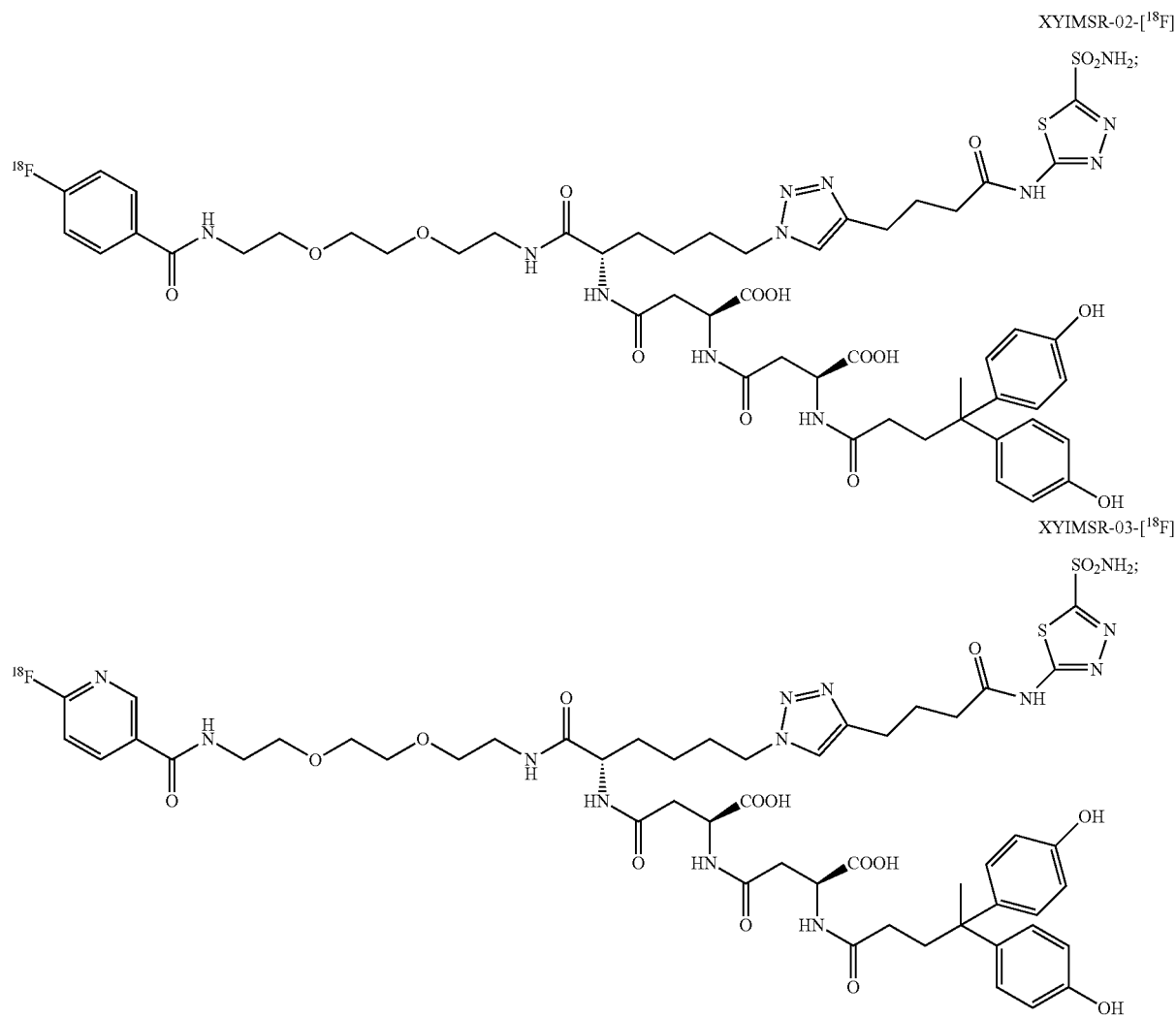
XYIMSR-02-[18F]
XYIMSR-03-[18F]

-continued
XYIMSR-05-[124I]
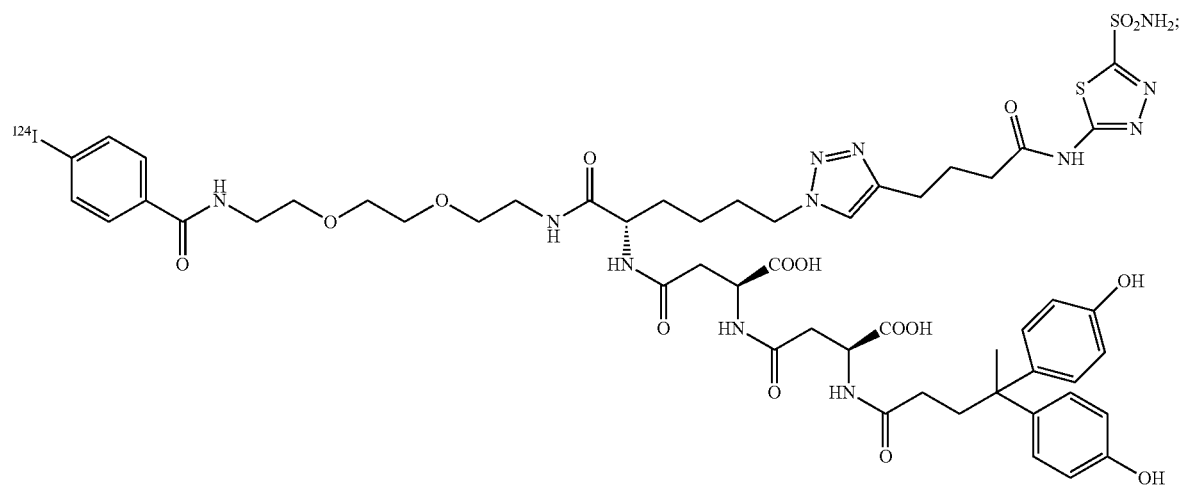
XYIMSR-05-[125I]
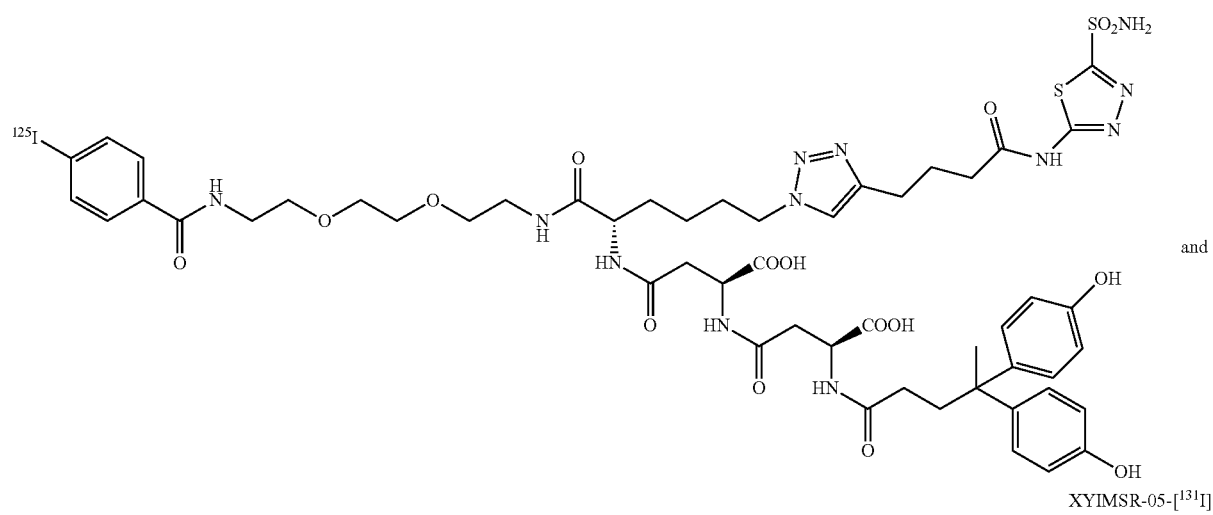
and
XYIMSR-05-[131I]
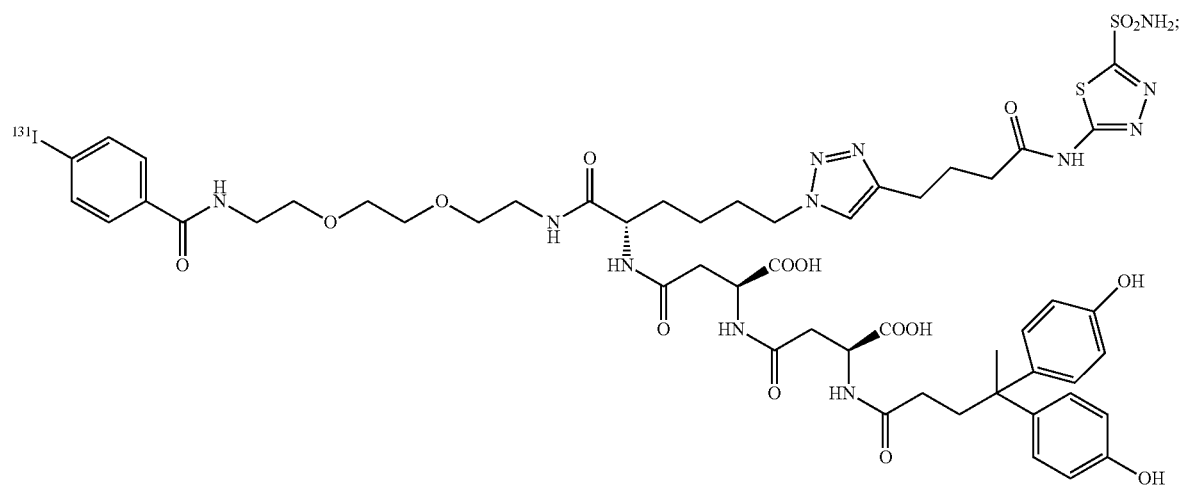
or a pharmaceutically acceptable salt thereof.
20. The method of claim 13, wherein the compound of formula (I) is selected from the group consisting of:

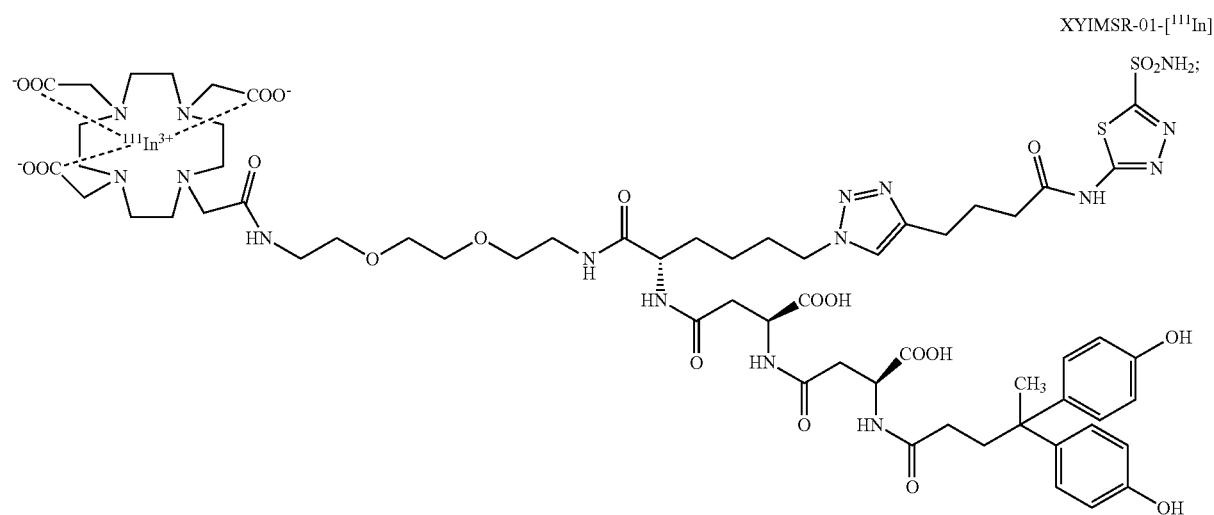
XYIMSR-01-[¹¹¹In]
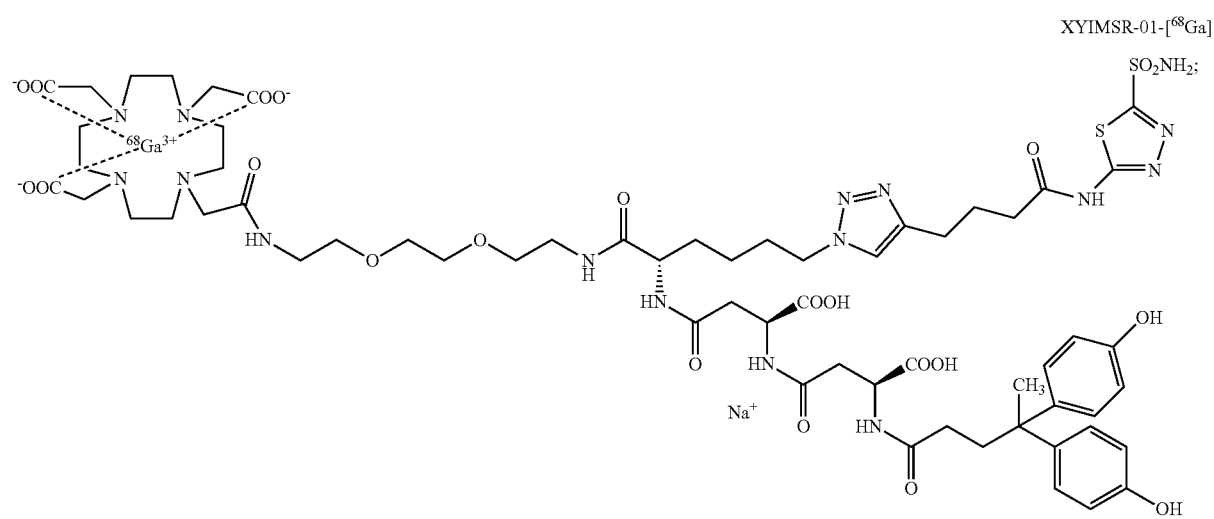
XYIMSR-01-[⁶⁸Ga]
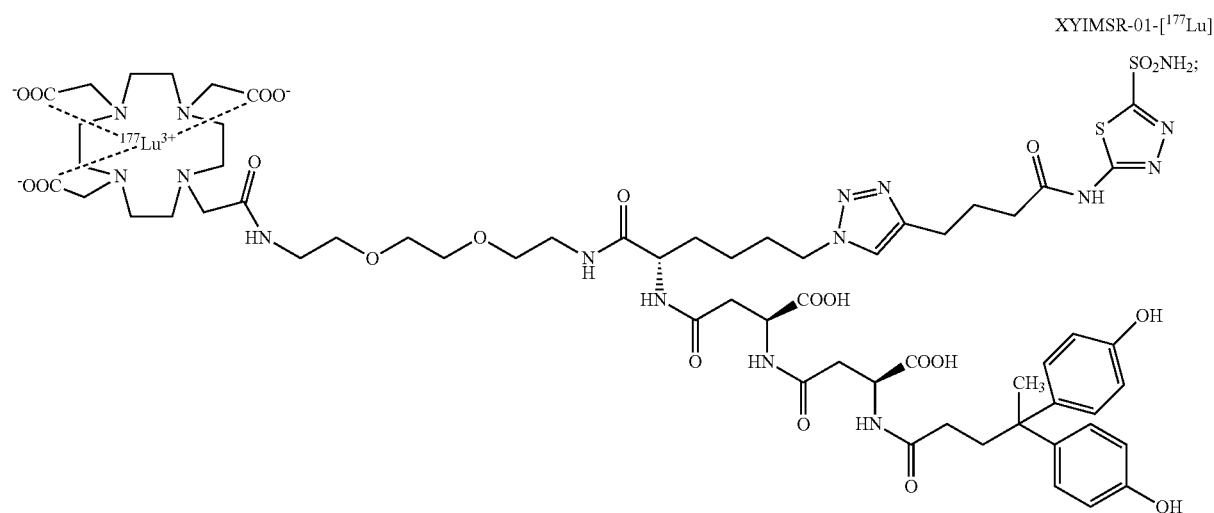
XYIMSR-01-[¹⁷⁷Lu]

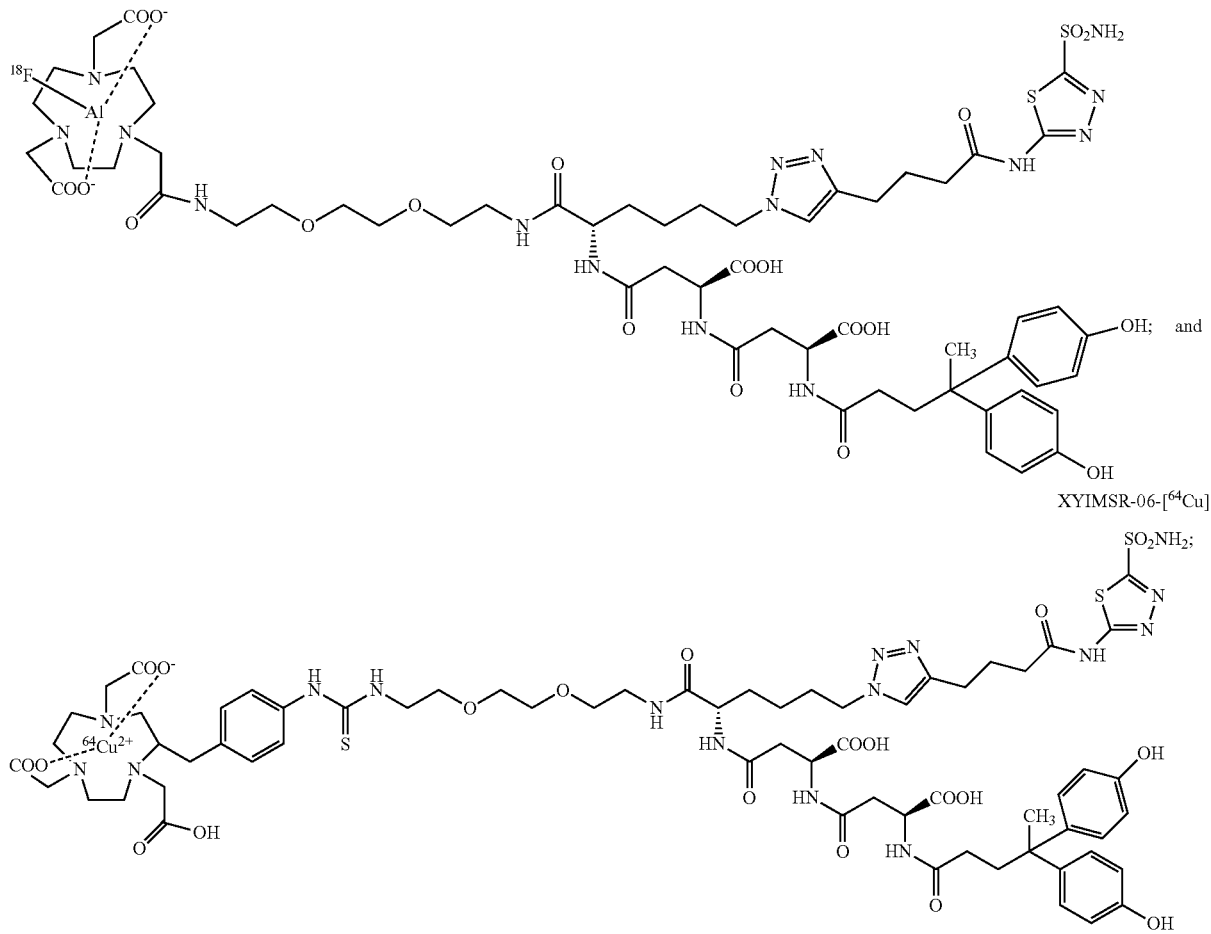

or a pharmaceutically acceptable salt thereof.

21. The method of claim 13, wherein the one or more Carbonic Anhydrase IX expressing tumors or cells is selected from the group consisting of: a renal cell carcinoma, a prostate tumor or cell, a metastasized prostate tumor or cell, a lung tumor or cell, a renal tumor or cell, a glioblastoma, a pancreatic tumor or cell, a bladder tumor or cell, a sarcoma, a melanoma, a breast tumor or cell, a colon tumor or cell, a germ cell, a pheochromocytoma, an esophageal tumor or cell, a stomach tumor or cell, and combinations thereof.

22. The method of claim 13, wherein the one or more Carbonic Anhydrase IX expressing tumors or cells is a renal cell carcinoma.

23. The method of claim 13, wherein the imaging comprises positron emission tomography (PET) imaging or single photon emission computed tomography (SPECT) imaging.

24. The method of claim 13, wherein the one or more Carbonic Anhydrase IX expressing tumors or cells is in vitro, in vivo, or ex vivo.

25. The method of claim 13, wherein the one or more Carbonic Anhydrase IX expressing tumors or cells is present in a subject.

26. The method of claim 25, wherein the compound comprising the imaging agent is cleared from the tumor or cell in the subject.

27. The method of claim 25, wherein the compound comprising the imaging agent is cleared more rapidly from a subject's kidneys than from a tumor in the subject.

* * * * *